(12) United States Patent
Chapman et al.

(10) Patent No.: US 8,450,277 B2
(45) Date of Patent: May 28, 2013

(54) METHODS FOR REDUCING BOTULINUM NEUROTOXIN A TOXICITY

(75) Inventors: Edwin R. Chapman, Madison, WI (US); Min Dong, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 13/014,971

(22) Filed: Jan. 27, 2011

(65) Prior Publication Data

US 2011/0223173 A1   Sep. 15, 2011

Related U.S. Application Data

(63) Continuation of application No. 11/546,880, filed on Oct. 12, 2006, now Pat. No. 7,985,554.

(60) Provisional application No. 60/726,879, filed on Oct. 14, 2005.

(51) Int. Cl.
*A01N 37/18* (2006.01)
(52) U.S. Cl.
USPC ........................................ 514/17.7; 514/21.3
(58) Field of Classification Search
None
See application file for complete search history.

(56) References Cited

FOREIGN PATENT DOCUMENTS

| WO | 2005/016233 A2 | 2/2005 |
| WO | 2007/048638 A2 | 5/2007 |

OTHER PUBLICATIONS

Bajjalieh SM et al., J. Neurosci., 1994,14:5223-5235.
Bajjalieh SM et al., Proc. Natl. Acad. Sci. USA, 1993, 90:2150-2154.
Feany MB et al., Cell, 1992, 70:861-867.
Janz R and Sudhof TC, Neuroscience, 1999, 94:1279-1290.
Janz R et al., Neuron, 1999, 24:1003-1016.
Scranton TW et al., J Neurochem, 1993, 61:29-44.
Bindra PS et al., Gene, 1993,137:299-302.
Database Genesequence: Jun. 5, 2002, "Novel Central Nervous System Protein #308".
Database UnitProt: Oct. 11, 2005, "12 Days Embryo Embryonic Body Between Diaphragm Region and Neck cDNA, RIKEN Full-Length Enriched Library, Clone:9430053C09 Product:Synaptic Vesicle Glycoprotein 2c, Full Insert Sequence. (Fragment)."
Robinson Renee F et al, The Annals of Pharmacotherapy, 2003, (37)1:127-131.
Dong Min et al. Science, 2006, 28:592-596.
Marhold Stefan et al., FEBS Letters, 2006, (580)8:2011-2014.
Buckley K et al., Journal of Cell Biology, 1985, 100:1284-1294.
ISR Jul. 26, 2007 PCT/US2006/040685.

*Primary Examiner* — Patricia A Duffy
(74) *Attorney, Agent, or Firm* — Quarles & Brady LLP

(57) ABSTRACT

The present invention is based on the identification of synaptic vesicle glycoprotein SV2 as the BoNT/A receptor and the further identification of various BoNT/A-binding fragments of SV2. The disclosure here provides new tools for diagnosing and treating botulism.

3 Claims, 10 Drawing Sheets

FIG. 2a

|  | Brain extract | BoNT/A | anti-Syp IP | anti-SV2 IP | No Ab control |
|---|---|---|---|---|---|
| BoNT/A |  | ▬ |  | ▬ |  |
| SV2 | ▬ |  |  | ▬ |  |
| Syp | ▬ |  | ▬ |  |  |

FIG. 2b

|  | BoNT/A | No Ab control | anti-SV2 IP | | | | | |
|---|---|---|---|---|---|---|---|---|
| BoNT/A (nM) | 50 |  | 50 | | 20 | | 7.5 | |
| Gangliosides | + |  | − | + | − | + | − | + |
| BoNT/A | ▬ |  | ▬ | ▬ | ▬ | ▬ |  | ▬ |

FIG. 2c

|  | BoNT/A total | GST | SV2A-L4 | SV2B-L4 | SV2C-L4 |
|---|---|---|---|---|---|
| BoNT/A | ▬ |  | ▬ | ▬ | ▬ |
| BoNT/B |  | ▬ |  |  |  |
| BoNT/E |  | ▬ |  |  |  |

FIG. 2d

454 — SV2C-L4 (luminal domain 4) — 580
TMS 7                                          TMS 8

SV2C-L4 truncations

|  | BoNT/A | GST | 454-580 | 519-580 | 529-580 | 534-580 | 454-566 | 454-562 | 454-546 | 454-541 | 529-566 | 529-562 | 529-556 |
|---|---|---|---|---|---|---|---|---|---|---|---|---|---|
| BoNT/A | ▬ |  | ▬ | ▬ | ▬ |  | ▬ | ▬ | ▬ |  | ▬ |  |  |

```
                529                                              566
       ┌─────────────────────────────────────────────────────────────┐
         *                                      *
SV2C  FDDVTSV NTYFKNCTF DTL FENTD FEP YKF TDSE FQ NCS FLHNK TGC Q I T
SV2A  FEDVTSS NTFFRNCTF INTV FYNTDL FE YKF VNS RLV NSTFLHNKEGC P L D
SV2B  FEDVTSTD TYFKNCT IES TT FYNTDL YKH KFIDCRF I NSTFLEQKEGC HM D
```

FIG. 2e

Vesicle Lumen

L4

Critical region in SV2C for BoNT/B blinding

L1  L2  L3          L5

N

Cytoplasm

Fig. 4 c  Rapid mouse toxicity assay

| Genotype (littermates) | Time-to-death (min) | | | | Average effective toxicity (LD$_{50}$/ml) |
|---|---|---|---|---|---|
| | Pair: 1 | 2 | 3 | 4 | |
| WT | 27 | 36 | 35 | 33 | $8.4 \pm 2.9 \times 10^5$ |
| SV2B (-/-) | 44 | 46 | 42 | 41 | $3.4 \pm 0.5 \times 10^5$ |

```
        Y Y G L T V W F P D M I R H L Q S D E Y  Majority
        ------+------------------+-------------
              450                460
        ------+------------------+-------------
447     Y Y G L S V W F P D V I K H L Q S D E Y  SV2C-rat-protein
461     Y Y G L T V W F P D M I R H L Q A V D Y  SV2A-human-protein
404     Y Y G L T V W F P D M I R Y F Q D E E Y  SV2B-human-protein
447     Y Y G L S V W F P D V I K P L Q S D E Y  SV2C-human-protein
461     Y Y G L T V W F P D M I R H L Q A V D Y  SV2A-mouse-protein
404     Y Y G L T V W F P D M I R Y F Q D E E Y  SV2B-mouse-protein
447     Y Y G L S V W F P D V I K H L Q S D E Y  sv2c-mice-protein A L L T K V F Q G E K V A N F T I N F T  Majority
        ------+------------------+-------------
              470                480
        ------+------------------+-------------
467     A L L T R N V Q K D K Y A N F S I N F T  SV2C-rat-protein
481     A S R T K V F P G E R V E H V T F N F T  SV2A-human-protein
424     K S K M K V F F G E H V Y G A T I N F T  SV2B-human-protein
467     A L L T R N V E R D K Y A N F T I N F T  SV2C-human-protein
481     A A R T K V F P G E R V E H V T F N F T  SV2A-mouse-protein
424     K S K M K V F F G E H V H G A T I N F T  SV2B-mouse-protein
467     A L L T R N V Q K D K Y A N F S I N F T  sv2c-mice-protein M E N Q I H T G G E Y V N D K F I G V K  Majority
        ------+------------------+-------------
              490                500
        ------+------------------+-------------
487     M E N Q V H T G M E Y D N G R F L G V K  SV2C-rat-protein
501     L E N Q I H R G G Q Y F N D K F I G L R  SV2A-human-protein
444     M E N Q I H Q H G K L V N D K F T R M Y  SV2B-human-protein
487     M E N Q I H T G M E Y D N G R F I G V K  SV2C-human-protein
501     L E N Q I H R G G Q Y F N D K F I G L R  SV2A-mouse-protein
444     M E N Q I H Q H G K L V N D K F I K M Y  SV2B-mouse-protein
487     M E N Q I H T G M E Y E N G R F L G V K  sv2c-mice-protein F K S V T F E D S V F K S C Y F E D V T  Majority
        ------+------------------+-------------
              510                520
        ------+------------------+-------------
507     F K S V T F K D S V F K S C T F D D V T  SV2C-rat-protein
521     L K S V S F E D S L F E E C Y F E D V T  SV2A-human-protein
464     F K H V L F E D T F F D E C Y F E D V T  SV2B-human-protein
507     F K S V T F K D S V F K S C T F E D V T  SV2C-human-protein
521     L K S V S F E D S L F E E C Y F E D V T  SV2A-mouse-protein
464     F K H V L F E D T F F D K C Y F E D V T  SV2B-mouse-protein
507     F K S V T F K D S V F K S C T F D D V T  sv2c-mice-protein S V N T Y F K N C T F I D T V F Y N T D  Majority
        ------+------------------+-------------
              530                540
        ------+------------------+-------------
527     S V N T Y F K N C T F I D T L F E N T D  SV2C-rat-protein
541     S S N T F F R N C T F I N T V F Y N T D  SV2A-human-protein
484     S T D T Y F K N C T I E S T I F Y N T D  SV2B-human-protein
527     S V N T Y F K N C T F I D T V F D N T D  SV2C-human-protein
541     S S N T F F R N C T F I N T V F Y N T D  SV2A-mouse-protein
484     S T D T Y F K N C T I E S T T F Y N T D  SV2B-mouse-protein
527     S V N T Y F K N C T F I D T L F D N T D  sv2c-mice-protein L E E Y K F I N S R F I N S T F L H N K  Majority
        ------+------------------+-------------
              550                560
        ------+------------------+-------------
547     F E P Y K F I D S E F Q N C S F L H N K  SV2C-rat-protein
561     L F E Y K F V N S R L I N S T F L H N K  SV2A-human-protein
504     L Y E H K F I N C R F I N S T F L E Q K  SV2B-human-protein
547     F E P Y K F I D S E F K N C S F F H N K  SV2C-human-protein
561     L F E Y K F V N S R L V N S T F L H N K  SV2A-mouse-protein
504     L Y K H K F I N C R F I N S T F L E Q K  SV2B-mouse-protein
547     F E P Y K F I D S E F Q N C S F L H N K  sv2c-mice-protein
```

Fig. 9

METHODS FOR REDUCING BOTULINUM NEUROTOXIN A TOXICITY

CROSS-REFERENCE TO RELATED APPLICATIONS

This application is a continuation of U.S. patent application Ser. No. 11/546,880, filed Oct. 12, 2006 now U.S. Pat. No. 7,985,554, which claims the benefit of U.S. Provisional Application No. 60/726,879, filed on Oct. 14, 2005, both of which are herein incorporated by reference in their entirety.

STATEMENT REGARDING FEDERALLY SPONSORED RESEARCH OR DEVELOPMENT

This invention was made with government support under Grant Nos. AI057153 and AI057744 awarded by the National Institutes of Health. The government has certain rights in the invention.

BACKGROUND OF THE INVENTION

Botulinum neurotoxin A (BoNT/A) is one of seven botulinum neurotoxins (designated BoNT/A-G) produced by the anaerobic bacteria strain *Clostridium botulinum* (Schiavo G et al., *Physiol. Rev.* 80:717-766, 2000). BoNTs block neurotransmitter release by cleaving members of the membrane fusion machinery composed of SNAP-25, vamp-2/synaptobrevin (Syb), and syntaxin (Jahn R and Niemann H, *Ann. NY Acad. Sci.* 733:245-255, 1994; Schiavo G. et al., supra, 2000). Cleavage of these proteins in motor nerve terminals blocks acetylcholine release at the neuromuscular junction (NMJ) which causes paralysis and may lead to death due to respiratory failure (Schiavo G. et al., supra, 2000; Simpson L L, *Ann. Rev. Pharmacol. Toxicol.* 44:167-193, 2004). Due to extreme potency and lethality as well as ease of use and transport, BoNTs are considered one of the six most dangerous potential bioterrorism threats (designated by Center for Disease Control of United States) (Arnon S. et al., *JAMA* 285:1059-1070, 2001). According to the American Medical Society, as little as one gram of crystalline toxin is sufficient to kill one million people.

Currently, the standard test for BoNTs is the mouse bioassay available at the Centers for Disease Control and Prevention (CDC) and select laboratories across the country. The test involves treating mice with clinical samples suspected of carrying one of the BoNTs. The mice are immunized against the various BoNTs, and only those mice immunized against the specific BoNT present in the sample will survive. Although the test is sensitive in that it can detect as little as 0.03 ng of a BoNT, it is expensive and takes days to complete. On the treatment side, equine antitoxin containing antibodies against a BoNT is the therapy of choice and its effectiveness depends on timely treatment. This treatment, however, has all the disadvantages of a horse serum product such as the risks of anaphylaxis and serum sickness. Many times, treatment begins before botulism is confirmed as the diagnostic test takes days which is too long to wait for effective treatment. Therefore, there is a need in the art for alternative detection and treatment strategies.

BRIEF SUMMARY OF THE INVENTION

The present invention is based on the identification of synaptic vessel glycoprotein SV2 as the BoNT/A receptor and the further identification of various BoNT/A-binding fragments of SV2. The disclosure here provides new tools for diagnosing and treating botulism.

BRIEF DESCRIPTION OF THE SEVERAL VIEWS OF THE DRAWINGS

The file of this patent contains at least one drawing executed in color. Copies of this patent with color drawings will be provided by the Patent and Trademark Office upon request and payment of the necessary fee.

FIG. 2 shows that BoNT/A binds directly to SV2 luminal domains. Panel a: Monoclonal antibodies against the synaptic vesicle proteins synaptophysin (Syp, CI7.2) and SV2 (pan-SV2), were used to co-immunoprecipitate BoNT/A (100 nM) from rat brain detergent extract. Control samples without antibodies (No Ab) were carried out in parallel. Immunoprecipitated toxin and vesicle proteins were detected by western blot. BoNT/A co-immunoprecipitated with SV2, but not Syp. Panel b: Co-immunoprecipitations of BoNT/A from mouse brain detergent extract were carried out with pan-SV2 antibodies, with or without exogenous gangliosides (mixture of bovine brain gangliosides, 0.6 mg/ml), at the indicated BoNT/A concentrations. Adding gangliosides increased the amount of BoNT/A co-immunoprecipitated by SV2 antibodies. Panel c: The 4$^{th}$ luminal domains of all three SV2 isoforms (see panel d for SV2 topology) were purified as GST-tagged proteins and immobilized on glutathione-sepharose beads. Pull down assay were carried out using 8 μg immobilized proteins and 100 nM toxins (BoNT/A, B or E). Bound materials were analyzed by western blot with anti-BoNT/A, B, E antibodies. BoNT/A binds directly to all SV2 isoforms with the luminal domain of SV2C showing the highest apparent affinity. Panel d: Schematic view of putative SV2 topology. Each circle represents a residue. Filled circles indicate conserved residues in all SV2A, B and C isoforms, gray circles are residues conserved in two of SV2 isoforms, and open circles represent non-conserved residues. SV2 contains 12 transmembrane domains with its N- and C-terminus facing the cytoplasm. The $4^{th}$ luminal domain (L4) lies inside vesicles and contains three putative N-glycosylation sites, indicated. The critical region in SV2C for BoNT/A binding is indicated by arrows (see panel e for details). Panel e: A series of truncation mutants within SV2C-L4 were generated as GST fusion proteins and tested for BoNT/A binding. Binding assays were performed as described in panel b and analyzed by western blot. The critical region for BoNT/A binding was mapped to a short fragment (residues 529-566 in SV2C), which alone maintains the ability to bind BoNT/A. Immobilized GST fusion proteins were shown by Ponceau S staining to ensure that equal amount of immobilized protein were used in the assay. The protein sequence of this region is aligned with regions of SV2A and B (all are rat sequences), with putative N-glycosylation sites indicated by asterisks.

FIG. 3 shows the block of BoNT/A binding and entry into hippocampal neurons and motor nerve terminals by an SV2C luminal fragment. Panel a, left panel: hippocampal neurons were exposed to BoNT/A (10 nM) and Syt $I_N$ Ab in High $K^+$ buffers for 10 min, with the presence of either control protein (soluble GST, 10 µM) or SV2C-L4 (soluble GST tagged SV2C-L4 fragment, 10 µM). Cells were washed and fixed. Binding and uptake of Syt $I_N$ Ab and BoNT/A were analyzed through subsequent immunostaining SV2C-L4 did not affect Syt $I_N$ Ab uptake into neurons, but reduced BoNT/A binding to the same neurons. Panel a, right panel: The experiment was carried out as described above except using BoNT/B instead of BoNT/A. SV2C-L4 did not affect BoNT/B binding to neurons. Panel b: Hippocampal neurons were incubated with BoNT/A (10 nM), in the presence of either GST proteins or SV2C-L4, for 10 min in High $K^+$ buffers. Cells were washed three times and further incubated for 6 hrs in culture medium. Cells were then fixed and permeabilized. Cleavage of SNAP-25 was detected using a monoclonal antibody (anti-SNAP-25-C) that only recognizes cleaved SNAP-25 (but not intact full-length SNAP-25). SV2C-L4 prevented the cleavage of native SNAP-25 by BoNT/A. The third image column on the right shows images obtained from DIC microscopy. Panel c: Mouse hemi-diaphragm preparations were exposed to BoNT/A (10 nM) or BoNT/B (10 nM) in the presence of either GST protein or SV2C-L4 for 30 min in High $K^+$ buffer. Tissues were washed, fixed and permeabilized. NMJs were labeled with α-BTX. BoNT/A and B were detected with their polyclonal antibodies, respectively. SV2C-L4 specifically reduced binding of BoNT/A to NMJs, while it has no effect on BoNT/B binding. Panel d: Binding of BoNT/A and B to NMJs, based on images collected in panel c, were quantified as described in FIG. 1a. SV2C-L4 significantly reduced BoNT/A binding (65% reduction compared to control, P<0.0001, t-test, n=76-90 images), but did not affect BoNT/B binding (P>0.05, t-test, n=49-55 images). Error bars represent SEM.

FIG. 4 shows that BoNT/A binding is abolished in SV2A and B knockout hippocampal neurons. Panel a: Hippocampal neurons from SV2B knockout (SV2B(-/-)) mice and wild-type (WT) littermate controls were cultured. Neurons were exposed to BoNT/A (15 nM) and BoNT/B (7.5 nM) in High $K^+$ for 10 min. They were washed three times to reduce surface bound toxins, fixed and permeabilized Immunofluorescence signals for BoNT/A and B were detected and quantified, and plotted as normalized intensity ratios (% WT signals). SV2B(-/-) neurons displayed significantly reduced BoNT/A uptake (28% reduction compared to WT, P<0.0001, t-test, n=18 images). BoNT/B uptake level remained the same for SV2B(-/-) and WT neurons (P>0.05, t-test, n=22 images). Error bars represent SD. Panel b: Hippocampal neurons from littermates with the following genotypes: SV2A (+/+)SV2B(-/-), SV2A(+/+)SV2B(-/-), and double knockout SV2A(-/-)SV2B(-/-) were cultured. Cultures were exposed to BoNT/A (10 nM) and BoNT/B (7.5 nM) simultaneously for 10 min. Cells were washed three times, fixed and permeabilized. Triple immunostaining was performed (BoNT/B: rabbit anti-BoNT/B; BoNT/A: human anti-BoNT/A; SV2: mouse pan-SV2). Binding of BoNT/B to neurons was not altered between different genotypes. SV2B knockout and SV2A heterozygotes (SV2A(+/-)SV2B(-/-)) showed reduced BoNT/A binding. SV2A/B double knockouts showed no binding of BoNT/A. Panel c: Images collected in panel b were thresholded to only include neurons. The average intensity (background subtracted) was plotted as normalized data (% of SV2A(+/+)). SV2A(+/-)SV2B(-/-) neurons displayed a 53% reduction compared to SV2A(+/+)SV2B (-/-), and SV2A/B double knockouts showed no binding of BoNT/A. The binding of BoNT/B remained the same for all genotypes (P>0.05, t-test, n=11 images).

FIG. 6 shows that SV2 knockout mice have reduced BoNT/A binding at diaphragm motor nerve terminals and are more resistant to BoNT/A. Panel a: Mouse diaphragms were prepared from wild-type (WT) and SV2A(+/-)SV2B(-/-) mice. Half of the diaphragm was exposed to BoNT/A (25 nM) in stimulated conditions for 1 hr. The tissue was fixed and immunostained with α-BTX and BoNT/A antibody as described in FIG. 1a. The other half of the diaphragm was exposed to BoNT/B (25 nM), and immunostained in parallel. Representative images are shown. Panel b: Images collected in panel a were quantified as described in FIG. 1a. SV2A(+/-)SV2B(-/-) mice showed significantly less BoNT/A binding compared to WT (72% reduction, P<0.001, t-test, n=47 images), while BoNT/B binding is the same (P>0.05, t-test, n=20 images). Panel c: The susceptibility of SV2B(-/-) mice and their WT littermates to BoNT/A was determined by a rapid time-to-death assay. The same amount of BoNT/A was injected into each mouse, and their survival time (time-to-death) recorded. The average effective toxicity ($LD_{50}$/ml) were estimated from time-to-death data using a standard curve. SV2B(-/-) mice live significantly longer than WT mice (43 min versus 33 min, P<0.05, paired t-test). The effective toxicity of injected BoNT/A in WT mice is about 2.5-fold greater than SV2B knockout mice.

FIG. 7 shows that a peptide containing the BoNT/B binding site specifically inhibits BoNT/B, but not BoNT/A binding to hippocampal neurons, and SV2C-L4 does not affect BoNT/E binding. Panel a: Peptide P21 is derived from the synaptotagmin II luminal domain (Dong M et al., *J. Cell. Biol.* 162:1293-1303, 2003). P21S is a scrambled version of P21 that serves as a control (Dong M et al., supra, 2003). Cultured hippocampal neurons were exposed to BoNT/B (10 nM) and Syt $I_N$ Ab in High $K^+$ buffers for 10 min, in the presence of P21 (30 µM) or P21S. Cells were washed and fixed. Binding and uptake of Syt $I_N$ Ab and BoNT/B were analyzed through subsequent immunostaining as described in FIG. 3a. P21 inhibited BoNT/B binding to neurons, while uptake of Syt $I_N$ Ab is not affected. Panel b: Experiments were carried out as described in panel a with BoNT/A instead of BoNT/B. P21 peptide did not affect BoNT/A binding to hippocampal neurons. Panel c: Hippocampal neurons were exposed to BoNT/E (10 nM) and Syt $I_N$ Ab in High $K^+$ buffers for 10 min, in the presence of GST (10 µM) or SV2C-L4 (10 µM). Binding of BoNT/E was detected with a polyclonal anti-BoNT/E antibody. SV2C-L4 did not affect BoNT/E binding to neurons.

FIG. 9 shows an alignment of partial sequences of rat SV2C (SEQ ID NO:6), human SV2A (SEQ ID NO:14), human SV2B (SEQ ID NO:16), human SV2C (SEQ ID NO:18), mouse SV2A (SEQ ID NO:8), mouse SV2B (SEQ ID NO:10), and mouse SV2C (SEQ ID NO:12).

DETAILED DESCRIPTION OF THE INVENTION

Figure 1:
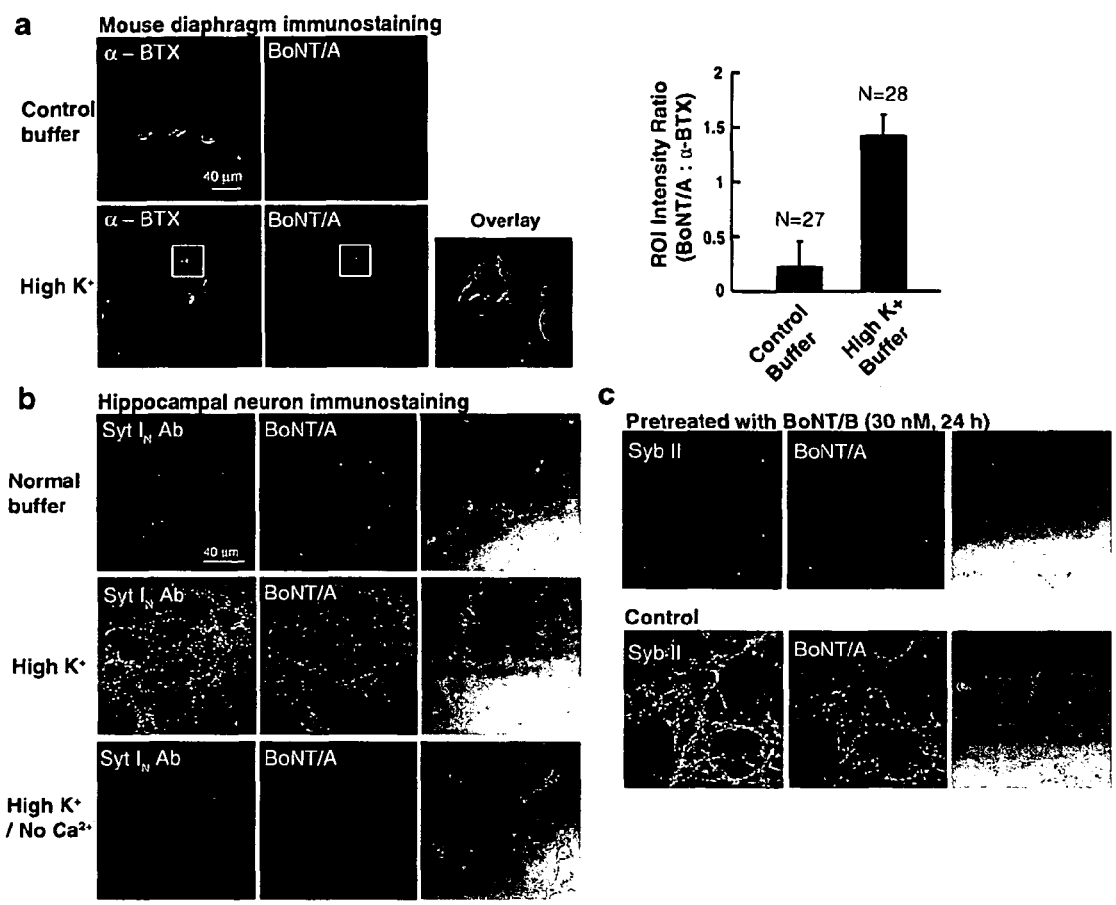
FIG. 1 shows that stimulating synaptic vesicle exocytosis increases BoNT/A binding to diaphragm motor nerve terminals and cultured hippocampal neurons. Panel a: Mouse hemi-diaphragm preparations were exposed to BoNT/A (25 nM) in either resting conditions (control buffer) or stimulated conditions (High K$^+$ buffer: 45 mM KCl). The tissue was fixed and permeabilized. Neuromuscular junctions (NMJs) were labeled with Alexa-488 conjugated α-BTX. BoNT/A was detected with a polyclonal BoNT/A antibody and a Cy3-conjugated secondary antibody. The overlay of regions indicated by rectangles was enlarged to show that BoNT/A staining mirrors α-BTX staining at individual NMJs. Right panel: BoNT/A binding to NMJs was quantified. NMJ regions (region of interest, ROI) were defined by α-BTX signals. The intensity of BoNT/A staining was normalized to α-BTX signals and the ratios were plotted on the Y-axis. Stimulation with high K$^+$ buffer resulted in an approximate 6-fold increase in BoNT/A intensity. Error bars represent SEM (n=27-28 images). Panel b: Cultured rat hippocampal neurons were exposed to BoNT/A (10 nM) and an antibody against the luminal domain of synaptotagmin I (Syt I$_N$ Ab; CI604.4, 1:40) for 1 min in three different buffer conditions: (1) Normal buffer (PBS), (2) High K$^+$ (56 mM KCl), and (3) High K$^+$/No Ca$^{2+}$ (without Ca$^{2+}$). Stimulating neurons with high K$^+$ increased Syt I$_N$ Ab immunofluorescence signals. This increase was not seen without extracellular Ca$^{2+}$. BoNT/A signals largely co-localize with Syt I$_N$ Ab signals. The third image column on the right shows images obtained from differential interference contrast microscopy (DIC). Panel c: Rat hippocampal neurons pretreated with BoNT/B (30 nM, 24 h) were exposed to BoNT/A (10 nM) for 10 min in High K$^+$ buffer. Cells were fixed and immunostained for Syb II and BoNT/A. BoNT/A binding is abolished by BoNT/B treatment, which cleaves Syb II in neurons. Neurons that were not treated with BoNT/B served as controls. The third image column on the right shows images obtained from DIC microscopy.

The present invention is based on the identification of synaptic vessel glycoprotein SV2 as the BoNT/A receptor as well as the identification of various BoNT/A-binding fragments of SV2. The disclosure here provides new prevention and treatment strategies for BoNT/A toxicity and the botulism disease. The disclosure here also provides new tools for identifying agents that can reduce SV2-BoNT/A binding, BoNT/A cellular entry, and BoNT/A toxicity.

In some species (e.g., human, rat, and mouse), three SV2 isoforms, namely SV2A, SV2B, and SV2C, have been identified. Using rat SV2 as an example, the inventors found that all three isoforms are capable of binding to and serve as the receptor for BoNT/A. In other species such as bovine and electric ray (*Discopyge ommatta*), only one isoform has been identified so far. The bovine SV2 cDNA is closer to SV2A than SV2B and SV2C, and the electric ray SV2 cDNA is closer to SV2C than SV2A and SV2B. It is known in the art that the function and amino acid sequences of SV2A, SV2B, and SV2C are conserved across animal species (mammalian species in particular). At protein level, there is at least 62% identity among known SV2 proteins (human, mouse, rat, bovine, and electric ray) and at least 57% identity among the luminal domains of known SV2 proteins. For known SV2A and bovine SV proteins, the amino acid sequence identity is over 98% for the whole protein and 100% for the luminal domain. For known SV2B proteins, the amino acid sequence identity is over 94% for the whole protein and over 96% for the luminal domain. For known SV2C and electric ray SV proteins, the amino acid sequence identity is over 79% (over 96% for mammalian species) for the whole protein and over 76% (over 97% for mammalian species) for the luminal domain. The amino acid sequence identity among rat SV2A, B, and C luminal domains is 76% and the amino acid sequence identity among mouse SV2A, B, and C luminal domains is 75%. Although the disclosure here is based on the discovery made with rat SV2A, SV2B, and SV2C, it applies to all animal species including all mammalian species. For example, while certain rat SV2C fragments have been shown to be capable of binding to BoNT/A, corresponding fragments from rat SV2A, rat SV2B as well as corresponding fragments from other SV2 homologs are expected to be capable of binding to BoNT/A. Corresponding domains and fragments among all SV2 proteins can be identified using any alignment program familiar to a skilled artisan. For example, the GCG software from Accelrys (San Diego, Calif.) can be used for this purpose (e.g., the MegaAlign program with default parameters).

An SV2 protein typically contains 12 transmembrane domains, 7 cytoplasmic domains, and one large luminal domain (luminal domain 4, L4) (Janz R and Sudhof T C, *Neuroscience* 94:1279-1290, 1999). In the case of rat SV2A, SV2B, and SV2C, the luminal domain spans from amino acid 468 to amino acid 595, amino acid 411 to amino acid 536, and amino acid 454 to amino acid 580, respectively. The inventors have determined that BoNT/A binds to an SV2 protein at its luminal domain. In particular, the inventors have demonstrated that rat SV2C luminal domain fragments amino acids 529-562 and amino acids 454-546 and various other fragments containing the above fragments are capable of binding to BoNT/A. Fragment amino acids 529-566 binds almost as efficiently as the luminal domain itself. Fragments shorter than that spanning amino acids 529-562 or 454-546 may also be able to bind to BoNT/A and a skilled artisan can readily identify these fragments by routine truncation experiments.

Furthermore, a peptide that is at least 60%, 65%, 70%, 75%, 80%, 85%, 90%, or 95% identical to any of the BoNT/A-binding fragments of an SV2 protein discussed above and any such binding fragments with one or more conservative substitutions are expected to be able to bind to BoNT/A. It is well known in the art that the amino acids within the same conservative group can typically substitute for one another without substantially affecting the function of a protein. For the purpose of the present invention, such conservative groups are set forth in Table 1 based on shared properties.

TABLE 1

| Conservative substitution. | |
|---|---|
| Original Residue | Conservative Substitution |
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr, Phe |
| Tyr (Y) | Trp, Phe, Thr, Ser |
| Val (V) | Ile, Leu, Met, Phe, Ala |

The cDNA and amino acid sequences for rat SV2A (cDNA sequence is set forth in SEQ ID NO:1 and amino acid sequence is set forth in SEQ ID NO:2), SV2B (cDNA sequence is set forth in SEQ ID NO:3 and amino acid sequence is set forth in SEQ ID NO:4), and SV2C (cDNA sequence is set forth in SEQ ID NO:5 and amino acid sequence is set forth in SEQ ID NO:6) can be found at GenBank Accession Nos. NM_057210, L10362, and NM_031593, respectively. The cDNA and amino acid sequences for mouse SV2A (cDNA sequence is set forth in SEQ ID NO:7 and amino acid sequence is set forth in SEQ ID NO:8), SV2B (cDNA sequence is set forth in SEQ ID NO:9 and amino acid sequence is set forth in SEQ ID NO:10), and SV2C (cDNA sequence is set forth in SEQ ID NO:11 and amino acid sequence is set forth in SEQ ID NO:12) can be found at GenBank Accession Nos. NM_022030, NM_153579, and XM_991257, respectively. The cDNA and amino acid sequences for human SV2A (cDNA sequence is set forth in SEQ ID NO:13 and amino acid sequence is set forth in SEQ ID NO:14), SV2B (cDNA sequence is set forth in SEQ ID NO:15 and amino acid sequence is set forth in SEQ ID NO:16), and SV2C (cDNA sequence is set forth in SEQ ID NO:17 and amino acid sequence is set forth in SEQ ID NO:18) can be found at GenBank Accession Nos. NM_014849, BCO30011, and BC100827, respectively. The cDNA and amino acid sequences for bovine SV2 (cDNA sequence is set forth in SEQ ID NO:19 and amino acid sequence is set forth in SEQ ID NO:20) can be found at GenBank Accession No. NM_173962. The cDNA and amino acid sequences for electric ray (*Discopyge ommatta*) SV2 (cDNA sequence is set forth in SEQ ID NO:21 and amino acid sequence is set forth in SEQ ID NO:22) can be found at GenBank Accession No. L23403.

Polypeptides, Nucleic Acids, Vectors, and Host Cells

The term "isolated polypeptide" or "isolated nucleic acid" used herein means a polypeptide or nucleic acid isolated from its natural environment or prepared using synthetic methods such as those known to one of ordinary skill in the art. Complete purification is not required in either case. The polypeptides and nucleic acids of the invention can be isolated and purified from normally associated material in conventional ways such that in the purified preparation the polypeptide or nucleic acid is the predominant species in the preparation. At the very least, the degree of purification is such that the extraneous material in the preparation does not interfere with use of the polypeptide or nucleic acid of the invention in the manner disclosed herein. The polypeptide or nucleic acid is preferably at least about 85% pure, more preferably at least about 95% pure and most preferably at least about 99% pure.

Further, an isolated nucleic acid has a structure that is not identical to that of any naturally occurring nucleic acid or to that of any fragment of a naturally occurring genomic nucleic acid spanning more than one gene. An isolated nucleic acid also includes, without limitation, (a) a nucleic acid having a sequence of a naturally occurring genomic or extrachromosomal nucleic acid molecule but which is not flanked by the coding sequences that flank the sequence in its natural position; (b) a nucleic acid incorporated into a vector or into a prokaryote or eukaryote genome such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of clones, e.g., as these occur in a DNA library such as a cDNA or genomic DNA library. An isolated nucleic acid can be modified or unmodified DNA or RNA, whether fully or partially single-stranded or double-stranded or even triple-stranded. A nucleic acid can be chemically or enzymatically modified and can include so-called non-standard bases such as inosine.

As used in this application, "percent identity" between amino acid or nucleotide sequences is synonymous with "percent homology," which can be determined using the algorithm of Karlin and Altschul (*Proc. Natl. Acad. Sci. USA* 87, 2264-2268, 1990), modified by Karlin and Altschul (*Proc. Natl. Acad. Sci. USA* 90, 5873-5877, 1993), or other methods familiar to a skilled artisan. The noted algorithm is incorporated into the NBLAST and XBLAST programs of Altschul et al. (*J. Mol. Biol.* 215, 403-410, 1990). BLAST nucleotide searches can be performed with the NBLAST program, score=100, wordlength=12, to obtain nucleotide sequences homologous to a polynucleotide of interest. BLAST protein searches can be performed with the XBLAST program, score=50, wordlength=3, to obtain amino acid sequences homologous to a reference polypeptide. To obtain gapped alignments for comparison purposes, Gapped BLAST can be utilized as described in Altschul et al. (*Nucleic Acids Res.* 25, 3389-3402, 1997). When utilizing BLAST and Gapped BLAST programs, the default parameters of the respective programs (e.g., XBLAST and NBLAST) can be used. An example of another program for aligning two amino acid sequences (MegaAlign, GCG) is provided earlier in the specification.

In one aspect, the present invention relates to an isolated polypeptide containing an amino acid sequence that is at least 60%, 65%, 70%, 75%, 80%, 85%, 90%, or 95% identical to that of a BoNT/A-binding fragment of an SV2 protein over the entire length of the binding fragment or an amino acid sequence of a BoNT/A-binding fragment of an SV2 protein with one or more conservative substitutions. Preferably, the above isolated polypeptide is capable of binding to BoNT/A. Specifically excluded from the polypeptide of the present invention is one that contains a full length SV2 protein. In one embodiment, an isolated polypeptide that consists of an SV2 luminal domain or that contains an SV2 luminal domain wherein the domain is flanked at one or both ends by a non-native flanking amino acid sequence is also excluded from the present invention. Examples of BoNT/A binding fragments of SV2 proteins include but are not limited to (i) amino acids 529-562 of rat SV2C, (ii) amino acids 486 to 519 of rat SV2B, (iii) amino acids 543 to 576 of rat SV2A, (iv) a fragment of a homolog of the rat SV2C, SV2B, or SV2A wherein the fragment corresponds to amino acids 529-562 of rat SV2C, amino acids 486 to 519 of rat SV2B, or amino acids 543 to 576 of rat SV2A, respectively (see FIG. 9 for examples), (v) amino acids 454-546 of rat SV2C, (vi) amino acids 411 to 503 of rat SV2B, (vii) amino acids 468 to 560 of rat SV2A, and (viii) a fragment of a homolog of the rat SV2C, SV2B, or SV2A wherein the fragment corresponds to amino acids 454-546 of rat SV2C, amino acids 411 to 503 of rat SV2B, or amino acids 468 to 560 of rat SV2A, respectively (see FIG. 9 for examples).

Preferred BoNT/A binding fragments of SV2 proteins include but are not limited to (i) amino acids 529-566 of rat SV2C, (ii) amino acids 486 to 523 of rat SV2B, (iii) amino acids 543 to 580 of rat SV2A, (iv) a fragment of a homolog of the rat SV2C, SV2B, or SV2A wherein the fragment corresponds to amino acids 529-566 of rat SV2C, amino acids 486 to 523 of rat SV2B, or amino acids 543 to 580 of rat SV2A, respectively. Other preferred BoNT/A binding fragments include the luminal domains of SV2 proteins.

In one embodiment, the polypeptide of the present invention is about the size of an SV2 luminal domain or shorter. For example, the polypeptide of the present invention can be shorter than 129, 128, 127, or 126 amino acids. In another embodiment, the polypeptide of the present invention is shorter than 125, 120, 110, 100, 90, 80, 70, 60, 50, or 40 amino acids.

In another embodiment, the polypeptide of the present invention is soluble in an aqueous solvent (e.g., water with or without other additives). By soluble in an aqueous solvent, we mean that the polypeptide exhibits a solubility of at least 10 µg/ml, preferably at least 50 µg/ml or 100 µg/ml, more preferably at least 500 µg/ml, and most preferably at least 1,000 µg/ml in an aqueous solvent. Whether a polypeptide is soluble in an aqueous solution can be readily determined by a skilled artisan based on its amino acid sequence or through routine experimentation. Examples of soluble polypeptides of the present invention include those that contain all or part of the luminal domain of an SV2 protein but lack at least part of and preferably the entire adjacent transmembrane domain(s). Soluble polypeptides are typically more suitable than insoluble polypeptides for intravenous administration.

The isolated polypeptide of the invention can include one or more amino acids at either or both N-terminal and C-terminal ends of a BoNT/A-binding sequence of an SV2 protein, where the additional amino acid(s) do not materially affect the BoNT/A binding function. Any additional amino acids can, but need not, have advantageous use in purifying, detecting, or stabilizing the polypeptide.

In order to improve the stability and/or binding properties of a polypeptide, the molecule can be modified by the incorporation of non-natural amino acids and/or non-natural chemical linkages between the amino acids. Such molecules are called peptidomimics (H. U. Saragovi et al., *Bio/Technology* 10:773-778, 1992; S. Chen et al., *Proc. Nat'l. Acad. Sci. USA* 89:5872-5876, 1992). The production of such compounds is restricted to chemical synthesis. It is understood that a polypeptide of the present invention can be modified into peptidomimics without abolishing its function. This can be readily achieved by a skilled artisan.

In another aspect, the present invention relates to an isolated nucleic acid containing a coding polynucleotide or its complement wherein the coding polynucleotide has an uninterrupted coding sequence that encodes a polypeptide of the invention as set forth above. A nucleic acid containing a polynucleotide that can hybridize to the coding polynucleotide or its complement, under either stringent or moderately stringent hybridization conditions, is useful for detecting the coding polypeptide and thus is within the scope of the present invention. Stringent hybridization conditions are defined as hybridizing at 68° C. in 5×SSC/5×Denhardt's solution/1.0% SDS, and washing in 0.2×SSC/0.1% SDS+/−100 µg/ml denatured salmon sperm DNA at room temperature, and moderately stringent hybridization conditions are defined as washing in the same buffer at 42° C. Additional guidance regarding such conditions is readily available in the art, for example, by Sambrook et al., 1989, *Molecular Cloning, A Laboratory Manual*, Cold Spring Harbor Press, N.Y.; and Ausubel et al. (eds.), 1995, *Current Protocols in Molecular Biology*, (John Wiley & Sons, N.Y.) at Unit 2.10. A nucleic acid containing a polynucleotide that is at least 80%, 85%, 90%, or 95% identical to the coding polynucleotide or its complement over the entire length of the coding polynucleotide can also be used as a probe for detecting the coding polynucleotide and is thus within the scope of the present invention. Specifically excluded from the present invention is a nucleic acid that contains a nucleotide sequence encoding a full length SV2 protein. In one embodiment, a nucleic acid that consists of a polynucleotide that encodes an SV2 luminal domain and a nucleic acid that comprises a polynucleotide that encodes a polypeptide having an SV2 luminal domain wherein the domain is flanked at one or both ends by a non-native amino acid sequence are excluded.

In a related aspect, any nucleic acid of the present invention described above can be provided in a vector in a manner known to those skilled in the art. The vector can be a cloning vector or an expression vector. In an expression vector, the polypeptide-encoding polynucleotide is under the transcriptional control of one or more non-native expression control sequences which can include a promoter not natively found adjacent to the polynucleotide such that the encoded polypeptide can be produced when the vector is provided in a compatible host cell or in a cell-free transcription and translation system. Such cell-based and cell-free systems are well known to a skilled artisan. Cells comprising a vector containing a nucleic acid of the invention are themselves within the scope of the present invention. Also within the scope of the present invention is a host cell having the nucleic acid of the present invention integrated into its genome at a non-native site.

Ligand-Polypeptide Complexes

In another aspect, the present invention relates to a complex of a ligand and a polypeptide, wherein the polypeptide comprises a member to which the ligand binds, the member being selected from (i) amino acids 529-562 of rat SV2C, (ii) amino acids 486 to 519 of rat SV2B, (iii) amino acids 543 to 576 of rat SV2A, (iv) a fragment of a homolog of the rat SV2C, SV2B, or SV2A wherein the fragment corresponds to amino acids 529-562 of rat SV2C, amino acids 486 to 519 of rat SV2B, or amino acids 543 to 576 of rat SV2A, respectively, (v) amino acids 454-546 of rat SV2C, (vi) amino acids 411 to 503 of rat SV2B, (vii) amino acids 468 to 560 of rat SV2A, (viii) a fragment of a homolog of the rat SV2C, SV2B, or SV2A wherein the fragment corresponds to amino acids 454-546 of rat SV2C, amino acids 411 to 503 of rat SV2B, or amino acids 468 to 560 of rat SV2A, respectively, (ix) an amino acid sequence that is at least 70% identical to any of the amino acid sequences in (i) to (viii) and is capable of binding to BoNT/A, and (x) an amino acid sequence from (i) to (viii) with conservative substitutions and is capable of binding to BoNT/A, with the proviso that where the polypeptide is a full length SV2 protein, the ligand is not a botulinum toxin. The complexes disclosed herein include both those formed in vitro and in vivo.

In one embodiment, the polypeptide in the complex is a full length SV2 protein.

In another embodiment, the polypeptide in the complex is one of the BoNT/A-binding polypeptides of the present invention provided in the section of "polypeptides, polynucleotides, vectors, and host cells."

In a preferred embodiment, the polypeptide in the complex comprises a member selected from (i) amino acids 529-566 of rat SV2C, (ii) amino acids 486 to 523 of rat SV2B, (iii) amino acids 543 to 580 of rat SV2A, (iv) a fragment of a homolog of the rat SV2C, SV2B, or SV2A wherein the fragment corresponds to amino acids 529-566 of rat SV2C, amino acids 486 to 523 of rat SV2B, or amino acids 543 to 580 of rat SV2A, respectively, (v) amino acids 454-546 of rat SV2C, (vi) amino acids 411 to 503 of rat SV2B, (vii) amino acids 468 to 560 of rat SV2A, and (viii) a fragment of a homolog of the rat SV2C, SV2B, or SV2A wherein the fragment corresponds to amino acids 454-546 of rat SV2C, amino acids 411 to 503 of rat SV2B, or amino acids 468 to 560 of rat SV2A, respectively.

The polypeptide in the complex may be a synthetic or recombinant peptide and it may contain an affinity tag and/or a ganglioside binding site.

In one embodiment, the ligand in the complex is an antibody against the polypeptide or a BoNT/A fragment that binds to the polypeptide. Such an antibody and BoNT/A fragment can reduces the binding between the polypeptide and BoNT/A.

Methods for Reducing BoNT/A Neuro-Toxicity

In another aspect, the present invention relates to a method for reducing BoNT/A cellular toxicity in target cells such as neurons. As a result, botulism disease can be prevented or treated. In one embodiment, the method is used to reduce BoNT/A toxicity in a human or non-human animal by administering to the human or non-human animal an agent that can reduce BoNT/A toxicity.

The term "reducing BoNT/A cellular toxicity" encompasses any level of reduction in BoNT/A toxicity. The BoNT/A toxicity can be reduced by reducing the level of an SV2 protein in target cells, by inhibiting BoNT/A-related cellular functions of an SV2 protein in target cells, or by reducing the binding between BoNT/A and an SV2 protein located on the cellular surface of target cells. The binding between BoNT/A and an SV2 protein can be reduced by either blocking the binding directly or by reducing the amount of SV2 proteins available for binding.

There are many methods by which cellular protein levels such as the level of an SV2 protein can be reduced. The present invention is not limited to a particular method in this regard. As an example, the cellular level of an SV2 protein can be reduced by using the antisense technology. For instance, a 20-25 mer antisense oligonucleotide directed against the 5' end of an SV2 mRNA can be generated. Phosphorothioate derivatives can be employed on the last three base pairs on the 3' and 5' ends of the antisense oligonucleotide to enhance its half-life and stability. A carrier such as a cationic liposome can be employed to deliver the antisense oligonucleotide. In this regard, the oligonucleotide is mixed with the cationic liposome prepared by mixing 1-alpha dioleylphatidylceltha-nolamine with dimethldioctadecylammonium bromide in a ratio of 5:2 in 1 ml of chloroform. The solvent is evaporated and the lipids resuspended by sonication in 10 ml of saline. Another way to use an antisense oligonucleotide is to engineer it into a vector so that the vector can produce an antisense cRNA that blocks the translation of an SV2 mRNA. Similarly, RNAi techniques, which are now being applied to mammalian systems, are also suited for inhibiting the expression of an SV2 protein. (See Zamore, *Nat. Struct. Biol.* 8:746-750, 2001, incorporated herein by reference as if set forth in its entirety).

Dominant Negative SV2

In another aspect, the present invention relates to identifying a dominant negative SV2 that can negate the effects of BoNT/A on cells that express the corresponding wild-type SV2. A dominant negative SV2 can be identified by introducing a mutation into a wild-type SV2 gene, expressing the mutated SV2 and the wild-type SV2 in the same host cell and determining the effect of the mutated SV2 on parameters that relate to BoNT/A toxicity, which include but are not limited to susceptibility of the host cell to BoNT/A, integration of newly formed SV2 into the host cell membrane, binding of wild-type SV2 to BoNT/A, and uptake of BoNT/A into the cells. The wild-type SV2 expressed in the host cell can be the endogenous SV2 or an SV2 introduced into the host cell. Any dominant negative SV2 identified is within the scope of the present invention. The identified dominant negative SV2 can be used to negate the effect of BoNT/A.

Blocking the Binding Between BoNT/A and SV2

The identification of SV2 as the BoNT/A receptor as well as the BoNT/A-binding sequences on SV2 enable those skilled in the art to block the binding between BoNT/A and its receptor through many strategies available in the art. One strategy involves the use of monoclonal and polyclonal antibodies specific for the BoNT/A-binding sequences on SV2. It is well within the capability of a skilled artisan to generate such monoclonal and polyclonal antibodies. The antibodies so generated are within the scope of the present invention.

Another strategy involves the use of a BoNT/A-binding polypeptide, preferably a soluble BoNT/A-binding polypeptide, to compete with the receptor for BoNT/A binding. For example, the BoNT/A-binding polypeptide of the present invention described above in the section of "polypeptides, polynucleotides, vectors, and host cells" can be employed for this purpose. Other polypeptides that can be employed include those that comprise a full length SV2 protein, those that consist of an SV2 luminal domain, and those that comprise an SV2 luminal domain wherein the domain is flanked at one or both ends by a non-native flanking amino acid sequence.

To block the binding between BoNT/A and its receptor in an animal (human or non-human), a BoNT/A-binding polypeptide from both the same and a different species can be used. The polypeptide can be introduced into the animal by administering the polypeptide directly or by administering a vector that can express the polypeptide in the animal.

Those skilled in the art understand that mutations such as substitutions, insertions and deletions can be introduced into a BoNT/A-binding sequence of an SV2 protein without abolishing their BoNT/A binding activity. Some mutations may even enhance the binding activity. A polypeptide containing such modifications can be used in the method of the present invention. Such polypeptides can be identified by using the screening methods described below.

In addition, as gangliosides may promote formation of stable BoNT/A-SV2 complexes, the binding between BoNT/A and an SV2 protein may be reduced through reducing the binding between the gangliosides and the SV2 protein or through reducing the amount of gangliosides available for binding to the SV2 protein. In a related aspect, when a BoNT/A-binding polypeptide is used for reducing BoNT/A toxicity by forming a complex with BoNT/A, gangliosides may be included to facilitate the formation of the complex.

Identifying Agents that can Block Binding Between BoNT/A and SV2

Agents that can block binding between BoNT/A and SV2 can be screened by employing BoNT/A and a polypeptide that contains a BoNT/A-binding sequence of an SV2 protein under the conditions suitable for BoNT/A to bind the polypeptide. Gangliosides are optionally included in the reaction mixture. The binding between BoNT/A and the polypeptide can be measured in the presence of a test agent and compared to that of a control that is not exposed to the test agent. A lower than control binding in the test group indicates that the agent can block binding between BoNT/A and the SV2 protein. Other BoNT/A-binding polypeptides that can be employed in the method include those of the present invention as described above in the section of "polypeptides, polynucleotides, vectors, and host cells."

There are many systems with which a skilled artisan is familiar for assaying the binding between BoNT/A and a BoNT/A-binding polypeptide. Any of these systems can be used in the screening method. Detailed experimental conditions can be readily determined by a skilled artisan. For example, the binding between BoNT/A and the polypeptide described above can be measured in vitro (cell free system). A cell culture system in which an SV2 protein is expressed and translocated onto the cellular membrane can also be used. For the cell culture system, in addition to the binding between BoNT/A and the SV2 protein, the cellular entry of BoNT/A and a number of other parameters can also be used as an indicator of binding between BoNT/A and SV2.

Any method known to one of ordinary skill in the art for measuring protein-protein interaction can be used to measure the binding between BoNT/A and a BoNT/A-binding polypeptide. Coimmunoprecipitation and affinity column isolation are two commonly used methods.

Surface plasmon resonance (SPR) is another commonly used method. SPR uses changes in refractive index to quantify binding and dissociation of macromolecules to ligands covalently linked onto a thin gold chip within a micro flow cell. This technique has been used to study protein-protein interactions in many systems, including the interactions of PA63 with EF and LF (Elliott, J. L. et al., *Biochemistry* 39:6706-6713, 2000). It provides high sensitivity and accuracy and the ability to observe binding and release in real time. Besides the equilibrium dissociation constant (Kd), on- and off-rate constants (ka and kd) may also be obtained. Typically, a protein to be studied is covalently tethered to a carboxymethyl dextran matrix bonded to the gold chip. Binding of a proteinaceous ligand to the immobilized protein results in a change in refractive index of the dextran/protein layer, and this is quantified by SPR. A BIAcore 2000 instrument (Pharmacia Biotech) can be used for these measurements.

For the cell culture system, the binding of BoNT/A to a BoNT/A-binding polypeptide can be assayed by staining the cells, the examples of which are described in the example section below.

Identifying Agents that can Bind to a BoNT/A-Binding Sequence of SV2

Agents that can bind to a BoNT/A-binding sequence of an SV2 protein can be used to block the binding between BoNT/A and the SV2 protein. Such agents can be identified by providing a polypeptide that contains a BoNT/A-binding sequence of an SV2 protein to a test agent, and determining whether the agent binds to the BoNT/A-binding sequence. Other BoNT/A-binding polypeptides that can be employed in the method include those of the present invention as described above in the section of "polypeptides, polynucleotides, vectors, and host cells." Any agent identified by the method can be further tested for the ability to block BoNT/A entry into cells or to neutralize BoNT/A toxicity. A skilled artisan is familiar with the suitable systems that can be used for the further testing. Examples of such systems are provided in the example section below.

The skilled artisan is familiar with many systems in the art for assaying the binding between a polypeptide and an agent. Any of these systems can be used in the method of the present invention. Detailed experimental conditions can be readily determined by a skilled artisan. For example, a polypeptide that contains a BoNT/A-binding sequence of an SV2 protein can be provided on a suitable substrate and exposed to a test agent. The binding of the agent to the polypeptide can be detected either by the loss of ability of the polypeptide to bind to an antibody or by the labeling of the polypeptide if the agent is radioactively, fluorescently, or otherwise labeled. In another example, a polypeptide that contains a BoNT/A-binding sequence of an SV2 protein can be expressed in a host cell, and the cell is then exposed to a test agent. Next, the polypeptide can be isolated, e.g., by immunoprecipitation or electrophoresis, and the binding between the polypeptide and the agent can be determined. As mentioned above, one way to determine the binding between the polypeptide and the agent is to label the agent so that the polypeptide that binds to the agent becomes labeled upon binding. If the test agent is a polypeptide, examples of specific techniques for assaying protein/protein binding as described above can also be used. It should be noted that when a BoNT/A-binding sequence of an SV2 protein used in the screening assay have flanking sequences, it may be necessary to confirm that an agent binds to the BoNT/A-binding sequence rather than the flanking sequences, which can be readily accomplished by a skilled artisan.

Agents that can be Screened

The agents screened in the above screening methods can be, for example, a high molecular weight molecule such as a polypeptide (including, e.g., a polypeptide containing a modified BoNT/A-binding sequence of an SV2 protein, or a monoclonal or polyclonal antibody against a BoNT/A-binding sequence of an SV2 protein), a polysaccharide, a lipid, a nucleic acid, a low molecular weight organic or inorganic molecule, or the like.

Batteries of agents for screening are commercially available in the form of various chemical libraries including peptide libraries. Examples of such libraries include those from ASINEX (i.e. the Combined Wisdom Library of 24,000 manually synthesized organic molecules) and CHEMBRIDGE CORPORATION (i.e. the DIVERSet™ library of 50,000 manually synthesized chemical compounds; the SCREEN-Set™ library of 24,000 manually synthesized chemical compounds; the CNS-Set™ library of 11,000 compounds; the Cherry-Pick™ library of up to 300,000 compounds) and linear library, multimeric library and cyclic library (Tecnogen (Italy)). Once an agent with desired activity is identified, a library of derivatives of that agent can be screened for better molecules. Phage display is also a suitable approach for finding novel inhibitors of the interaction between BoNT/A and SV2.

Methods of Detecting BoNT/A or *Clostridium botulinum*

In another aspect, the present invention relates to a method of detecting BoNT/A or *Clostridium botulinum*. The method involves exposing a sample suspected of containing BoNT/A to an agent that contains a polypeptide having a BoNT/A-binding sequence of an SV2 protein, and detecting binding of the polypeptide to BoNT/A. Other BoNT/A-binding polypeptides that can be employed in the method include those of the present invention as described above in the section of "polypeptides, polynucleotides, vectors, and host cells."

Methods for Identifying Polypeptides that can Bind to BoNT/A

In another aspect, the present invention relates to a method for identifying polypeptides that can bind to BoNT/A. The method involves providing a polypeptide that comprises a BoNT/A-binding sequence of an SV2 protein, modifying the polypeptide at the BoNT/A-binding sequence, and determining whether the modified polypeptide can bind to BoNT/A.

Kits

Any product of the invention described herein can be combined with one or more other reagent, buffer or the like in the form of a kit (e.g., a diagnosis, prevention, or treatment kit) in accord with the understanding of a skilled artisan.

The invention will be more fully understood upon consideration of the following non-limiting example.

Example

In this example, we demonstrate that BoNT/A binds to all three SV2 isoforms (SV2A, SV2B, and SV2C). Particular binding fragments such as amino acids 529-562, 529-566, and 454-546 of the rat SV2C were also identified. Recombinant SV2 fragments inhibit BoNT/A binding to hippocampal neurons and motor nerve terminals. Significantly, BoNT/A binding to hippocampal neurons was abolished in SV2A/B knockout mice and this binding can be restored by transfecting neurons with SV2. Consistently, BoNT/A binding was reduced at diaphragm motor nerve terminals in SV2 knockout mice, and SV2B knockout mice displayed reduced sensitivity to BoNT/A. These data establish SV2 as the protein receptor for BoNT/A, which mediates toxin entry through synaptic vesicle recycling.

Materials and Methods

Materials, Antibodies and SV2 Knockout Mouse Lines:

Alexa 488-conjugated α-BTX was purchased from Molecular Probes, Inc. (OR). A mAb that recognizes SNAP-25 after it has been cleaved by BoNT/A (anti-SNAP-25-C) was purchased from Research & Diagnostic Antibodies, Inc. (CA). mAbs directed against SV2 (pan-SV2), Syp (Cl7.2), Syb II (Cl69.1) and Syt I (Syt $I_N$ Ab, Cl604.4) were generously provided by R. Jahn (Max-Planck-Institute for Biophysical Chemistry, Gottingen, Germany). A human antibody directed against BoNT/A (RAZ-1) was generously provided by J. Marks (University of California—San Francisco, Calif.). Cy2, Cy3, Cy5, Alexa 546 and Alexa 647 conjugated secondary antibodies were purchased from Jackson Laboratories (ME) and Molecular Probes, Inc. Rabbit polyclonal anti-BoNT/A, B and E antibodies and anti-SV2A, B and C antibodies were described in Dong M et al., *J. Cell. Biol.* 162:1293-1303, 2003; and Janz R and Sudhof T C, *Neuroscience* 94:1279-1290, 1999, both are herein incorporated by reference in their entirety). BoNT/A, B and E were purified as described in Malizio C G, Methods and Protocols, O. Hoist, ed. (Humana Press), pp. 27-39, 2000, which is incorporated by reference in its entirety. A mixture of bovine brain gangliosides was purchased from Matreya LLC (PA). The SV2 knockout mouse lines used in this study were described in Janz R et al., *Neuron* 24:1003-1016, 1999, which is incorporated by reference in its entirety. Mice were genotyped by PCR as described in Janz R et al., supra, 1999.

cDNA, Constructs and Transfection:

Rat SV2A, B and C cDNAs were described in Bajjalieh S M et al. *Science* 257: 1271-3, 1992; Feany M B et al. *Cell* 70: 861-7, 1992; Bajjalieh S M et al. *Proc Natl Acad Sci USA* 90: 2150-4, 1993; and Janz R & Sudhof T C *Neuroscience* 94: 1279-90, 1999, all of which are herein incorporated by reference in their entirety. Various SV2 luminal domain fragments were generated by PCR, subcloned into pGEX-2T and purified as GST fusion proteins (Lewis J L et al. *J Biol Chem* 276: 15458-65, 2001). GST and GST tagged SV2C-L4 proteins were also purified using magnetic GST beads according to the manufacturers protocol (Promega, Wis.), eluted with 40 mM Glutathione (Sigma), and subsequently dialyzed to produce high concentrations of soluble protein.

To transfect hippocampal neurons with SV2 isoforms, full length SV2A, B and C were subcloned into the Lox-Syn-Syn lentivirus vector (provided by P. Scheiffele, Columbia University, NY). This vector is a modified version of pFUGW (Lois C et al., *Science* 295:868-872, 2002) and contains separate neuronal-specific (synapsin) promoters. One promoter controls the expression of SV2 isoforms inserted between BamHI and NotI sites and the other promoter controls expression of EGFP to detect transfected cells. Transfections were performed on neurons 7-10 DIV using Lipofectamine 2000 (Invitrogen) as described in Dean C et al., *Nat. Neurosci.* 6:708-716, 2003 (incorporated by reference in its entirety) and analyzed 48 hrs later. Note: The BamHI site inside the SV2C sequence has been mutated (GGATCC to GGATAC, preserving the amino acid sequence) to simplify subcloning.

Neuronal Cell Cultures, BoNT Uptake, Immunocytochemistry:

Cultures of hippocampal neurons were prepared from E18-19 rats, and SV2 knockout mouse neuron cultures were prepared from P1 mice. Neurons were plated on poly-D-lysine coated glass coverslips (12 mm) at a density of 50,000/cm$^2$ and cultured in Neurobasal medium supplemented with B-27 (2%) and Glutamax (2 mM). Experiments were carried out on neurons 10-14 days old.

To assay for BoNT/A uptake under different conditions (FIG. 1b), hippocampal neurons were incubated in one of the following assay buffers (200 μl) containing BoNT/A (10 nM) and Syt $I_N$ Ab (604.4, 1:40) for 1 min. These buffers are: control buffer (PBS: 140 mM NaCl, 3 mM KCl, 1.5 mM KH$_2$PO$_4$, 8 mM Na$_2$HPO$_4$, 1 mM CaCl$_2$, 0.5 mM MgCl$_2$), high K$^+$ (same as control buffer but adjusted to 56 mM KCl and 87 mM NaCl), and high K$^+$/No Ca$^{2+}$ buffer (same as high K$^+$ buffer but lacking CaCl$_2$). Neurons were then washed in PBS (3×500 μl) and fixed in 4% paraformaldehyde for 15 min. After permeabilization with 0.3% Triton X-100, neurons were blocked with 10% goat serum and stained with a polyclonal anti-BoNT/A antibody (1:200) for 1 hr at room temperature. The secondary antibodies were Cy2-conjugated goat-anti-mouse and Cy3-conjugated goat-anti-rabbit Immunofluorescence images were acquired using a confocal microscope (Olympus FV1000, 60× water-immersion objective). Identical gain and laser settings were used for images that were directly compared in the figures. For all experiments using hippocampal neurons after FIG. 1b, neurons were incubated in high K$^+$ buffer for 10 min in order to increase the amount of toxin entry.

For triple staining of BoNT/A, BoNT/B and SV2 (FIG. 4b), BoNT/B was detected with a rabbit polyclonal antibody (1:200) and a Cy2-conjugated secondary antibody; BoNT/A was detected with a human antibody (RAZ-1, 1:300) and Alexa-546 conjugated secondary antibody; and SV2 expression was detected with a mouse monoclonal antibody (pan-SV2 Ab, 1:400), and Alexa-647 conjugated secondary antibody.

To detect SNAP-25 that has been cleaved by BoNT/A (FIG. 3b), neurons were washed three times after exposure to BoNT/A, and further incubated in culture media for 6 hrs. Cells were then fixed, permeabilized, and stained with the anti-SNAP-25-C monoclonal antibody (1:50) and the rabbit anti-BoNT/A antibody.

Figure 4:
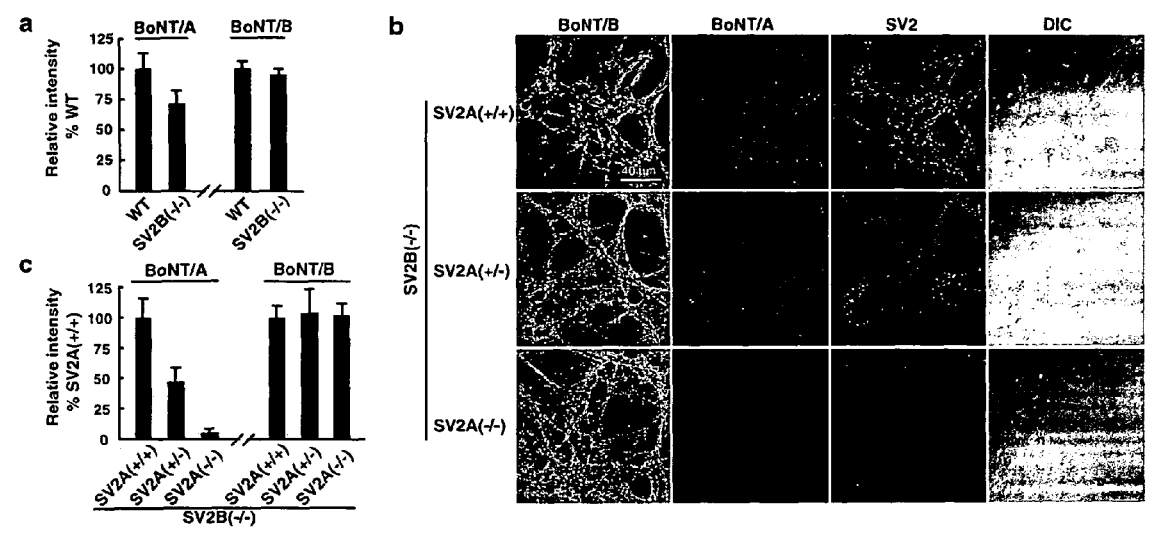

ImageJ software (NIH) was used to quantify fluorescence intensities shown in FIG. 4. Briefly, a fixed threshold was first chosen for each channel (BoNT/B and BoNT/A) to exclude background signals from regions lacking neurons, and the average intensity of the fluorescence signals from decorated neurons was measured. Neurons that were not exposed to BoNT/A and B were fixed and stained with the same antibodies in parallel. The average intensity of these images was subtracted from samples treated with the toxins. Two-tailed t tests were used to determine statistical significance.

Co-Immunoprecipitation and Pull-Down Assays:

Rat or mice brain detergent extracts were made as described in Lewis J L et al., *J. Biol. Chem.* 276:15458-15465, 2001, which is incorporated by reference in its entirety. BoNT/A was premixed with brain extracts (400 μl, 3-6 mg/ml) for 1 hr at 4° C. before adding antibodies (5 μl), and then further incubated for 1 hr. Protein G Fast Flow beads (40 μl, Amersham Biosciences) were added and incubated for 1 hr. Beads were washed three times in TBS (20 mM Tris, 150 mM NaCl, pH 7.4) plus 0.5% Triton X-100. Bound material was subjected to SDS-PAGE and western blot analysis.

Recombinant GST fusion proteins were purified and immobilized on glutathione-Sepharose beads. Pull down assays were carried out as described in Dong M et al. (supra, 2003), using 8 μg immobilized proteins and 100 nM toxins in 100 μl TBS plus 0.5% Triton X-100. Bound material was subjected to SDS-PAGE and western blot analysis.

Mouse Hemi-Diaphragm Experiments:

Mouse hemi-diaphragms were kept in either control buffer (FIG. 1a, mammalian Ringer, in mM: NaCl 138.8, KCl 4, NaHCO$_3$ 12, KH$_2$PO$_4$ 1, MgCl$_2$ 2, CaCl$_2$ 2, and glucose 11), or high K$^+$ buffer (same as control buffer but adjusted to 98 mM NaCl and 45 mM KCl), warmed to 37° C. and gased with 95% O$_2$/5% CO$_2$. Hemi-diaphragms were incubated with the indicated BoNTs (25 nM) for 1 hr at room temperature (note: 10 nM BoNT/A was used and incubated for only 30 min in FIG. 3c). After incubation, diaphragms were washed and fixed with 4% paraformaldehyde for 30 min at room temperature, permeabilized and blocked in 5% goat serum plus 0.5% Triton X-100. Diaphragms were incubated with Alexa-488-conjugated α-BTX (1:250) and rabbit anti-BoNT/A or B antibodies (1:1000) at 4° C., overnight. A Cy3-conjugated anti-rabbit secondary antibody was used at a dilution of 1:800. For staining SV2A, B or C in the NMJ (FIG. 8), the hemi-diaphragms were excised and immediately fixed. A 1:1000 dilution of the specific rabbit anti-SV2A, B or C antibodies were used. All images were collected using a confocal microscope (Olympus FV1000, 60× water-immersion objective).

To quantify fluorescent signals, the α-BTX channel was pseudo-colored green and BoNT/A (or BoNT/B) channel was pseudo-colored red. Merged green and red images were imported into MetaMorph software (Improvision). The regions of interests (ROI) marking NMJs were determined by thresholding the α-BTX green channel. The same threshold values were used throughout the diaphragm experiments. The average intensity of green and red channels within ROIs were measured and the ratio between them used to determine the level of toxin binding. Two-tailed t tests were used to determine statistical significance between pairwise sets of data.

Rapid BoNT Toxicity Assay in Mice:

BoNT/A effective toxicity in mice was estimated using the intravenous method described in Boroff D A and Fleck U, *J. Bacteriol.* 92:1580-1581, 1966 (incorporated by reference in its entirety); Dong M et al., supra, 2003; and Malizio C G, supra, 2000. Briefly, BoNT/A (type A1) isolated from Hall strain was diluted to 10 μg/ml in 30 mM sodium phosphate buffer (pH 6.3 plus 0.2% gelatin). Each mouse was injected intravenously (lateral tail vein) with 0.1 ml of the diluted toxin and their time-to-death was recorded. The time-to-death values were converted to intraperitoneal LD$_{50}$/ml using a standard curve described in Malizio C G, supra, 2000. SV2B knockout mice used in these experiments had been crossed for 6 generation against C57B16/J mice.

Results

The BoNT/A Receptor Resides on Synaptic Vesicles:

The physiological target for BoNT/A is peripheral motor nerve terminals (Dolly J O et al., Nature 307:457-460, 1984). Stimulation of neuronal activity (i.e. neurotransmitter release) can accelerate the rate of paralysis caused by BoNT/A (Hughes R W, *J. Physiol.* (Lond.) 160:221-233, 1962). However, it is not known whether synaptic vesicle exocytosis directly increases BoNT/A binding and entry into neurons. To address this question, we visualized BoNT/A binding to motor nerve terminals in mouse diaphragm preparations. The neuromuscular junctions (NMJs) in this tissue were labeled with α-bungarotoxin (α-BTX), which binds to postsynaptic acetylcholine receptors (Astrow S H et al., *J. Neurosci.* 12:1602-1615, 1992). As shown in FIG. 1*a*, high $K^+$ solution (45 mM KCl), which triggers synaptic vesicle exocytosis, increased BoNT/A binding to NMJs by approximately 6-fold compared to control conditions, indicating that synaptic vesicle exocytosis exposes BoNT/A receptors.

To further analyze whether the BoNT/A receptor is on synaptic vesicles, we used cultured rat hippocampal neurons as a model system. Synaptic vesicle recycling was monitored through the uptake of an antibody that recognizes the luminal domain of synaptotagmin I (Syt $I_N$ Ab) (Dong M et al., *J. Cell. Biol.* 162:1293-1303, 2003), an abundant synaptic vesicle membrane protein. As shown in FIG. 1*b*, uptake of Syt $I_N$ Ab was greatly increased by a short stimulation with high $K^+$ (56 mM KCl, 1 min), and inhibited by depletion of extracellular $Ca^{2+}$. Interestingly, uptake of BoNT/A to the same neurons mimicked Syt $I_N$ Ab behavior and largely co-localize with Syt $I_N$ Ab signals (FIG. 1*b*). To further confirm this finding, we pretreated these neurons with BoNT/B, which specifically blocks synaptic vesicle exocytosis by cleaving Syb II, a synaptic vesicle membrane protein required for exocytosis (Schiavo G et al., Nature 359:832-835, 1992). As shown in FIG. 1*c*, BoNT/B treatment abolished uptake of BoNT/A under stimulated conditions, indicating that the BoNT/A receptor resides on vesicles containing Syb II in neurons. Together, these evidences suggest that the receptor for BoNT/A is on synaptic vesicles.

BoNT/A binds to the luminal domain of SV2: Synaptic vesicles are well-studied organelles, and most, if not all, integral synaptic vesicle proteins have been identified (Fernandez-Chacon R and Sudhof T C *Ann. Rev. Physiol.* 61:753-776, 1999). We screened known synaptic vesicle membrane proteins for BoNT/A interactions by using their specific antibodies to co-immunoprecipitate BoNT/A from rat brain detergent extracts. As shown in FIG. 2*a*, an SV2 monoclonal antibody (pan-SV2) was able to immunoprecipitate BoNT/A. This interaction is specific since an antibody against synaptophysin (Syp), another abundant vesicle protein, failed to pull down significant amounts of BoNT/A (FIG. 2*a*).

We next assessed whether BoNT/A-SV2 interactions are affected by gangliosides. We increased ganglioside concentration in brain detergent extracts by adding exogenous gangliosides. Immunoprecipitations were performed at various BoNT/A concentrations. As indicated in FIG. 2*b*, adding exogenous gangliosides increased the level of co-immunoprecipitation of BoNT/A. This effect was not significant at high BoNT/A concentration (100 nM), but became more apparent at low toxin concentration (e.g., 20 nM), indicating gangliosides may promote formation of stable BoNT/A-SV2 complexes at low toxin concentration.

SV2 is a conserved membrane protein on synaptic vesicles and endocrine secretory vesicles in vertebrates (Buckley K and Kelly R B, *J. Cell. Biol.* 100:1284-1294, 1985; Lowe A W et al., *J. Cell. Biol.* 106:51-59, 1988). Three highly homologous isoforms have been identified, denoted as SV2A, B and C (Bajjalieh S M et al., *Proc. Natl. Acad. Sci. USA* 90:2150-2154, 1993; Bajjalieh S M et al., *Science* 257:1271-1273, 1992; Feany M B et al., Cell 70:861-867, 1992; Janz R and Sudhof T C, *Neuroscience* 94:1279-1290, 1999). SV2A and B are widely expressed throughout the brain, while the expression of SV2C is more restricted to evolutionarily older brain regions (Bajjalieh S M et al., *J. Neurosci.* 14:5223-5235, 1994; Janz R and Sudhof T C, supra, 1999). The antibody used in FIG. 2*a* recognizes all three isoforms (Lowe A W et al., supra, 1988). As depicted in FIG. 2*d*, SV2 isoforms share a similar topology, containing 12 putative transmembrane domains and only one relatively large luminal domain (luminal domain 4, L4) (Janz R and Sudhof T C, supra, 1999). Because the luminal domain of SV2 is the only region exposed to the outside of cells after vesicle exocytosis, we first examined whether BoNT/A binding is mediated by SV2 luminal domains. The major luminal domain (L4) of SV2A, B and C were purified as GST fusion proteins, immobilized on beads and tested for their ability to pull down BoNT/A, B and E from solution. As shown in FIG. 2c, we observed direct binding of BoNT/A, but not BoNT/B or E, to all SV2 isoforms. SV2C showed the most robust binding, and SV2B pulled down the least amount of BoNT/A.

To determine the critical BoNT/A binding region, we made a series of truncation mutants within the SV2C-L4 region. As shown in FIG. 2e, a short fragment (amino acids 529-566) was able to pull down similar levels of BoNT/A to the full L4 region. Sequence alignment showed that this region, indicated in FIG. 2d by arrows, is relatively conserved among SV2 isoforms and includes two putative N-glycosylation sites. It was further observed that a shorter fragment, amino acids 529-562, was also able to pull down BoNT/A, although not as effectively as the 529-566 fragment. In addition, various fragments containing amino acids 454-546 were also able to pull down BoNT/A.

Figure 3:
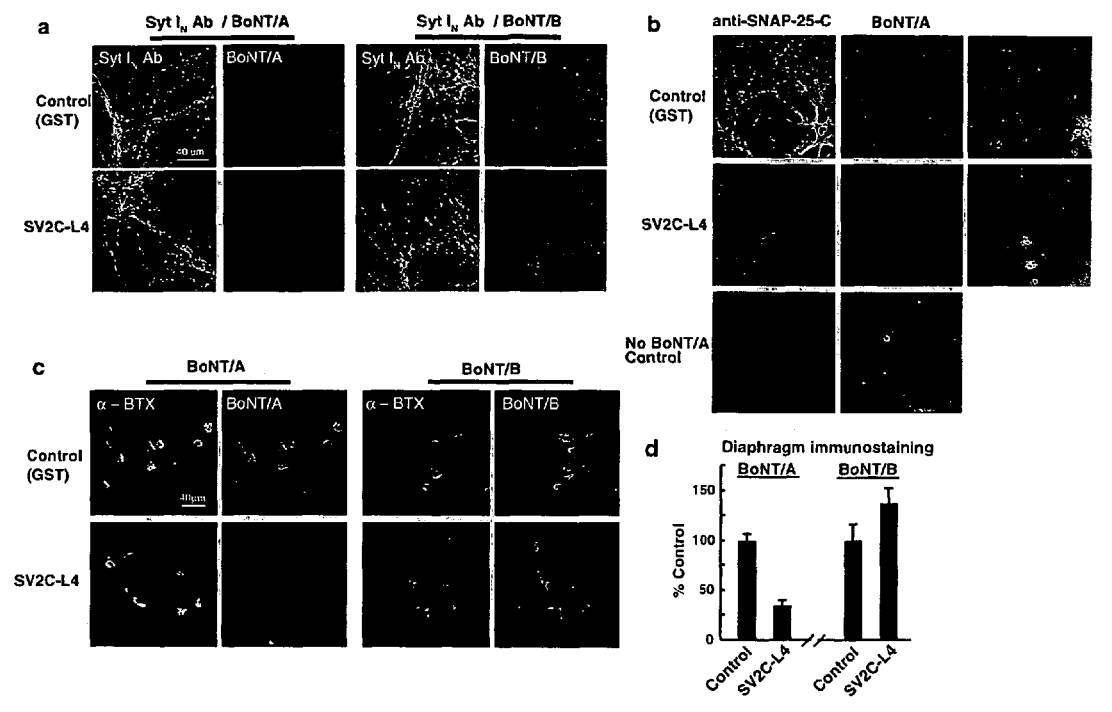

SV2C luminal fragments inhibit BoNT/A binding to neurons: Among the three SV2 isoforms, hippocampal neurons were found to express SV2A and B, but not SV2C (Bajjalieh S M et al., supra, 1994; Janz R and Sudhof T C, supra, 1999). To determine whether SV2 mediates BoNT/A binding in these neurons, we used soluble recombinant SV2C-L4 fragments, which showed the highest apparent affinity for BoNT/A, to inhibit BoNT/A binding to neurons by competing with endogenous SV2A/B. Neurons were exposed to BoNT/A and Syt $I_N$ Ab for 10 min in the presence of an excess amount of either control protein (GST) or GST-tagged SV2C-L4 fragment. As shown in FIG. 3a, SV2C-L4 reduced BoNT/A binding to neurons compared to GST. Neurons in both conditions showed similar level of Syt $I_N$ Ab uptake, indicating that the reduction in BoNT/A binding is not due to nonspecific changes in synaptic vesicle recycling.

Figure 7:
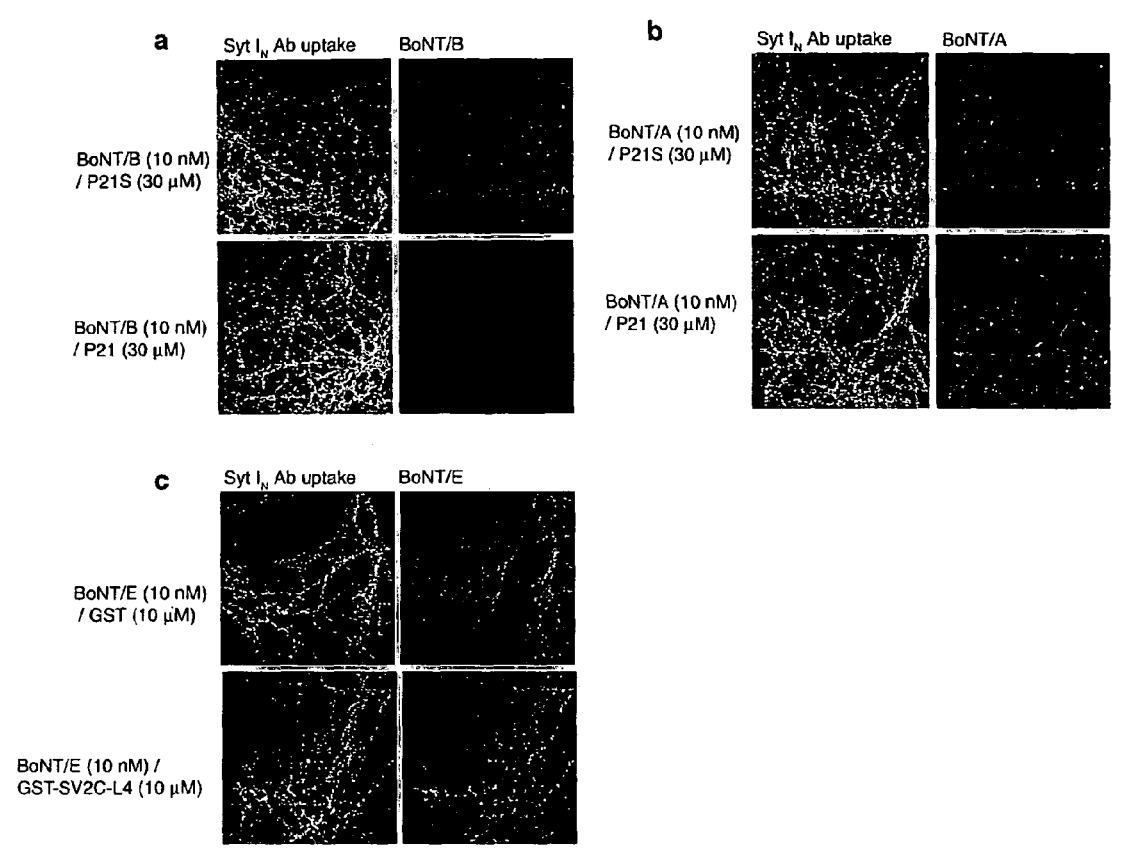

To further demonstrate the specificity of this inhibition, we tested in parallel another BoNT, BoNT/B, which has been shown to use the synaptic vesicle protein synaptotagmin I/II to enter cells (Dong M et al., supra, 2003; Nishiki T et al., *J. Biol. Chem.* 269:10498-10503, 1994; Nishiki T et al., *Biochim. Biophys. Acta* 1158:333-338, 1993). BoNT/B is an ideal control since it has similar structure and size to BoNT/A and uses the same entry pathway. As shown in FIG. 3a (right panel), SV2C-L4 did not affect BoNT/B binding to neurons. Furthermore, binding of BoNT/B can be inhibited by adding a peptide (P21) derived from its receptor, synaptotagmin II (Syt II) (Dong M et al., supra, 2003), and addition of this peptide did not affect BoNT/A binding (FIGS. 7a and b). Interestingly, SV2C-L4 also did not affect the binding of BoNT/E, another major BoNT, suggesting BoNT/E does not use SV2 to enter neurons (FIG. 7c).

We further assessed whether the reduction in BoNT/A binding by addition of SV2C-L4 correlates with the protection of endogenous SNAP-25. Taking advantage of a specialized antibody, anti-SNAP-25-C, which only recognizes SNAP-25 fragments cleaved by BoNT/A (FIG. 3b), we monitored the level of cleaved fragments by immunostaining Neurons were first treated with BoNT/A for 10 min in the presence of either GST or SV2C-L4. These neurons were washed and further incubated for 6 hrs, fixed and immunostained for cleaved SNAP-25 fragments. As shown in FIG. 3b, reduced BoNT/A binding by addition of SV2C-L4 resulted in decreased levels of SNAP-25 cleavage, indicating that SV2C-L4 prevented the functional entry of BoNT/A into neurons.

Figure 8:
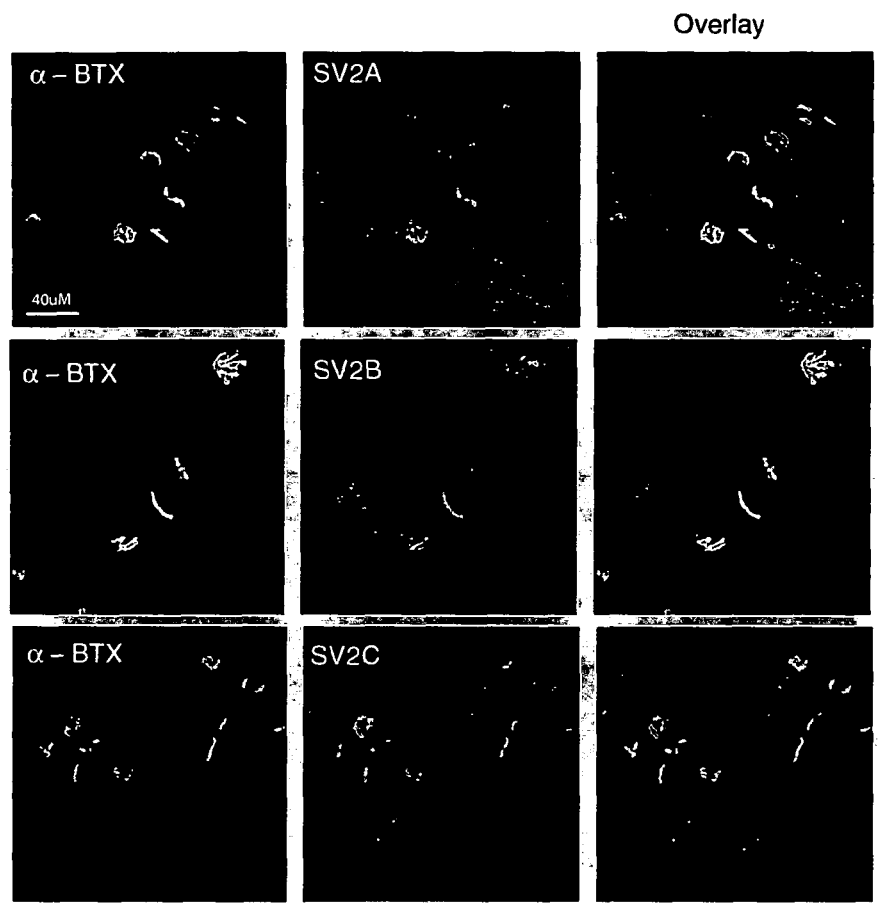
FIG. 8 shows that motor nerve terminals at mouse diaphragm express SV2A, B and C. Mouse hemi-diaphragms were excised, immediately fixed in 4% paraformaldehyde for 30 min, permeabilized, and blocked. Expression of SV2A, B or C was detected by their specific polyclonal antibodies (1:1000). NMJs were labeled with α-BTX. All SV2 isoforms were observed at NMJs, presumably at presynaptic nerve terminals.

We extended this study to peripheral motor nerve terminals, the physiological target of BoNT/A in vivo. Using SV2 isoform specific antibodies, we found that motor nerve terminals at NMJs in the diaphragm express all three SV2 isoforms (FIG. 8). Pre-incubation of BoNT/A with a high concentration of SV2C-L4 fragments (30 µM) significantly reduced BoNT/A binding to NMJs (65% reduction compared to control, P<0.0001, t-test) (FIGS. 3c and d). This decrease is specific to BoNT/A since SV2C-L4 did not affect BoNT/B binding (FIGS. 3c and d). These data suggest that binding of BoNT/A to motor nerve terminals is mediated by direct interactions with SV2 luminal domains.

BoNT/A binding is abolished in SV2A/B knockout neurons: To determine definitively whether SV2 is the receptor for BoNT/A, we turned to available SV2A and B single knockout and SV2A/B double knockout mice (Janz R et al., *Ann. NY Acad. Sci.* 733:345-255, 1999). Mice lacking SV2A (SV2A single knockout and SV2A/B double knockout) display severe seizures and die within 2-3 weeks of birth, while SV2B single knockout mice are normal. These phenotypes may be because SV2A has wider distribution than SV2B and these two isoforms are functionally redundant (Janz R et al., supra, 1999). Cultured hippocampal neurons from SV2A/B knockout mice develop normal synaptic structures and are capable of releasing neurotransmitter (Janz R et al., supra, 1999). Because these neurons only express SV2A and B, neurons from SV2A/B double knockout mice become an ideal loss-of-function model to study the role of SV2 for BoNT/A binding.

We first tested the function of SV2B by comparing BoNT/A binding to neurons from SV2B knockout (SV2B (−/−)) mice and wild-type littermate controls (WT). Neurons were exposed to BoNT/A and B simultaneously for 10 min in High K$^+$ buffer, washed and fixed. Binding of BoNT/A and B to neurons was quantified by measuring immunofluorescence intensity (see Methods for details). Normalized average intensities (% WT) are shown in FIG. 4a. SV2B knockout neurons showed significantly reduced BoNT/A binding (28% reduction compared to WT, P<0.0001, t-test), while BoNT/B binding remained the same. These data suggest that lack of SV2B does not affect the toxin entry pathway—synaptic vesicle recycling—in general, but rather specifically reduced BoNT/A binding surface binding sites.

Because SV2B(−/−) neurons still express SV2A, we asked whether remaining binding of BoNT/A is mediated by SV2A. By breeding SV2A(+/−)SV2B(−/−) mice, we generated littermates that have no SV2B but wild-type levels of SV2A (SV2A(+/+)SV2B(−/−)), no SV2B and half the levels of SV2A (SV2A(+/−)SV2B(−/−)), and SV2A/B double knockouts (SV2A(−/−)SV2B(−/−)) (FIG. 4b). Neurons cultured from these littermates were exposed to BoNT/A and B, washed and fixed. Triple immunostaining of BoNT/A, BoNT/B and SV2 were performed and representative images from each genotype are shown in FIG. 4b. Quantification of immunofluorescence intensity showed that BoNT/A binding to SV2A(+/−) SV2B(−/−) neurons is only 47% of SV2A(+/+) SV2B(−/−) neurons (FIG. 4c). Interestingly, the majority of BoNT/A binding in SV2A(+/−)SV2B(−/−) neurons colocalized with SV2A expression (FIG. 4b middle frames). Strikingly, there is virtually no binding of BoNT/A to SV2A/B double knockout neurons (FIGS. 4b and c). These changes in binding are specific to BoNT/A, since BoNT/B binding to each genotype remained the same (FIGS. 4b and c). This indicates that SVA/B knockouts specifically abolished BoNT/A recognition sites instead of causing other entry pathway defects. Together with the fact that SV2C luminal fragments were able to inhibit BoNT/A binding, we have established that BoNT/A binding to hippocampal neurons is mediated by direct interactions with SV2A and B.

Figure 5:
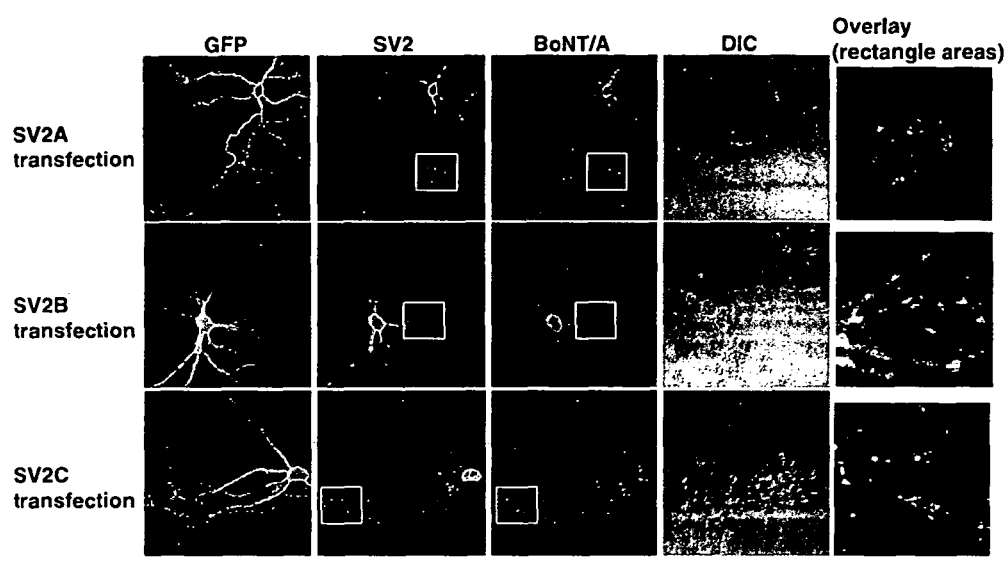
FIG. 5 shows that introducing SV2A, B or C in SV2A/B double knockout neurons rescues BoNT/A binding. Rat SV2A, B and C were subcloned into a lentiviral vector under control of a neuronal specific synapsin promoter, and were used to transfect hippocampal neurons from SV2A/B double knockout mice. Forty-eight hrs after transfection, neurons were exposed to BoNT/A (10 nM) for 10 min. Cells were washed three times, fixed, and permeabilized Immunostaining for SV2 and BoNT/A were performed as described in FIG. 4b. Transfected neurons were identified by GFP expression, which is under control of a separated synapsin promoter in the vector. Expression of exogenous un-tagged SV2 isoforms were confirmed by SV2 staining, and BoNT/A selectively bound to transfected cells. The overlay images of regions indicated by white rectangles are enlarged to show the high degree of colocalization between SV2 expression and BoNT/A signals.

Expression of SV2 Restores BoNT/A Binding to SV2A/B Knockout Neurons:

Using hippocampal neurons from SV2A/B double knockout mice, we carried out rescue studies to determine whether expression of SV2A, B or C can restore BoNT/A binding. Rat SV2A, B or C were transfected into these neurons, with a lentiviral vector that can express SV2 and GFP simultaneously under separated neuronal specific promoters (synapsin promoter, details described in Methods). Forty eight hrs post-transfection, neurons were exposed to BoNT/A for 10 min, washed, and binding of BoNT/A assessed by immunostaining Transfected neurons were identified by GFP fluorescence signals and expression of SV2 in these neurons were confirmed by immunostaining. As shown in FIG. 5, BoNT/A binding was only observed on neurons transfected with SV2A, B or C, while other neurons in the same field showed no binding. Enlarged overlay images between SV2 and BoNT/A signals showed a high degree of colocalization at synapses (FIG. 5, overlay). The high level of SV2 expression in the cell soma is likely due to over-expression of exogenous proteins since it is not found in immunostaining of endogenous SV2 in wild-type neurons. Overexpression of another synaptic vesicle protein, synaptotagmin I, using the same viral vector did not resulted in detectable BoNT/A fluorescence signals, confirming the specificity of the rescue effect. SV2A, B or C all rescued BoNT/A binding, indicating all three isoforms can mediate BoNT/A binding to neurons once expressed.

BoNT/A Binding to Motor Terminals is Reduced in SV2A/B Knockout Mice:

To determine whether SV2 function as a receptor for BoNT/A at its physiological target, we examined BoNT/A binding to diaphragm nerve terminals from SV2 knockout mice. These nerves normally express all three SV2 isoforms (FIG. 8) and we expect they all contribute to BoNT/A recognition of motor terminals. Because SV2A knockout and SV2A/B double knockout mice do not survive to adulthood and SV2C knockout mice are not available, we compared diaphragm preparations from available adult knockout mice that have the least amount of SV2 expression (SV2A(+/−) SV2B(−/−)), to wild-type (WT). As shown in FIGS. 6a and b, BoNT/A binding to NMJs from SV2A(+/−)SV2B(−/−) mice is significantly reduced compared to WT (72% reduction, P<0.001, t-test), while the levels of BoNT/B binding are the same (P>0.05, t-test), suggesting that SV2A and B are important for BoNT/A binding to motor nerve terminals. The remaining level of BoNT/A binding in SV2A(+/−)SV2B (−/−) NMJs is likely mediated by SV2C, which is not altered in these mice, and remaining reduced level of SV2A.

SV2B Knockout Mice have Reduced Sensitivity to BoNT/A:

To further establish the physiological meaning of these findings, we extended our studied to the whole animal. Among available SV2 knockout mice lines, SV2A knockout and SV2A/B double knockout mice both die within weeks after birth, suggesting SV2A is essential for maintaining normal synaptic transmission. In contrast, SV2B single knockout mice (SV2B(−/−)) have no apparent difference to wild-type (WT) mice. To minimize the potential defect in vivo on synaptic transmission, we chose to compare BoNT/A sensitivity of SV2B knockout mice and WT littermates. Sensitivity to BoNT/A was assessed with an established rapid assay, in which large amount of toxins are injected intravenously and the survival time (Time-to-death) after the injection were recorded (Boroff D A and Fleck U, *J. Bacteria* 92:1580-1581, 1966; Dong M et al., supra, 2003; Malizio C G, Methods and Protocols O. Hoist, ed. (Humana Press), pp. 27-39, 2000). This survival time can be converted to apparent toxicity from a previously established standard curve (Malizio C G, supra, 2000).

Identical amounts of BoNT/A ($10^4$-$10^6$ $LD_{50}$/ml) were injected into SV2B(−/−) and WT mice and their survival time is shown in FIG. 6c. SV2B knockout mice survived significantly longer than wild-type littermates (43.7±1.9 min versus 32.6±4.6 min). The effective toxin concentration estimated from the survival time of WT mice is about 2.5-fold more than SV2B(−/−) mice (8.4±2.9×$10^5$ $LD_{50}$/ml versus 3.4±0.5×$10^5$ $LD_{50}$/ml, FIG. 6c). The difference in effective toxicity reflects the shift of $LD_{50}$ value in SV2B knockout mice, i.e., these mice require approximately 2.5 fold more BoNT/A for a lethal dose than their WT littermates. The remaining toxicity in SV2B(−/−) mice is likely mediated by SV2A and C in their motor nerve terminals. These results provided functional evidence that SV2 is the physiological receptor for BoNT/A in vivo.

The present invention is not intended to be limited to the foregoing example, but rather to encompass all such variations and modifications as come within the scope of the appended claims.

We claim:

1. A method for reducing botulinum neurotoxin A (BoNT/A) toxicity in a human or non-human animal comprising the step of:
administering to the human or non-human animal an agent that reduces binding between BoNT/A and a synaptic vesicle glycoprotein SV2 in the human or non-human animal, wherein the agent is a polypeptide that comprises the amino acids at positions 486 to 523 of SEQ ID NO:16 and that is capable of binding to BoNT/A.

2. The method of claim 1, wherein the method is for reducing BoNT/A toxicity in a human.

3. The method of claim 1, wherein the agent further comprises a ganglioside.

* * * * *

SEQUENCE LISTING

```
<160> NUMBER OF SEQ ID NOS: 23

<210> SEQ ID NO 1
<211> LENGTH: 2229
<212> TYPE: DNA
<213> ORGANISM: Rattus norvegicus
<220> FEATURE:
<221> NAME/KEY: CDS
<222> LOCATION: (1)..(2229)

<400> SEQUENCE: 1 atg gaa gaa ggc ttt cga gac cga gca gcg ttc atc cgt ggg gcc aaa      48
Met Glu Glu Gly Phe Arg Asp Arg Ala Ala Phe Ile Arg Gly Ala Lys
1               5                   10                  15 gac att gcc aag gaa gtt aag aag cac gcg gcc aag aag gtg gtg aag      96
```

|   |   |   |   |   |   |   |   |   |   |   |   |   |   |   |   |      |
|---|---|---|---|---|---|---|---|---|---|---|---|---|---|---|---|------|
| Asp | Ile | Ala | Lys | Glu | Val | Lys | Lys | His | Ala | Ala | Lys | Lys | Val | Val | Lys |  |
|  |  |  | 20 |  |  |  | 25 |  |  |  | 30 |  |  |  |  |  |

```
ggt ctc gac aga gtc cag gat gaa tat tcc cga agg tcc tac tcc cgc    144
Gly Leu Asp Arg Val Gln Asp Glu Tyr Ser Arg Arg Ser Tyr Ser Arg
        35              40              45 ttt gag gag gag gag gat gat gat gac ttc cct gcc cct gct gac ggc    192
Phe Glu Glu Glu Glu Asp Asp Asp Asp Phe Pro Ala Pro Ala Asp Gly
    50              55              60 tat tac cgc gga gaa ggg gcc cag gat gag gag gaa ggt ggc gct tcc    240
Tyr Tyr Arg Gly Glu Gly Ala Gln Asp Glu Glu Glu Gly Gly Ala Ser
65              70              75              80 agt gat gcc act gag ggc cac gat gag gat gat gag atc tac gag gga    288
Ser Asp Ala Thr Glu Gly His Asp Glu Asp Asp Glu Ile Tyr Glu Gly
            85              90              95 gaa tat cag ggc atc ccc cgg gca gag tct ggg ggc aaa ggc gaa cgg    336
Glu Tyr Gln Gly Ile Pro Arg Ala Glu Ser Gly Gly Lys Gly Glu Arg
                100             105             110 atg gca gat ggg gca ccc ctg gct gga gtg aga ggg ggc tta agt gat    384
Met Ala Asp Gly Ala Pro Leu Ala Gly Val Arg Gly Gly Leu Ser Asp
            115             120             125 ggg gag ggt ccc cct ggg ggt cgc ggg gag gcg cag cgg cgt aaa gat    432
Gly Glu Gly Pro Pro Gly Gly Arg Gly Glu Ala Gln Arg Arg Lys Asp
130             135             140 cgg gaa gaa ttg gct cag cag tat gag acc atc ctc cgg gag tgc ggc    480
Arg Glu Glu Leu Ala Gln Gln Tyr Glu Thr Ile Leu Arg Glu Cys Gly
145             150             155             160 cat ggt cgc ttc cag tgg aca ctc tac ttc gtg ctg ggt ctg gcg ctg    528
His Gly Arg Phe Gln Trp Thr Leu Tyr Phe Val Leu Gly Leu Ala Leu
                165             170             175 atg gcc gat ggt gta gag gtc ttt gtg gtg ggc ttt gtg ctg ccc agt    576
Met Ala Asp Gly Val Glu Val Phe Val Val Gly Phe Val Leu Pro Ser
            180             185             190 gct gag aaa gat atg tgc ctg tcg gac tcc aac aaa ggc atg cta ggc    624
Ala Glu Lys Asp Met Cys Leu Ser Asp Ser Asn Lys Gly Met Leu Gly
        195             200             205 ctc att gtg tac ctg ggc atg atg gtg ggg gcc ttc ctc tgg gga ggc    672
Leu Ile Val Tyr Leu Gly Met Met Val Gly Ala Phe Leu Trp Gly Gly
    210             215             220 ctg gct gat cgg ctg ggt cgg aga cag tgt ctg ctc atc tcg ctc tca    720
Leu Ala Asp Arg Leu Gly Arg Arg Gln Cys Leu Leu Ile Ser Leu Ser
225             230             235             240 gtc aac agc gtc ttc gct ttc ttc tca tcc ttc gtc cag ggt tat ggc    768
Val Asn Ser Val Phe Ala Phe Phe Ser Ser Phe Val Gln Gly Tyr Gly
                245             250             255 acc ttc ctt ttc tgc cgc ctc ctt tct ggg gtt ggg att ggt ggt tcc    816
Thr Phe Leu Phe Cys Arg Leu Leu Ser Gly Val Gly Ile Gly Gly Ser
            260             265             270 atc ccc att gtc ttc tcc tat ttt tcg gag ttt ctg gcc cag gag aaa    864
Ile Pro Ile Val Phe Ser Tyr Phe Ser Glu Phe Leu Ala Gln Glu Lys
        275             280             285 cgt ggg gag cat ttg agc tgg ctc tgt atg ttc tgg atg att ggt ggc    912
Arg Gly Glu His Leu Ser Trp Leu Cys Met Phe Trp Met Ile Gly Gly
    290             295             300 gtg tat gca gct gca atg gcc tgg gcc atc atc ccc cac tat ggg tgg    960
Val Tyr Ala Ala Ala Met Ala Trp Ala Ile Ile Pro His Tyr Gly Trp
305             310             315             320 agt ttc cag atg ggc tct gct tac cag ttc cac agc tgg agg gtc ttt   1008
Ser Phe Gln Met Gly Ser Ala Tyr Gln Phe His Ser Trp Arg Val Phe
                325             330             335 gtc ctc gtc ttt gcc ttt ccc tct gtg ttt gcc atc ggg gct ctg act   1056
```

```
        Val Leu Val Phe Ala Phe Pro Ser Val Phe Ala Ile Gly Ala Leu Thr
                340                 345                 350 acg cag ccg gag agt ccc cgc ttc ttc tta gag aat ggg aag cac gat        1104
Thr Gln Pro Glu Ser Pro Arg Phe Phe Leu Glu Asn Gly Lys His Asp
            355                 360                 365 gag gcc tgg atg gtg ctg aag cag gtt cat gac acc aac atg cga gcc        1152
Glu Ala Trp Met Val Leu Lys Gln Val His Asp Thr Asn Met Arg Ala
        370                 375                 380 aag ggc cat cct gag cga gtc ttc tca gta acc cac att aaa acg att        1200
Lys Gly His Pro Glu Arg Val Phe Ser Val Thr His Ile Lys Thr Ile
385                 390                 395                 400 cat cag gag gat gaa ttg att gag atc cag tca gac aca gga acc tgg        1248
His Gln Glu Asp Glu Leu Ile Glu Ile Gln Ser Asp Thr Gly Thr Trp
                405                 410                 415 tac cag cgc tgg gga gtg cgg gct ttg agc ctg ggg ggt cag gtt tgg        1296
Tyr Gln Arg Trp Gly Val Arg Ala Leu Ser Leu Gly Gly Gln Val Trp
            420                 425                 430 ggg aac ttc ctc tcc tgc ttc agt cca gag tac cgg cgc atc act ctg        1344
Gly Asn Phe Leu Ser Cys Phe Ser Pro Glu Tyr Arg Arg Ile Thr Leu
        435                 440                 445 atg atg atg ggg gta tgg ttc acc atg tcc ttc agc tac tac ggt ttg        1392
Met Met Met Gly Val Trp Phe Thr Met Ser Phe Ser Tyr Tyr Gly Leu
450                 455                 460 act gtc tgg ttt ccc gac atg atc cgc cat ctc cag gct gtg gac tat        1440
Thr Val Trp Phe Pro Asp Met Ile Arg His Leu Gln Ala Val Asp Tyr
465                 470                 475                 480 gca gcc cga acc aaa gtg ttc cca ggg gag cgc gtg gag cac gtg aca        1488
Ala Ala Arg Thr Lys Val Phe Pro Gly Glu Arg Val Glu His Val Thr
                485                 490                 495 ttt aac ttc aca ctg gag aat cag atc cac cga ggg gga cag tac ttc        1536
Phe Asn Phe Thr Leu Glu Asn Gln Ile His Arg Gly Gly Gln Tyr Phe
            500                 505                 510 aat gac aag ttc atc ggg ctg cgt ctg aag tca gtg tcc ttt gag gat        1584
Asn Asp Lys Phe Ile Gly Leu Arg Leu Lys Ser Val Ser Phe Glu Asp
        515                 520                 525 tcc ctg ttt gag gaa tgt tac ttt gaa gat gtc aca tcc agc aac aca        1632
Ser Leu Phe Glu Glu Cys Tyr Phe Glu Asp Val Thr Ser Ser Asn Thr
    530                 535                 540 ttc ttc cgc aac tgc aca ttc atc aac acc gtg ttc tac aac acg gac        1680
Phe Phe Arg Asn Cys Thr Phe Ile Asn Thr Val Phe Tyr Asn Thr Asp
545                 550                 555                 560 ctg ttt gag tac aag ttc gtg aac agc cgc ctg gtg aac agc aca ttc        1728
Leu Phe Glu Tyr Lys Phe Val Asn Ser Arg Leu Val Asn Ser Thr Phe
                565                 570                 575 ctg cac aat aag gaa ggt tgc cca cta gat gtg aca ggg acg ggc gaa        1776
Leu His Asn Lys Glu Gly Cys Pro Leu Asp Val Thr Gly Thr Gly Glu
            580                 585                 590 ggt gcc tac atg gtg tac ttt gtc agc ttc ttg ggg aca ctg gct gtg        1824
Gly Ala Tyr Met Val Tyr Phe Val Ser Phe Leu Gly Thr Leu Ala Val
        595                 600                 605 ctc cct gga aat att gtg tct gct ctc atg gac aag att ggc agg             1872
Leu Pro Gly Asn Ile Val Ser Ala Leu Leu Met Asp Lys Ile Gly Arg
    610                 615                 620 ctc aga atg ctt gct ggt tcc agt gtg ttg tcc tgt gtt tcc tgc ttc        1920
Leu Arg Met Leu Ala Gly Ser Ser Val Leu Ser Cys Val Ser Cys Phe
625                 630                 635                 640 ttc ctg tct ttt ggg aac agt gag tca gcc atg atc gct ctc ctc tgc        1968
Phe Leu Ser Phe Gly Asn Ser Glu Ser Ala Met Ile Ala Leu Leu Cys
                645                 650                 655 ctt ttt ggg gga gtc agt att gca tcc tgg aac gcg ctg gac gtg ctg        2016
```

-continued

```
                Leu Phe Gly Gly Val Ser Ile Ala Ser Trp Asn Ala Leu Asp Val Leu
                                660                 665                 670 act gtt gaa ctc tac cct tcc gac aag agg acg acg gcc ttc ggc ttc          2064
Thr Val Glu Leu Tyr Pro Ser Asp Lys Arg Thr Thr Ala Phe Gly Phe
        675                 680                 685 ctg aat gcc ctg tgt aag ctg gca gct gta ctg ggc atc agc atc ttc          2112
Leu Asn Ala Leu Cys Lys Leu Ala Ala Val Leu Gly Ile Ser Ile Phe
    690                 695                 700 acg tcc ttt gtg gga atc acc aag gcc gct ccc atc ctc ttc gcc tca          2160
Thr Ser Phe Val Gly Ile Thr Lys Ala Ala Pro Ile Leu Phe Ala Ser
705                 710                 715                 720 gct gcg ctt gcc ctt ggt agc tct ctg gct ctg aag ctg cct gag acc          2208
Ala Ala Leu Ala Leu Gly Ser Ser Leu Ala Leu Lys Leu Pro Glu Thr
                725                 730                 735 cgg gga cag gtg ctg cag tga                                              2229
Arg Gly Gln Val Leu Gln
                740
```

<210> SEQ ID NO 2
<211> LENGTH: 742
<212> TYPE: PRT
<213> ORGANISM: Rattus norvegicus

<400> SEQUENCE: 2

```
Met Glu Glu Gly Phe Arg Asp Arg Ala Ala Phe Ile Arg Gly Ala Lys
1               5                   10                  15

Asp Ile Ala Lys Glu Val Lys Lys His Ala Ala Lys Lys Val Val Lys
            20                  25                  30

Gly Leu Asp Arg Val Gln Asp Glu Tyr Ser Arg Arg Ser Tyr Ser Arg
        35                  40                  45

Phe Glu Glu Glu Asp Asp Asp Phe Pro Ala Pro Ala Asp Gly
    50                  55                  60

Tyr Tyr Arg Gly Glu Gly Ala Gln Asp Glu Glu Gly Gly Ala Ser
65                  70                  75                  80

Ser Asp Ala Thr Glu Gly His Asp Glu Asp Glu Ile Tyr Glu Gly
            85                  90                  95

Glu Tyr Gln Gly Ile Pro Arg Ala Glu Ser Gly Gly Lys Gly Glu Arg
        100                 105                 110

Met Ala Asp Gly Ala Pro Leu Ala Gly Val Arg Gly Gly Leu Ser Asp
    115                 120                 125

Gly Glu Gly Pro Pro Gly Gly Arg Gly Glu Ala Gln Arg Arg Lys Asp
130                 135                 140

Arg Glu Glu Leu Ala Gln Gln Tyr Glu Thr Ile Leu Arg Glu Cys Gly
145                 150                 155                 160

His Gly Arg Phe Gln Trp Thr Leu Tyr Phe Val Leu Gly Leu Ala Leu
                165                 170                 175

Met Ala Asp Gly Val Glu Val Phe Val Val Gly Phe Val Leu Pro Ser
            180                 185                 190

Ala Glu Lys Asp Met Cys Leu Ser Asp Ser Asn Lys Gly Met Leu Gly
        195                 200                 205

Leu Ile Val Tyr Leu Gly Met Met Val Gly Ala Phe Leu Trp Gly Gly
    210                 215                 220

Leu Ala Asp Arg Leu Gly Arg Arg Gln Cys Leu Leu Ile Ser Leu Ser
225                 230                 235                 240

Val Asn Ser Val Phe Ala Phe Ser Ser Phe Val Gln Gly Tyr Gly
                245                 250                 255

Thr Phe Leu Phe Cys Arg Leu Leu Ser Gly Val Gly Ile Gly Gly Ser
```

```
                260                 265                 270
Ile Pro Ile Val Phe Ser Tyr Phe Ser Glu Phe Leu Ala Gln Glu Lys
            275                 280                 285

Arg Gly Glu His Leu Ser Trp Leu Cys Met Phe Trp Met Ile Gly Gly
            290                 295                 300

Val Tyr Ala Ala Ala Met Ala Trp Ala Ile Ile Pro His Tyr Gly Trp
305                             310                 315                 320

Ser Phe Gln Met Gly Ser Ala Tyr Gln Phe His Ser Trp Arg Val Phe
                    325                 330                 335

Val Leu Val Phe Ala Phe Pro Ser Val Phe Ala Ile Gly Ala Leu Thr
                340                 345                 350

Thr Gln Pro Glu Ser Pro Arg Phe Phe Leu Glu Asn Gly Lys His Asp
            355                 360                 365

Glu Ala Trp Met Val Leu Lys Gln Val His Asp Thr Asn Met Arg Ala
            370                 375                 380

Lys Gly His Pro Glu Arg Val Phe Ser Val Thr His Ile Lys Thr Ile
385                 390                 395                 400

His Gln Glu Asp Glu Leu Ile Glu Ile Gln Ser Asp Thr Gly Thr Trp
                    405                 410                 415

Tyr Gln Arg Trp Gly Val Arg Ala Leu Ser Leu Gly Gly Gln Val Trp
                420                 425                 430

Gly Asn Phe Leu Ser Cys Phe Ser Pro Glu Tyr Arg Arg Ile Thr Leu
                435                 440                 445

Met Met Met Gly Val Trp Phe Thr Met Ser Phe Ser Tyr Tyr Gly Leu
            450                 455                 460

Thr Val Trp Phe Pro Asp Met Ile Arg His Leu Gln Ala Val Asp Tyr
465                 470                 475                 480

Ala Ala Arg Thr Lys Val Phe Pro Gly Glu Arg Val Glu His Val Thr
                    485                 490                 495

Phe Asn Phe Thr Leu Glu Asn Gln Ile His Arg Gly Gly Gln Tyr Phe
                500                 505                 510

Asn Asp Lys Phe Ile Gly Leu Arg Leu Lys Ser Val Ser Phe Glu Asp
            515                 520                 525

Ser Leu Phe Glu Glu Cys Tyr Phe Glu Asp Val Thr Ser Ser Asn Thr
            530                 535                 540

Phe Phe Arg Asn Cys Thr Phe Ile Asn Thr Val Phe Tyr Asn Thr Asp
545                 550                 555                 560

Leu Phe Glu Tyr Lys Phe Val Asn Ser Arg Leu Val Asn Ser Thr Phe
                    565                 570                 575

Leu His Asn Lys Glu Gly Cys Pro Leu Asp Val Thr Gly Thr Gly Glu
                580                 585                 590

Gly Ala Tyr Met Val Tyr Phe Val Ser Phe Leu Gly Thr Leu Ala Val
            595                 600                 605

Leu Pro Gly Asn Ile Val Ser Ala Leu Leu Met Asp Lys Ile Gly Arg
            610                 615                 620

Leu Arg Met Leu Ala Gly Ser Ser Val Leu Ser Cys Val Ser Cys Phe
625                 630                 635                 640

Phe Leu Ser Phe Gly Asn Ser Glu Ser Ala Met Ile Ala Leu Leu Cys
                    645                 650                 655

Leu Phe Gly Gly Val Ser Ile Ala Ser Trp Asn Ala Leu Asp Val Leu
                660                 665                 670

Thr Val Glu Leu Tyr Pro Ser Asp Lys Arg Thr Thr Ala Phe Gly Phe
            675                 680                 685
```

-continued

| | | | | | | | | | | | | |
|---|---|---|---|---|---|---|---|---|---|---|---|---|
|Leu|Asn|Ala|Leu|Cys|Lys|Leu|Ala|Ala|Val|Leu|Gly|Ile|Ser|Ile|Phe|
| |690| | | |695| | | |700| | | | | | |

| | | | | | | | | | | | |
|---|---|---|---|---|---|---|---|---|---|---|---|
|Thr|Ser|Phe|Val|Gly|Ile|Thr|Lys|Ala|Ala|Pro|Ile|Leu|Phe|Ala|Ser|
|705| | | | |710| | | |715| | | | |720|

|Ala|Ala|Leu|Ala|Leu|Gly|Ser|Ser|Leu|Ala|Lys|Leu|Pro|Glu|Thr|
|---|---|---|---|---|---|---|---|---|---|---|---|---|---|---|
| | | | |725| | | |730| | | | |735| |

|Arg|Gly|Gln|Val|Leu|Gln|
|---|---|---|---|---|---|
| | |740| | | |

```
<210> SEQ ID NO 3
<211> LENGTH: 2052
<212> TYPE: DNA
<213> ORGANISM: Rattus norvegicus
<220> FEATURE:
<221> NAME/KEY: CDS
<222> LOCATION: (1)..(2052)

<400> SEQUENCE: 3
```

| | | | | | | | | | | | | | | | |
|---|---|---|---|---|---|---|---|---|---|---|---|---|---|---|---|
|atg|gat|gac|tac|agg|tat|cgg|gac|aac|tat|gag|ggc|tat|gcc|cct|aat|48|
|Met|Asp|Asp|Tyr|Arg|Tyr|Arg|Asp|Asn|Tyr|Glu|Gly|Tyr|Ala|Pro|Asn|
|1| | | |5| | | | |10| | | | |15| |

|gat|ggc|tac|tac|cgg|ggc|aat|gag|cag|aac|ccg|gaa|gaa|gat|gca|cag|96|
|---|---|---|---|---|---|---|---|---|---|---|---|---|---|---|---|---|
|Asp|Gly|Tyr|Tyr|Arg|Gly|Asn|Glu|Gln|Asn|Pro|Glu|Glu|Asp|Ala|Gln|
| | | | |20| | | | |25| | | | |30| |

|agc|gat|gtt|aca|gaa|ggc|cac|gat|gaa|gag|gat|gag|atc|tat|gag|ggc|144|
|---|---|---|---|---|---|---|---|---|---|---|---|---|---|---|---|---|
|Ser|Asp|Val|Thr|Glu|Gly|His|Asp|Glu|Glu|Asp|Glu|Ile|Tyr|Glu|Gly|
| | | |35| | | | |40| | | | |45| | |

|gag|tac|caa|ggc|atc|cct|cat|cca|gat|gat|gtc|aag|tct|aag|cag|act|192|
|---|---|---|---|---|---|---|---|---|---|---|---|---|---|---|---|---|
|Glu|Tyr|Gln|Gly|Ile|Pro|His|Pro|Asp|Asp|Val|Lys|Ser|Lys|Gln|Thr|
| |50| | | | |55| | | | |60| | | | |

|aag|atg|gca|ccg|tcc|aga|gca|gat|ggc|ctt|cgg|ggc|cag|gca|gac|ctg|240|
|---|---|---|---|---|---|---|---|---|---|---|---|---|---|---|---|---|
|Lys|Met|Ala|Pro|Ser|Arg|Ala|Asp|Gly|Leu|Arg|Gly|Gln|Ala|Asp|Leu|
|65| | | | |70| | | | |75| | | | |80|

|atg|gct|gag|aga|atg|gaa|gat|gag|gag|cag|ctc|gct|cac|cag|tac|gag|288|
|---|---|---|---|---|---|---|---|---|---|---|---|---|---|---|---|---|
|Met|Ala|Glu|Arg|Met|Glu|Asp|Glu|Glu|Gln|Leu|Ala|His|Gln|Tyr|Glu|
| | | | |85| | | | |90| | | | |95| |

|acc|atc|att|gat|gag|tgt|ggc|cat|ggg|cgc|ttc|cag|tgg|acc|ctc|ttt|336|
|---|---|---|---|---|---|---|---|---|---|---|---|---|---|---|---|---|
|Thr|Ile|Ile|Asp|Glu|Cys|Gly|His|Gly|Arg|Phe|Gln|Trp|Thr|Leu|Phe|
| | | |100| | | | |105| | | | |110| | |

|ttc|gtc|ttg|gtc|ttg|gcc|ttg|atg|gct|gac|gga|gtg|gaa|gtt|ttt|gtg|384|
|---|---|---|---|---|---|---|---|---|---|---|---|---|---|---|---|---|
|Phe|Val|Leu|Val|Leu|Ala|Leu|Met|Ala|Asp|Gly|Val|Glu|Val|Phe|Val|
| | |115| | | | |120| | | | |125| | | |

|gtg|agc|ttt|gct|ctg|cca|agt|gca|gag|aaa|gat|atg|tgt|ctg|tca|agt|432|
|---|---|---|---|---|---|---|---|---|---|---|---|---|---|---|---|---|
|Val|Ser|Phe|Ala|Leu|Pro|Ser|Ala|Glu|Lys|Asp|Met|Cys|Leu|Ser|Ser|
| |130| | | | |135| | | | |140| | | | |

|tcc|aag|aaa|gga|atg|ctc|ggg|ctg|att|gtc|tac|cta|gga|atg|atg|gca|480|
|---|---|---|---|---|---|---|---|---|---|---|---|---|---|---|---|---|
|Ser|Lys|Lys|Gly|Met|Leu|Gly|Leu|Ile|Val|Tyr|Leu|Gly|Met|Met|Ala|
|145| | | | |150| | | | |155| | | | |160|

|gga|gcc|ttc|atc|ctg|ggg|ggc|ctg|gct|gat|aaa|ctg|gga|agg|aag|aag|528|
|---|---|---|---|---|---|---|---|---|---|---|---|---|---|---|---|---|
|Gly|Ala|Phe|Ile|Leu|Gly|Gly|Leu|Ala|Asp|Lys|Leu|Gly|Arg|Lys|Lys|
| | | | |165| | | | |170| | | | |175| |

|gtc|ctc|agc|atg|tcc|ttg|gct|atc|aat|gct|tcc|ttt|gcc|tcc|ctc|tcc|576|
|---|---|---|---|---|---|---|---|---|---|---|---|---|---|---|---|---|
|Val|Leu|Ser|Met|Ser|Leu|Ala|Ile|Asn|Ala|Ser|Phe|Ala|Ser|Leu|Ser|
| | | |180| | | | |185| | | | |190| | |

|tcc|ttc|gtg|cag|gga|tat|gga|gct|ttc|ctc|ttc|tgc|aga|ctc|atc|tca|624|
|---|---|---|---|---|---|---|---|---|---|---|---|---|---|---|---|---|
|Ser|Phe|Val|Gln|Gly|Tyr|Gly|Ala|Phe|Leu|Phe|Cys|Arg|Leu|Ile|Ser|
| | |195| | | | |200| | | | |205| | | |

|ggc|ata|ggt|att|ggg|ggc|tcc|ctg|cca|att|gtt|ttt|gcc|tac|ttt|tct|672|
|---|---|---|---|---|---|---|---|---|---|---|---|---|---|---|---|---|
|Gly|Ile|Gly|Ile|Gly|Gly|Ser|Leu|Pro|Ile|Val|Phe|Ala|Tyr|Phe|Ser|
| |210| | | | |215| | | | |220| | | | |

|gag|ttc|tta|tca|cgg|gag|aaa|cgc|ggt|gag|cat|ctc|agc|tgg|ctg|ggt|720|

-continued

```
                Glu Phe Leu Ser Arg Glu Lys Arg Gly Glu His Leu Ser Trp Leu Gly
                225                 230                 235                 240 atc ttc tgg atg act ggg ggc atc tac gca tct gcc atg gcc tgg agc        768
Ile Phe Trp Met Thr Gly Gly Ile Tyr Ala Ser Ala Met Ala Trp Ser
                    245                 250                 255 atc att cca cac tat ggc tgg ggc ttc agc atg gga acc aat tat cac        816
Ile Ile Pro His Tyr Gly Trp Gly Phe Ser Met Gly Thr Asn Tyr His
                260                 265                 270 ttc cac agc tgg aga gtg ttt gtc atc gtc tgt gct ctg cct gcc act        864
Phe His Ser Trp Arg Val Phe Val Ile Val Cys Ala Leu Pro Ala Thr
                275                 280                 285 gtg tcc atg gtg gcc ctg aag ttc atg cca gaa agc ccc agg ttc ctg        912
Val Ser Met Val Ala Leu Lys Phe Met Pro Glu Ser Pro Arg Phe Leu
            290                 295                 300 ctg gag atg ggc aag cat gat gaa gcc tgg atg att ctc aag caa gtc        960
Leu Glu Met Gly Lys His Asp Glu Ala Trp Met Ile Leu Lys Gln Val
305                 310                 315                 320 cat gac acc aac atg aga gct aag ggg acc cct gag aag gtg ttc acg       1008
His Asp Thr Asn Met Arg Ala Lys Gly Thr Pro Glu Lys Val Phe Thr
                    325                 330                 335 gtt tcc cac atc aaa act ccc aag caa atg gat gaa ttc att gag atc       1056
Val Ser His Ile Lys Thr Pro Lys Gln Met Asp Glu Phe Ile Glu Ile
                340                 345                 350 cag agt tca aca ggg act tgg tac cag cgc tgg ttg gtc agg ttc atg       1104
Gln Ser Ser Thr Gly Thr Trp Tyr Gln Arg Trp Leu Val Arg Phe Met
            355                 360                 365 acc att ttc aaa cag gtg tgg gat aac gcc ttg tac tgt gtg atg gga       1152
Thr Ile Phe Lys Gln Val Trp Asp Asn Ala Leu Tyr Cys Val Met Gly
370                 375                 380 ccc tac aga atg aac acc ctg att ctg gct gtg gtc tgg ttc acc atg       1200
Pro Tyr Arg Met Asn Thr Leu Ile Leu Ala Val Val Trp Phe Thr Met
385                 390                 395                 400 gcc tta agt tac tat ggc ctg aca gtg tgg ttc ccc gac atg atc cgg       1248
Ala Leu Ser Tyr Tyr Gly Leu Thr Val Trp Phe Pro Asp Met Ile Arg
                405                 410                 415 tat ttc cag gat gaa gaa tat aag tct aaa atg aag gtg ttt ttt ggt       1296
Tyr Phe Gln Asp Glu Glu Tyr Lys Ser Lys Met Lys Val Phe Phe Gly
                420                 425                 430 gag cac gtg cat ggc gcc aca atc aac ttc acc atg gaa aac cag atc       1344
Glu His Val His Gly Ala Thr Ile Asn Phe Thr Met Glu Asn Gln Ile
            435                 440                 445 cac caa cat ggg aag ctt gtg aac gat aag ttc ata aag atg tac ttt       1392
His Gln His Gly Lys Leu Val Asn Asp Lys Phe Ile Lys Met Tyr Phe
450                 455                 460 aag cat gtc ctc ttt gag gac aca ttc ttt gac aaa tgc tat ttt gaa       1440
Lys His Val Leu Phe Glu Asp Thr Phe Phe Asp Lys Cys Tyr Phe Glu
465                 470                 475                 480 gat gtg aca tcc aca gat act tat ttc aag aac tgc acc att gaa tcg       1488
Asp Val Thr Ser Thr Asp Thr Tyr Phe Lys Asn Cys Thr Ile Glu Ser
                485                 490                 495 act acc ttc tac aac aca gac ctc tac aaa cac aag ttc att gac tgt       1536
Thr Thr Phe Tyr Asn Thr Asp Leu Tyr Lys His Lys Phe Ile Asp Cys
                500                 505                 510 cgg ttt atc aat tcc acc ttt ctg gag cag aag gag ggc tgc cac atg       1584
Arg Phe Ile Asn Ser Thr Phe Leu Glu Gln Lys Glu Gly Cys His Met
            515                 520                 525 gac ttt gaa gag gac aat gat ttt ctg att tac ctc gtc agc ttc ctc       1632
Asp Phe Glu Glu Asp Asn Asp Phe Leu Ile Tyr Leu Val Ser Phe Leu
530                 535                 540 ggc agc ctg tct gtc ttg cct ggg aac ata att tct gcc ctg ctc atg       1680
```

```
Gly Ser Leu Ser Val Leu Pro Gly Asn Ile Ile Ser Ala Leu Leu Met
545                 550                 555                 560 gac aga atc gga aga ctt aag atg att ggt ggc tcc atg ctc atc tct    1728
Asp Arg Ile Gly Arg Leu Lys Met Ile Gly Gly Ser Met Leu Ile Ser
                565                 570                 575 gca gtc tgc tgc ttc ttc ctg ttt ttt ggc aac agc gag tct gcg atg    1776
Ala Val Cys Cys Phe Phe Leu Phe Phe Gly Asn Ser Glu Ser Ala Met
                580                 585                 590 atc ggc tgg caa tgc ctg ttc tgt ggg acc agc att gca gcc tgg aat    1824
Ile Gly Trp Gln Cys Leu Phe Cys Gly Thr Ser Ile Ala Ala Trp Asn
                595                 600                 605 gct ctg gat gtg atc aca gta gag ctg tat ccc acc aac cag agg gcc    1872
Ala Leu Asp Val Ile Thr Val Glu Leu Tyr Pro Thr Asn Gln Arg Ala
                610                 615                 620 act gcc ttc ggc atc ctc aat gga ctg tgc aaa ctt ggt gcc atc ctg    1920
Thr Ala Phe Gly Ile Leu Asn Gly Leu Cys Lys Leu Gly Ala Ile Leu
625                 630                 635                 640 gga aac act atc ttt gct tct ttt gtt ggg atc acc aaa gtg gtc ccc    1968
Gly Asn Thr Ile Phe Ala Ser Phe Val Gly Ile Thr Lys Val Val Pro
                645                 650                 655 atc ctt ctg gct gct gct tct ctg gtt gga ggt ggc ttg gtt gcc ctt    2016
Ile Leu Leu Ala Ala Ala Ser Leu Val Gly Gly Gly Leu Val Ala Leu
                660                 665                 670 cga ctg cca gag act cga gag cag gtc ctg atg tga                    2052
Arg Leu Pro Glu Thr Arg Glu Gln Val Leu Met
                675                 680

<210> SEQ ID NO 4
<211> LENGTH: 683
<212> TYPE: PRT
<213> ORGANISM: Rattus norvegicus

<400> SEQUENCE: 4

Met Asp Asp Tyr Arg Tyr Arg Asp Asn Tyr Glu Gly Tyr Ala Pro Asn
1               5                   10                  15

Asp Gly Tyr Tyr Arg Gly Asn Glu Gln Asn Pro Glu Glu Asp Ala Gln
                20                  25                  30

Ser Asp Val Thr Glu Gly His Asp Glu Glu Asp Glu Ile Tyr Glu Gly
                35                  40                  45

Glu Tyr Gln Gly Ile Pro His Pro Asp Val Lys Ser Lys Gln Thr
50                  55                  60

Lys Met Ala Pro Ser Arg Ala Asp Gly Leu Arg Gly Gln Ala Asp Leu
65                  70                  75                  80

Met Ala Glu Arg Met Glu Asp Glu Gln Leu Ala His Gln Tyr Glu
                85                  90                  95

Thr Ile Ile Asp Glu Cys Gly His Gly Arg Phe Gln Trp Thr Leu Phe
                100                 105                 110

Phe Val Leu Val Leu Ala Leu Met Ala Asp Gly Val Glu Val Phe Val
                115                 120                 125

Val Ser Phe Ala Leu Pro Ser Ala Glu Lys Asp Met Cys Leu Ser Ser
                130                 135                 140

Ser Lys Lys Gly Met Leu Gly Leu Ile Val Tyr Leu Gly Met Met Ala
145                 150                 155                 160

Gly Ala Phe Ile Leu Gly Gly Leu Ala Asp Lys Leu Gly Arg Lys Lys
                165                 170                 175

Val Leu Ser Met Ser Leu Ala Ile Asn Ala Ser Phe Ala Ser Leu Ser
                180                 185                 190

Ser Phe Val Gln Gly Tyr Gly Ala Phe Leu Phe Cys Arg Leu Ile Ser
```

```
              195                 200                 205
Gly Ile Gly Ile Gly Gly Ser Leu Pro Ile Val Phe Ala Tyr Phe Ser
            210                 215                 220

Glu Phe Leu Ser Arg Glu Lys Arg Gly Glu His Leu Ser Trp Leu Gly
225                 230                 235                 240

Ile Phe Trp Met Thr Gly Gly Ile Tyr Ala Ser Ala Met Ala Trp Ser
                245                 250                 255

Ile Ile Pro His Tyr Gly Trp Gly Phe Ser Met Gly Thr Asn Tyr His
                260                 265                 270

Phe His Ser Trp Arg Val Phe Ile Val Cys Ala Leu Pro Ala Thr
            275                 280                 285

Val Ser Met Val Ala Leu Lys Phe Met Pro Glu Ser Pro Arg Phe Leu
    290                 295                 300

Leu Glu Met Gly Lys His Asp Glu Ala Trp Met Ile Leu Lys Gln Val
305                 310                 315                 320

His Asp Thr Asn Met Arg Ala Lys Gly Thr Pro Glu Lys Val Phe Thr
                325                 330                 335

Val Ser His Ile Lys Thr Pro Lys Gln Met Asp Glu Phe Ile Glu Ile
                340                 345                 350

Gln Ser Ser Thr Gly Thr Trp Tyr Gln Arg Trp Leu Val Arg Phe Met
            355                 360                 365

Thr Ile Phe Lys Gln Val Trp Asp Asn Ala Leu Tyr Cys Val Met Gly
    370                 375                 380

Pro Tyr Arg Met Asn Thr Leu Ile Leu Ala Val Val Trp Phe Thr Met
385                 390                 395                 400

Ala Leu Ser Tyr Tyr Gly Leu Thr Val Trp Phe Pro Asp Met Ile Arg
                405                 410                 415

Tyr Phe Gln Asp Glu Glu Tyr Lys Ser Lys Met Lys Val Phe Phe Gly
                420                 425                 430

Glu His Val His Gly Ala Thr Ile Asn Phe Thr Met Glu Asn Gln Ile
            435                 440                 445

His Gln His Gly Lys Leu Val Asn Asp Lys Phe Ile Lys Met Tyr Phe
450                 455                 460

Lys His Val Leu Phe Glu Asp Thr Phe Phe Asp Lys Cys Tyr Phe Glu
465                 470                 475                 480

Asp Val Thr Ser Thr Asp Thr Tyr Phe Lys Asn Cys Thr Ile Glu Ser
                485                 490                 495

Thr Thr Phe Tyr Asn Thr Asp Leu Tyr Lys His Lys Phe Ile Asp Cys
                500                 505                 510

Arg Phe Ile Asn Ser Thr Phe Leu Glu Gln Lys Glu Gly Cys His Met
            515                 520                 525

Asp Phe Glu Glu Asp Asn Asp Phe Leu Ile Tyr Leu Val Ser Phe Leu
    530                 535                 540

Gly Ser Leu Ser Val Leu Pro Gly Asn Ile Ile Ser Ala Leu Leu Met
545                 550                 555                 560

Asp Arg Ile Gly Arg Leu Lys Met Ile Gly Gly Ser Met Leu Ile Ser
                565                 570                 575

Ala Val Cys Cys Phe Phe Leu Phe Phe Gly Asn Ser Glu Ser Ala Met
                580                 585                 590

Ile Gly Trp Gln Cys Leu Phe Cys Gly Thr Ser Ile Ala Ala Trp Asn
            595                 600                 605

Ala Leu Asp Val Ile Thr Val Glu Leu Tyr Pro Thr Asn Gln Arg Ala
    610                 615                 620
```

```
             Thr Ala Phe Gly Ile Leu Asn Gly Leu Cys Lys Leu Gly Ala Ile Leu
             625                 630                 635                 640

Gly Asn Thr Ile Phe Ala Ser Phe Val Gly Ile Thr Lys Val Val Pro
                             645                 650                 655

Ile Leu Leu Ala Ala Ser Leu Val Gly Gly Leu Val Ala Leu
                660                 665                 670

Arg Leu Pro Glu Thr Arg Glu Gln Val Leu Met
                675                 680

<210> SEQ ID NO 5
<211> LENGTH: 2184
<212> TYPE: DNA
<213> ORGANISM: Rattus norvegicus
<220> FEATURE:
<221> NAME/KEY: CDS
<222> LOCATION: (1)..(2184)

<400> SEQUENCE: 5 atg gaa gac tcc tac aag gat agg act tca ctg atg aag ggc gcc aag       48
Met Glu Asp Ser Tyr Lys Asp Arg Thr Ser Leu Met Lys Gly Ala Lys
1               5                   10                  15 gac att gcc aaa gag gtg aag aag caa aca gtg aag aag gtg aac cag       96
Asp Ile Ala Lys Glu Val Lys Lys Gln Thr Val Lys Lys Val Asn Gln
                20                  25                  30 gca gtg gac cgg gcc cag gat gaa tac acc cag cgg tcc tac agt cga     144
Ala Val Asp Arg Ala Gln Asp Glu Tyr Thr Gln Arg Ser Tyr Ser Arg
            35                  40                  45 ttc cag gat gaa gat gat gat gat gac tac tac cca cct gga gaa acc     192
Phe Gln Asp Glu Asp Asp Asp Asp Asp Tyr Tyr Pro Pro Gly Glu Thr
        50                  55                  60 tac agt ggg gag gcc aat gat gat gaa ggc tca agt gaa gcc act gag     240
Tyr Ser Gly Glu Ala Asn Asp Asp Glu Gly Ser Ser Glu Ala Thr Glu
65                  70                  75                  80 ggt cac gat gaa gaa gac gag atc tat gaa ggg gaa tac cag ggc atc     288
Gly His Asp Glu Glu Asp Glu Ile Tyr Glu Gly Glu Tyr Gln Gly Ile
                85                  90                  95 ccc agc acg aac caa ggg aag gac agc ata gtg tct gta gga caa ccc     336
Pro Ser Thr Asn Gln Gly Lys Asp Ser Ile Val Ser Val Gly Gln Pro
            100                 105                 110 aaa gga gat gag tac aag gac cgc aga gag ctg gag tca gag agg agg     384
Lys Gly Asp Glu Tyr Lys Asp Arg Arg Glu Leu Glu Ser Glu Arg Arg
        115                 120                 125 gct gat gag gag gag ctc gcc cag cag tat gag ctg ata atc caa gag     432
Ala Asp Glu Glu Glu Leu Ala Gln Gln Tyr Glu Leu Ile Ile Gln Glu
    130                 135                 140 tgt ggc cat ggc cgt ttc cag tgg gcc ctt ttc ttc gtc ctg ggc atg     480
Cys Gly His Gly Arg Phe Gln Trp Ala Leu Phe Phe Val Leu Gly Met
145                 150                 155                 160 gct ctc atg gca gac ggc gtg gag gtg ttt gtg gtg ggc ttt gtg tta     528
Ala Leu Met Ala Asp Gly Val Glu Val Phe Val Val Gly Phe Val Leu
                165                 170                 175 ccc agt gca gag aca gac cta tgc ata ccg aat tca gga tct gga tgg     576
Pro Ser Ala Glu Thr Asp Leu Cys Ile Pro Asn Ser Gly Ser Gly Trp
            180                 185                 190 cta ggc agc ata gtg tac ctc ggg atg atg gtg ggg gcg ttc ttc tgg     624
Leu Gly Ser Ile Val Tyr Leu Gly Met Met Val Gly Ala Phe Phe Trp
        195                 200                 205 gga gga ctg gca gac aaa gtg gga agg aag cag tct ctt ctg att tgc     672
Gly Gly Leu Ala Asp Lys Val Gly Arg Lys Gln Ser Leu Leu Ile Cys
    210                 215                 220 atg tcc gtc aac gga ttc ttt gcc ttc ctt tct tca ttt gtc caa ggt     720
```

```
Met Ser Val Asn Gly Phe Phe Ala Phe Leu Ser Ser Phe Val Gln Gly
225             230             235             240 tac ggc ttc ttt ctc ctc tgt cgt ttg ctt tca gga ttc ggg att gga    768
Tyr Gly Phe Phe Leu Leu Cys Arg Leu Leu Ser Gly Phe Gly Ile Gly
            245             250             255 ggc gcc att ccc act gtg ttc tcc tac ttt gct gaa gtc ctg gcc cgg    816
Gly Ala Ile Pro Thr Val Phe Ser Tyr Phe Ala Glu Val Leu Ala Arg
        260             265             270 gag aag cgc ggt gag cac ctc agt tgg ctc tgc atg ttc tgg atg att    864
Glu Lys Arg Gly Glu His Leu Ser Trp Leu Cys Met Phe Trp Met Ile
    275             280             285 ggc ggt atc tat gct tca gcc atg gcc tgg gcc atc atc ccc cac tat    912
Gly Gly Ile Tyr Ala Ser Ala Met Ala Trp Ala Ile Ile Pro His Tyr
290             295             300 ggg tgg agc ttc agc atg ggc tca gcc tac cag ttc cac agc tgg cgc    960
Gly Trp Ser Phe Ser Met Gly Ser Ala Tyr Gln Phe His Ser Trp Arg
305             310             315             320 gtc ttc gtc atc gtc tgt gcc ctc ccg tgc gtc tcc tcg gtg gtg gcc   1008
Val Phe Val Ile Val Cys Ala Leu Pro Cys Val Ser Ser Val Val Ala
            325             330             335 ctc acc ttc atg ccc gaa agc cct cgg ttc ttg ctg gag gta gga aaa   1056
Leu Thr Phe Met Pro Glu Ser Pro Arg Phe Leu Leu Glu Val Gly Lys
        340             345             350 cat gat gaa gcc tgg atg att ctg aag cta att cat gat acc aac atg   1104
His Asp Glu Ala Trp Met Ile Leu Lys Leu Ile His Asp Thr Asn Met
    355             360             365 aga gcc cgg ggc cag cca gag aag gtc ttc acg gta aat aaa atc aag   1152
Arg Ala Arg Gly Gln Pro Glu Lys Val Phe Thr Val Asn Lys Ile Lys
370             375             380 act ccc aag caa ata gat gag ctg att gag att gag agc gac aca gga   1200
Thr Pro Lys Gln Ile Asp Glu Leu Ile Glu Ile Glu Ser Asp Thr Gly
385             390             395             400 acc tgg tac cgg agg tgt ttt gtt cgg atc cgc aca gaa ctg tac gga   1248
Thr Trp Tyr Arg Arg Cys Phe Val Arg Ile Arg Thr Glu Leu Tyr Gly
            405             410             415 att tgg ttg act ttt atg aga tgc ttc aac tac ccg gtc agg gaa aac   1296
Ile Trp Leu Thr Phe Met Arg Cys Phe Asn Tyr Pro Val Arg Glu Asn
        420             425             430 acc ata aag ctt acg att gtt tgg ttc acc ctg tcc ttt ggg tac tat   1344
Thr Ile Lys Leu Thr Ile Val Trp Phe Thr Leu Ser Phe Gly Tyr Tyr
    435             440             445 gga ctg tcc gtt tgg ttc cca gat gtc att aaa cac ctc cag tct gac   1392
Gly Leu Ser Val Trp Phe Pro Asp Val Ile Lys His Leu Gln Ser Asp
450             455             460 gag tac gcc ctg ctg act cgg aat gtg cag aag gat aaa tat gca aac   1440
Glu Tyr Ala Leu Leu Thr Arg Asn Val Gln Lys Asp Lys Tyr Ala Asn
465             470             475             480 ttt agc att aac ttc acc atg gaa aac cag gtc cac acc gga atg gaa   1488
Phe Ser Ile Asn Phe Thr Met Glu Asn Gln Val His Thr Gly Met Glu
            485             490             495 tat gac aat ggc agg ttc ctc gga gtc aaa ttc aaa tcg gta acc ttc   1536
Tyr Asp Asn Gly Arg Phe Leu Gly Val Lys Phe Lys Ser Val Thr Phe
        500             505             510 aag gat tca gtg ttt aag tcc tgc acc ttt gac gat gtg acc tca gtc   1584
Lys Asp Ser Val Phe Lys Ser Cys Thr Phe Asp Asp Val Thr Ser Val
    515             520             525 aac acc tac ttc aag aac tgc acg ttt att gat acc ctt ttt gag aac   1632
Asn Thr Tyr Phe Lys Asn Cys Thr Phe Ile Asp Thr Leu Phe Glu Asn
530             535             540 aca gat ttt gag ccc tat aaa ttc ata gac agc gag ttt caa aac tgc   1680
```

```
Thr Asp Phe Glu Pro Tyr Lys Phe Ile Asp Ser Glu Phe Gln Asn Cys
545                 550                 555                 560 tcg ttt ctt cac aat aag acg gga tgt cag att act ttt gac gac gac    1728
Ser Phe Leu His Asn Lys Thr Gly Cys Gln Ile Thr Phe Asp Asp Asp
                565                 570                 575 tac agt gcc tac tgg att tac ttt gtc aac ttt ctc ggg aca ttg gca    1776
Tyr Ser Ala Tyr Trp Ile Tyr Phe Val Asn Phe Leu Gly Thr Leu Ala
                580                 585                 590 gtg tta cca gga aat atc gtg tct gct ctc ctg atg gac agg atc ggg    1824
Val Leu Pro Gly Asn Ile Val Ser Ala Leu Leu Met Asp Arg Ile Gly
            595                 600                 605 cgc tta acg atg cta ggt ggc tcc atg gtg ctc tcg ggg atc agc tgc    1872
Arg Leu Thr Met Leu Gly Gly Ser Met Val Leu Ser Gly Ile Ser Cys
        610                 615                 620 ttc ttc ctg tgg ttt ggc acc agc gaa tcc atg atg ata ggc atg ctg    1920
Phe Phe Leu Trp Phe Gly Thr Ser Glu Ser Met Met Ile Gly Met Leu
625                 630                 635                 640 tgc ttg tac aac gga ctg acc atc tca gcg tgg aac tct ctt gat gta    1968
Cys Leu Tyr Asn Gly Leu Thr Ile Ser Ala Trp Asn Ser Leu Asp Val
                645                 650                 655 gtc acg gtg gaa cta tac ccc aca gac cgg aga gca acg ggc ttt ggc    2016
Val Thr Val Glu Leu Tyr Pro Thr Asp Arg Arg Ala Thr Gly Phe Gly
                660                 665                 670 ttc ttg aac gca ctc tgt aaa gca gcg gcc gtc ctg gga aac tta ata    2064
Phe Leu Asn Ala Leu Cys Lys Ala Ala Ala Val Leu Gly Asn Leu Ile
            675                 680                 685 ttc ggc tcc ttg gtc agc atc acc aaa gca atc cct atc ctg ctg gct    2112
Phe Gly Ser Leu Val Ser Ile Thr Lys Ala Ile Pro Ile Leu Leu Ala
        690                 695                 700 tcc acc gtg ctc gtg tgt gga gga ctc gtg ggg ctg cgc ctg ccc gac    2160
Ser Thr Val Leu Val Cys Gly Gly Leu Val Gly Leu Arg Leu Pro Asp
705                 710                 715                 720 aca aga acc cag gtt ctg atg tga                                     2184
Thr Arg Thr Gln Val Leu Met
                725

<210> SEQ ID NO 6
<211> LENGTH: 727
<212> TYPE: PRT
<213> ORGANISM: Rattus norvegicus

<400> SEQUENCE: 6

Met Glu Asp Ser Tyr Lys Asp Arg Thr Ser Leu Met Lys Gly Ala Lys
1               5                   10                  15

Asp Ile Ala Lys Glu Val Lys Lys Gln Thr Val Lys Lys Val Asn Gln
            20                  25                  30

Ala Val Asp Arg Ala Gln Asp Glu Tyr Thr Gln Arg Ser Tyr Ser Arg
        35                  40                  45

Phe Gln Asp Glu Asp Asp Asp Asp Tyr Tyr Pro Pro Gly Glu Thr
    50                  55                  60

Tyr Ser Gly Glu Ala Asn Asp Asp Glu Gly Ser Ser Glu Ala Thr Glu
65                  70                  75                  80

Gly His Asp Glu Glu Asp Glu Ile Tyr Glu Gly Glu Tyr Gln Gly Ile
                85                  90                  95

Pro Ser Thr Asn Gln Gly Lys Asp Ser Ile Val Ser Val Gly Gln Pro
            100                 105                 110

Lys Gly Asp Glu Tyr Lys Asp Arg Arg Glu Leu Glu Ser Glu Arg Arg
        115                 120                 125

Ala Asp Glu Glu Glu Leu Ala Gln Gln Tyr Glu Leu Ile Ile Gln Glu
```

```
            130                 135                 140
Cys Gly His Gly Arg Phe Gln Trp Ala Leu Phe Phe Val Leu Gly Met
145                 150                 155                 160

Ala Leu Met Ala Asp Gly Val Glu Val Phe Val Gly Phe Val Leu
                165                 170                 175

Pro Ser Ala Glu Thr Asp Leu Cys Ile Pro Asn Ser Gly Ser Gly Trp
                180                 185                 190

Leu Gly Ser Ile Val Tyr Leu Gly Met Met Val Gly Ala Phe Phe Trp
                195                 200                 205

Gly Gly Leu Ala Asp Lys Val Gly Arg Lys Gln Ser Leu Leu Ile Cys
210                 215                 220

Met Ser Val Asn Gly Phe Phe Ala Phe Leu Ser Ser Phe Val Gln Gly
225                 230                 235                 240

Tyr Gly Phe Phe Leu Leu Cys Arg Leu Leu Ser Gly Phe Gly Ile Gly
                245                 250                 255

Gly Ala Ile Pro Thr Val Phe Ser Tyr Phe Ala Glu Val Leu Ala Arg
                260                 265                 270

Glu Lys Arg Gly Glu His Leu Ser Trp Leu Cys Met Phe Trp Met Ile
                275                 280                 285

Gly Gly Ile Tyr Ala Ser Ala Met Ala Trp Ala Ile Ile Pro His Tyr
                290                 295                 300

Gly Trp Ser Phe Ser Met Gly Ser Ala Tyr Gln Phe His Ser Trp Arg
305                 310                 315                 320

Val Phe Val Ile Val Cys Ala Leu Pro Cys Val Ser Ser Val Val Ala
                325                 330                 335

Leu Thr Phe Met Pro Glu Ser Pro Arg Phe Leu Leu Glu Val Gly Lys
                340                 345                 350

His Asp Glu Ala Trp Met Ile Leu Lys Leu Ile His Asp Thr Asn Met
                355                 360                 365

Arg Ala Arg Gly Gln Pro Glu Lys Val Phe Thr Val Asn Lys Ile Lys
                370                 375                 380

Thr Pro Lys Gln Ile Asp Glu Leu Ile Glu Ile Glu Ser Asp Thr Gly
385                 390                 395                 400

Thr Trp Tyr Arg Arg Cys Phe Val Arg Ile Arg Thr Glu Leu Tyr Gly
                405                 410                 415

Ile Trp Leu Thr Phe Met Arg Cys Phe Asn Tyr Pro Val Arg Glu Asn
                420                 425                 430

Thr Ile Lys Leu Thr Ile Val Trp Phe Thr Leu Ser Phe Gly Tyr Tyr
                435                 440                 445

Gly Leu Ser Val Trp Phe Pro Asp Val Ile Lys His Leu Gln Ser Asp
450                 455                 460

Glu Tyr Ala Leu Leu Thr Arg Asn Val Gln Lys Asp Lys Tyr Ala Asn
465                 470                 475                 480

Phe Ser Ile Asn Phe Thr Met Glu Asn Gln Val His Thr Gly Met Glu
                485                 490                 495

Tyr Asp Asn Gly Arg Phe Leu Gly Val Lys Phe Lys Ser Val Thr Phe
                500                 505                 510

Lys Asp Ser Val Phe Lys Ser Cys Thr Phe Asp Asp Val Thr Ser Val
                515                 520                 525

Asn Thr Tyr Phe Lys Asn Cys Thr Phe Ile Asp Thr Leu Phe Glu Asn
                530                 535                 540

Thr Asp Phe Glu Pro Tyr Lys Phe Ile Asp Ser Glu Phe Gln Asn Cys
545                 550                 555                 560
```

```
Ser Phe Leu His Asn Lys Thr Gly Cys Gln Ile Thr Phe Asp Asp Asp
                565                 570                 575

Tyr Ser Ala Tyr Trp Ile Tyr Phe Val Asn Phe Leu Gly Thr Leu Ala
            580                 585                 590

Val Leu Pro Gly Asn Ile Val Ser Ala Leu Leu Met Asp Arg Ile Gly
        595                 600                 605

Arg Leu Thr Met Leu Gly Gly Ser Met Val Leu Ser Gly Ile Ser Cys
    610                 615                 620

Phe Phe Leu Trp Phe Gly Thr Ser Glu Ser Met Met Ile Gly Met Leu
625                 630                 635                 640

Cys Leu Tyr Asn Gly Leu Thr Ile Ser Ala Trp Asn Ser Leu Asp Val
                645                 650                 655

Val Thr Val Glu Leu Tyr Pro Thr Asp Arg Arg Ala Thr Gly Phe Gly
            660                 665                 670

Phe Leu Asn Ala Leu Cys Lys Ala Ala Ala Val Leu Gly Asn Leu Ile
        675                 680                 685

Phe Gly Ser Leu Val Ser Ile Thr Lys Ala Ile Pro Ile Leu Leu Ala
    690                 695                 700

Ser Thr Val Leu Val Cys Gly Leu Val Gly Leu Arg Leu Pro Asp
705                 710                 715                 720

Thr Arg Thr Gln Val Leu Met
                725

<210> SEQ ID NO 7
<211> LENGTH: 2229
<212> TYPE: DNA
<213> ORGANISM: Mus musculus
<220> FEATURE:
<221> NAME/KEY: CDS
<222> LOCATION: (1)..(2229)

<400> SEQUENCE: 7 atg gaa gaa ggc ttt cga gac cga gca gcg ttc atc cgt ggg gcc aaa      48
Met Glu Glu Gly Phe Arg Asp Arg Ala Ala Phe Ile Arg Gly Ala Lys
1               5                   10                  15 gac att gcc aag gaa gtg aag aag cat gcg gcc aag aag gtg gtg aag      96
Asp Ile Ala Lys Glu Val Lys Lys His Ala Ala Lys Lys Val Val Lys
            20                  25                  30 ggc ctt gac aga gtc cag gat gag tat tcc cga agg tcc tac tcc cgc    144
Gly Leu Asp Arg Val Gln Asp Glu Tyr Ser Arg Arg Ser Tyr Ser Arg
        35                  40                  45 ttt gag gag gag gac gac gac gat gac ttc cct gcc cct gcg gac ggc    192
Phe Glu Glu Glu Asp Asp Asp Asp Asp Phe Pro Ala Pro Ala Asp Gly
    50                  55                  60 tat tac cgc gga gaa ggg gcc cag gat gag gag gaa ggt ggc gct tct    240
Tyr Tyr Arg Gly Glu Gly Ala Gln Asp Glu Glu Glu Gly Gly Ala Ser
65                  70                  75                  80 agt gat gcc acc gag ggc cac gat gaa gat gat gag atc tat gag gga    288
Ser Asp Ala Thr Glu Gly His Asp Glu Asp Asp Glu Ile Tyr Glu Gly
                85                  90                  95 gaa tat cag ggc atc ccc cgg gca gag tct ggg ggc aaa ggc gaa cgc    336
Glu Tyr Gln Gly Ile Pro Arg Ala Glu Ser Gly Gly Lys Gly Glu Arg
            100                 105                 110 atg gca gat ggg gca ccc ctg gct gga gtg aga ggg ggc ttg agt gat    384
Met Ala Asp Gly Ala Pro Leu Ala Gly Val Arg Gly Gly Leu Ser Asp
        115                 120                 125 ggg gag ggt ccc cct ggg ggt cgg ggg gag gcg cag cgg cgt aaa gat    432
Gly Glu Gly Pro Pro Gly Gly Arg Gly Glu Ala Gln Arg Arg Lys Asp
    130                 135                 140
```

| | | |
|---|---|---|
| cgg gaa gaa ttg gct cag cag tat gaa acc atc ctc cgg gag tgt ggc<br>Arg Glu Glu Leu Ala Gln Gln Tyr Glu Thr Ile Leu Arg Glu Cys Gly<br>145                            150                       155                     160 | 480 |
| cat ggc cgc ttc cag tgg aca ctc tac ttc gtg ctg ggt ctg gcg ctg<br>His Gly Arg Phe Gln Trp Thr Leu Tyr Phe Val Leu Gly Leu Ala Leu<br>                  165                     170                     175 | 528 |
| atg gca gat ggt gta gag gtc ttt gtg gtg ggc ttt gtg ctg ccc agt<br>Met Ala Asp Gly Val Glu Val Phe Val Val Gly Phe Val Leu Pro Ser<br>            180                     185                     190 | 576 |
| gct gag aaa gac atg tgc ctg tcg gac tcc aac aaa ggc atg cta ggc<br>Ala Glu Lys Asp Met Cys Leu Ser Asp Ser Asn Lys Gly Met Leu Gly<br>    195                     200                     205 | 624 |
| ctc att gtg tac ctg ggc atg atg gtg ggg gcc ttc ctc tgg gga ggc<br>Leu Ile Val Tyr Leu Gly Met Met Val Gly Ala Phe Leu Trp Gly Gly<br>210                            215                     220 | 672 |
| ctg gct gat cgg ctg ggt cgg aga cag tgt ctg ctc atc tca ctc tca<br>Leu Ala Asp Arg Leu Gly Arg Arg Gln Cys Leu Leu Ile Ser Leu Ser<br>225                            230                     235                   240 | 720 |
| gtc aac agc gtc ttc gcc ttc ttc tcg tcc ttc gtc cag ggt tat gga<br>Val Asn Ser Val Phe Ala Phe Phe Ser Ser Phe Val Gln Gly Tyr Gly<br>                  245                     250                     255 | 768 |
| acc ttt ctc ttc tgc cgc ctc ctt tcc ggg gtc ggg att ggc ggt tcc<br>Thr Phe Leu Phe Cys Arg Leu Leu Ser Gly Val Gly Ile Gly Gly Ser<br>            260                     265                     270 | 816 |
| atc ccc ata gtc ttc tcc tat ttt tcg gag ttt ctg gcg cag gag aaa<br>Ile Pro Ile Val Phe Ser Tyr Phe Ser Glu Phe Leu Ala Gln Glu Lys<br>    275                     280                     285 | 864 |
| cgt ggg gag cat ttg agc tgg ctc tgt atg ttc tgg atg atc ggt gga<br>Arg Gly Glu His Leu Ser Trp Leu Cys Met Phe Trp Met Ile Gly Gly<br>290                            295                     300 | 912 |
| gtg tat gca gct gca atg gcc tgg gcc atc atc cct cac tat ggg tgg<br>Val Tyr Ala Ala Ala Met Ala Trp Ala Ile Ile Pro His Tyr Gly Trp<br>305                            310                     315                   320 | 960 |
| agt ttc cag atg ggc tct gct tac cag ttc cac agc tgg agg gtg ttt<br>Ser Phe Gln Met Gly Ser Ala Tyr Gln Phe His Ser Trp Arg Val Phe<br>                  325                     330                     335 | 1008 |
| gtc ctc gtg tgt gcc ttt ccc tct gtg ttt gcc atc ggg gct ctg act<br>Val Leu Val Cys Ala Phe Pro Ser Val Phe Ala Ile Gly Ala Leu Thr<br>            340                     345                     350 | 1056 |
| acg cag cca gag agt ccc cgc ttc ttc cta gag aat ggg aag cat gac<br>Thr Gln Pro Glu Ser Pro Arg Phe Phe Leu Glu Asn Gly Lys His Asp<br>    355                     360                     365 | 1104 |
| gaa gcc tgg atg gta ctg aag cag gtt cac gac acc aac atg cga gcc<br>Glu Ala Trp Met Val Leu Lys Gln Val His Asp Thr Asn Met Arg Ala<br>370                            375                     380 | 1152 |
| aag ggc cac cct gag cgc gtc ttc tca gtg acc cac att aaa acg att<br>Lys Gly His Pro Glu Arg Val Phe Ser Val Thr His Ile Lys Thr Ile<br>385                            390                     395                   400 | 1200 |
| cat caa gag gat gaa ttg att gag atc cag tct gac aca gga acc tgg<br>His Gln Glu Asp Glu Leu Ile Glu Ile Gln Ser Asp Thr Gly Thr Trp<br>                  405                     410                     415 | 1248 |
| tac cag cgc tgg gga gta cgg gct ttg agc ctt ggg ggt cag gtt tgg<br>Tyr Gln Arg Trp Gly Val Arg Ala Leu Ser Leu Gly Gly Gln Val Trp<br>            420                     425                     430 | 1296 |
| ggg aat ttc ctc tcc tgc ttc agt cca gag tat cgg cgc atc acg ctg<br>Gly Asn Phe Leu Ser Cys Phe Ser Pro Glu Tyr Arg Arg Ile Thr Leu<br>    435                     440                     445 | 1344 |
| atg atg atg ggt gtg tgg ttc acc atg tct ttc agc tac tat ggt ttg<br>Met Met Met Gly Val Trp Phe Thr Met Ser Phe Ser Tyr Tyr Gly Leu<br>450                            455                     460 | 1392 |

```
act gtc tgg ttt ccc gac atg atc cgc cat ctc cag gct gtg gac tat      1440
Thr Val Trp Phe Pro Asp Met Ile Arg His Leu Gln Ala Val Asp Tyr
465                 470                 475                 480 gca gcc cga acc aaa gtg ttc cca ggg gag cgc gtg gag cat gtg acg      1488
Ala Ala Arg Thr Lys Val Phe Pro Gly Glu Arg Val Glu His Val Thr
                485                 490                 495 ttt aac ttc aca ctg gag aat cag atc cac cga ggg gga cag tac ttc      1536
Phe Asn Phe Thr Leu Glu Asn Gln Ile His Arg Gly Gly Gln Tyr Phe
            500                 505                 510 aat gac aag ttc atc ggg ctg cgt ctg aag tca gtg tcc ttt gag gat      1584
Asn Asp Lys Phe Ile Gly Leu Arg Leu Lys Ser Val Ser Phe Glu Asp
        515                 520                 525 tcc ctg ttt gag gag tgt tac ttt gaa gat gtt aca tcc agc aac aca      1632
Ser Leu Phe Glu Glu Cys Tyr Phe Glu Asp Val Thr Ser Ser Asn Thr
    530                 535                 540 ttc ttc cgc aac tgc acg ttc atc aac act gtg ttc tat aac act gac      1680
Phe Phe Arg Asn Cys Thr Phe Ile Asn Thr Val Phe Tyr Asn Thr Asp
545                 550                 555                 560 cta ttt gag tac aag ttc gtg aac agc cgg ctg gtg aac agc acg ttc      1728
Leu Phe Glu Tyr Lys Phe Val Asn Ser Arg Leu Val Asn Ser Thr Phe
                565                 570                 575 ctg cac aat aag gaa ggc tgc ccg cta gac gtg acg ggg aca ggc gaa      1776
Leu His Asn Lys Glu Gly Cys Pro Leu Asp Val Thr Gly Thr Gly Glu
            580                 585                 590 ggt gcc tac atg gtg tac ttt gtc agc ttc ttg ggg aca ctg gct gtg      1824
Gly Ala Tyr Met Val Tyr Phe Val Ser Phe Leu Gly Thr Leu Ala Val
        595                 600                 605 ctt cct gga aac att gtg tct gct ctg ctc atg gac aag att ggc agg      1872
Leu Pro Gly Asn Ile Val Ser Ala Leu Leu Met Asp Lys Ile Gly Arg
    610                 615                 620 ctc aga atg ctt gct ggt tcc agt gtg ttg tcc tgt gtg tcc tgc ttc      1920
Leu Arg Met Leu Ala Gly Ser Ser Val Leu Ser Cys Val Ser Cys Phe
625                 630                 635                 640 ttc ctg tct ttt ggg aac agc gag tca gcc atg atc gct ctg ctc tgc      1968
Phe Leu Ser Phe Gly Asn Ser Glu Ser Ala Met Ile Ala Leu Leu Cys
                645                 650                 655 ctt ttt ggg gga gtt agc atc gca tcc tgg aac gcg ctg gac gtg ctg      2016
Leu Phe Gly Gly Val Ser Ile Ala Ser Trp Asn Ala Leu Asp Val Leu
            660                 665                 670 acc gtt gag ctc tac cct tcc gac aag agg act act gcc ttt ggc ttc      2064
Thr Val Glu Leu Tyr Pro Ser Asp Lys Arg Thr Thr Ala Phe Gly Phe
        675                 680                 685 ctg aat gcc ctg tgt aag ctg gca gct gtg ctg ggg atc agc atc ttc      2112
Leu Asn Ala Leu Cys Lys Leu Ala Ala Val Leu Gly Ile Ser Ile Phe
    690                 695                 700 aca tcc ttt gtg ggc atc acc aag gct gct ccc att ctc ttt gcc tcg      2160
Thr Ser Phe Val Gly Ile Thr Lys Ala Ala Pro Ile Leu Phe Ala Ser
705                 710                 715                 720 gct gct ctt gcc ctt ggt agc tct ctg gct ctg aag ctg cct gag acc      2208
Ala Ala Leu Ala Leu Gly Ser Ser Leu Ala Leu Lys Leu Pro Glu Thr
                725                 730                 735 cgg gga cag gtg ctg cag tga                                          2229
Arg Gly Gln Val Leu Gln
            740
```

<210> SEQ ID NO 8
<211> LENGTH: 742
<212> TYPE: PRT
<213> ORGANISM: Mus musculus

<400> SEQUENCE: 8

```
Met Glu Glu Gly Phe Arg Asp Arg Ala Ala Phe Ile Arg Gly Ala Lys
1               5                   10                  15

Asp Ile Ala Lys Glu Val Lys Lys His Ala Ala Lys Lys Val Val Lys
            20                  25                  30

Gly Leu Asp Arg Val Gln Asp Glu Tyr Ser Arg Ser Tyr Ser Arg
            35                  40                  45

Phe Glu Glu Glu Asp Asp Asp Phe Pro Ala Pro Ala Asp Gly
50                  55                  60

Tyr Tyr Arg Gly Glu Gly Ala Gln Asp Glu Glu Gly Gly Ala Ser
65                  70                  75                  80

Ser Asp Ala Thr Glu Gly His Asp Glu Asp Glu Ile Tyr Glu Gly
            85                  90                  95

Glu Tyr Gln Gly Ile Pro Arg Ala Glu Ser Gly Gly Lys Gly Glu Arg
            100                 105                 110

Met Ala Asp Gly Ala Pro Leu Ala Gly Val Arg Gly Gly Leu Ser Asp
            115                 120                 125

Gly Glu Gly Pro Pro Gly Gly Arg Gly Glu Ala Gln Arg Arg Lys Asp
            130                 135                 140

Arg Glu Glu Leu Ala Gln Gln Tyr Glu Thr Ile Leu Arg Glu Cys Gly
145                 150                 155                 160

His Gly Arg Phe Gln Trp Thr Leu Tyr Phe Val Leu Gly Leu Ala Leu
                165                 170                 175

Met Ala Asp Gly Val Glu Val Phe Val Val Gly Phe Val Leu Pro Ser
            180                 185                 190

Ala Glu Lys Asp Met Cys Leu Ser Asp Ser Asn Lys Gly Met Leu Gly
            195                 200                 205

Leu Ile Val Tyr Leu Gly Met Met Val Gly Ala Phe Leu Trp Gly Gly
            210                 215                 220

Leu Ala Asp Arg Leu Gly Arg Arg Gln Cys Leu Leu Ile Ser Leu Ser
225                 230                 235                 240

Val Asn Ser Val Phe Ala Phe Phe Ser Ser Phe Val Gln Gly Tyr Gly
                245                 250                 255

Thr Phe Leu Phe Cys Arg Leu Leu Ser Gly Val Gly Ile Gly Gly Ser
                260                 265                 270

Ile Pro Ile Val Phe Ser Tyr Phe Ser Glu Phe Leu Ala Gln Glu Lys
                275                 280                 285

Arg Gly Glu His Leu Ser Trp Leu Cys Met Phe Trp Met Ile Gly Gly
            290                 295                 300

Val Tyr Ala Ala Ala Met Ala Trp Ala Ile Ile Pro His Tyr Gly Trp
305                 310                 315                 320

Ser Phe Gln Met Gly Ser Ala Tyr Gln Phe His Ser Trp Arg Val Phe
                325                 330                 335

Val Leu Val Cys Ala Phe Pro Ser Val Phe Ala Ile Gly Ala Leu Thr
                340                 345                 350

Thr Gln Pro Glu Ser Pro Arg Phe Phe Leu Glu Asn Gly Lys His Asp
            355                 360                 365

Glu Ala Trp Met Val Leu Lys Gln Val His Asp Thr Asn Met Arg Ala
            370                 375                 380

Lys Gly His Pro Glu Arg Val Phe Ser Val Thr His Ile Lys Thr Ile
385                 390                 395                 400

His Gln Glu Asp Glu Leu Ile Glu Ile Gln Ser Asp Thr Gly Thr Trp
                405                 410                 415

Tyr Gln Arg Trp Gly Val Arg Ala Leu Ser Leu Gly Gly Gln Val Trp
            420                 425                 430
```

```
Gly Asn Phe Leu Ser Cys Phe Ser Pro Glu Tyr Arg Arg Ile Thr Leu
            435                 440                 445

Met Met Met Gly Val Trp Phe Thr Met Ser Phe Ser Tyr Tyr Gly Leu
    450                 455                 460

Thr Val Trp Phe Pro Asp Met Ile Arg His Leu Gln Ala Val Asp Tyr
465                 470                 475                 480

Ala Ala Arg Thr Lys Val Phe Pro Gly Glu Arg Val Glu His Val Thr
                485                 490                 495

Phe Asn Phe Thr Leu Glu Asn Gln Ile His Arg Gly Gly Gln Tyr Phe
            500                 505                 510

Asn Asp Lys Phe Ile Gly Leu Arg Leu Lys Ser Val Ser Phe Glu Asp
        515                 520                 525

Ser Leu Phe Glu Glu Cys Tyr Phe Glu Asp Val Thr Ser Ser Asn Thr
    530                 535                 540

Phe Phe Arg Asn Cys Thr Phe Ile Asn Thr Val Phe Tyr Asn Thr Asp
545                 550                 555                 560

Leu Phe Glu Tyr Lys Phe Val Asn Ser Arg Leu Val Asn Ser Thr Phe
                565                 570                 575

Leu His Asn Lys Glu Gly Cys Pro Leu Asp Val Thr Gly Thr Gly Glu
            580                 585                 590

Gly Ala Tyr Met Val Tyr Phe Val Ser Phe Leu Gly Thr Leu Ala Val
        595                 600                 605

Leu Pro Gly Asn Ile Val Ser Ala Leu Leu Met Asp Lys Ile Gly Arg
    610                 615                 620

Leu Arg Met Leu Ala Gly Ser Val Leu Ser Cys Val Ser Cys Phe
625                 630                 635                 640

Phe Leu Ser Phe Gly Asn Ser Glu Ser Ala Met Ile Ala Leu Leu Cys
                645                 650                 655

Leu Phe Gly Gly Val Ser Ile Ala Ser Trp Asn Ala Leu Asp Val Leu
            660                 665                 670

Thr Val Glu Leu Tyr Pro Ser Asp Lys Arg Thr Thr Ala Phe Gly Phe
        675                 680                 685

Leu Asn Ala Leu Cys Lys Leu Ala Ala Val Leu Gly Ile Ser Ile Phe
    690                 695                 700

Thr Ser Phe Val Gly Ile Thr Lys Ala Ala Pro Ile Leu Phe Ala Ser
705                 710                 715                 720

Ala Ala Leu Ala Leu Gly Ser Ser Leu Ala Leu Lys Leu Pro Glu Thr
                725                 730                 735

Arg Gly Gln Val Leu Gln
            740

<210> SEQ ID NO 9
<211> LENGTH: 2052
<212> TYPE: DNA
<213> ORGANISM: Mus musculus
<220> FEATURE:
<221> NAME/KEY: CDS
<222> LOCATION: (1)..(2052)

<400> SEQUENCE: 9 atg gat gac tac agg tat cgg gac aac tat gag ggc tat gcc cct agt    48
Met Asp Asp Tyr Arg Tyr Arg Asp Asn Tyr Glu Gly Tyr Ala Pro Ser
1               5                   10                  15 gat ggc tac tac cgt agc aat gag cag aat cag gaa gaa gat gca cag    96
Asp Gly Tyr Tyr Arg Ser Asn Glu Gln Asn Gln Glu Glu Asp Ala Gln
            20                  25                  30
```

```
agc gat gtt aca gaa ggc cat gac gag gaa gat gag atc tat gaa ggc    144
Ser Asp Val Thr Glu Gly His Asp Glu Glu Asp Glu Ile Tyr Glu Gly
         35                  40                  45 gag tac caa ggc atc cct cat cca gat gat gtc aag tct aag cag acc    192
Glu Tyr Gln Gly Ile Pro His Pro Asp Asp Val Lys Ser Lys Gln Thr
     50                  55                  60 aag atg gcg ccc tcc aga gca gat ggt ctt ggg ggc cag gca gac ttg    240
Lys Met Ala Pro Ser Arg Ala Asp Gly Leu Gly Gly Gln Ala Asp Leu
 65              70                  75                  80 atg gct gag agg atg gaa gat gag gag gag ctg gct cac caa tat gag    288
Met Ala Glu Arg Met Glu Asp Glu Glu Glu Leu Ala His Gln Tyr Glu
                 85                  90                  95 acc atc att gat gag tgt ggc cat ggg cgc ttc cag tgg acc ctc ttc    336
Thr Ile Ile Asp Glu Cys Gly His Gly Arg Phe Gln Trp Thr Leu Phe
            100                 105                 110 ttc gtc ttg ggt ttg gcc ttg atg gct gat gga gtg gaa ata ttt gta    384
Phe Val Leu Gly Leu Ala Leu Met Ala Asp Gly Val Glu Ile Phe Val
        115                 120                 125 gtg agc ttt gct ctg cca agt gca gag aaa gac atg tgt ctg tcc agt    432
Val Ser Phe Ala Leu Pro Ser Ala Glu Lys Asp Met Cys Leu Ser Ser
    130                 135                 140 tcc aag aaa gga atg ctt ggg ctg ata gtc tac cta gga atg atg gca    480
Ser Lys Lys Gly Met Leu Gly Leu Ile Val Tyr Leu Gly Met Met Ala
145                 150                 155                 160 ggg gcc ttc atc ttg ggc ggc ctg gct gat aaa ctg gga agg aag aag    528
Gly Ala Phe Ile Leu Gly Gly Leu Ala Asp Lys Leu Gly Arg Lys Lys
                165                 170                 175 gtc ctc agc atg tca ctg gcc atc aat gcc tcc ttt gct tca ctc tcc    576
Val Leu Ser Met Ser Leu Ala Ile Asn Ala Ser Phe Ala Ser Leu Ser
            180                 185                 190 tcc ttc gtg cag gga tat gga gcc ttc ctc ttc tgc aga ctc atc tca    624
Ser Phe Val Gln Gly Tyr Gly Ala Phe Leu Phe Cys Arg Leu Ile Ser
        195                 200                 205 ggc ata ggg att ggg ggc tcc ctg cca att gtt ttt gcc tac ttt tct    672
Gly Ile Gly Ile Gly Gly Ser Leu Pro Ile Val Phe Ala Tyr Phe Ser
210                 215                 220 gag ttc tta tca cga gag aaa cgc ggt gag cat ctt agc tgg ctg ggc    720
Glu Phe Leu Ser Arg Glu Lys Arg Gly Glu His Leu Ser Trp Leu Gly
225                 230                 235                 240 atc ttc tgg atg act gga ggc atc tat gca tct gcc atg gcc tgg agc    768
Ile Phe Trp Met Thr Gly Gly Ile Tyr Ala Ser Ala Met Ala Trp Ser
                245                 250                 255 atc att cca cac tat ggc tgg ggc ttc agc atg ggg act aat tac cac    816
Ile Ile Pro His Tyr Gly Trp Gly Phe Ser Met Gly Thr Asn Tyr His
            260                 265                 270 ttc cac agc tgg aga gtg ttt gtc atc gtc tgt gct ctg ccc gcc act    864
Phe His Ser Trp Arg Val Phe Val Ile Val Cys Ala Leu Pro Ala Thr
        275                 280                 285 gtg tcc atg gtg gct ctg aag ttc atg cca gaa agc ccc agg ttc ctg    912
Val Ser Met Val Ala Leu Lys Phe Met Pro Glu Ser Pro Arg Phe Leu
    290                 295                 300 ctg gag atg ggc aaa cat gat gaa gcc tgg atg att ctc aaa caa gtc    960
Leu Glu Met Gly Lys His Asp Glu Ala Trp Met Ile Leu Lys Gln Val
305                 310                 315                 320 cat gat aca aac atg aga gct aag ggg acc ccg gaa aag gtg ttc acg    1008
His Asp Thr Asn Met Arg Ala Lys Gly Thr Pro Glu Lys Val Phe Thr
                325                 330                 335 gtt tcc cac atc aaa act ccc aag caa atg gat gaa ttc att gag ata    1056
Val Ser His Ile Lys Thr Pro Lys Gln Met Asp Glu Phe Ile Glu Ile
            340                 345                 350
```

```
cag agc tca acc gga act tgg tac cag cgc tgg ctg gtc agg ttc atg       1104
Gln Ser Ser Thr Gly Thr Trp Tyr Gln Arg Trp Leu Val Arg Phe Met
        355                 360                 365 acc att ttc aaa cag gtc tgg gat aac gcc ttg tac tgt gtg atg ggg       1152
Thr Ile Phe Lys Gln Val Trp Asp Asn Ala Leu Tyr Cys Val Met Gly
            370                 375                 380 ccc tac aga atg aac acc ctg att ctg gct gtc tgg ttc acc atg           1200
Pro Tyr Arg Met Asn Thr Leu Ile Leu Ala Val Val Trp Phe Thr Met
385                 390                 395                 400 gcc tta agt tac tac ggc ctg acg gtg tgg ttc ccc gac atg atc cgc       1248
Ala Leu Ser Tyr Tyr Gly Leu Thr Val Trp Phe Pro Asp Met Ile Arg
                405                 410                 415 tat ttc cag gat gaa gaa tat aag tct aaa atg aag gtg ttt ttt ggt       1296
Tyr Phe Gln Asp Glu Glu Tyr Lys Ser Lys Met Lys Val Phe Phe Gly
            420                 425                 430 gag cac gtg cat ggc gcc acg atc aac ttt acc atg gaa aac cag atc       1344
Glu His Val His Gly Ala Thr Ile Asn Phe Thr Met Glu Asn Gln Ile
                435                 440                 445 cac caa cat ggg aag ctt gtg aac gat aag ttc ata aag atg tat ttt       1392
His Gln His Gly Lys Leu Val Asn Asp Lys Phe Ile Lys Met Tyr Phe
450                 455                 460 aaa cat gtc ctc ttt gag gac aca ttc ttt gac aaa tgc tat ttt gaa       1440
Lys His Val Leu Phe Glu Asp Thr Phe Phe Asp Lys Cys Tyr Phe Glu
465                 470                 475                 480 gat gtg aca tcc aca gat acg tat ttc aag aac tgc acc atc gaa tcg       1488
Asp Val Thr Ser Thr Asp Thr Tyr Phe Lys Asn Cys Thr Ile Glu Ser
                485                 490                 495 acc acc ttc tac aac aca gac ctc tac aaa cac aag ttc atc aac tgt       1536
Thr Thr Phe Tyr Asn Thr Asp Leu Tyr Lys His Lys Phe Ile Asn Cys
            500                 505                 510 cgg ttt atc aat tcc acc ttt ctg gag cag aag gag ggc tgc cac atg       1584
Arg Phe Ile Asn Ser Thr Phe Leu Glu Gln Lys Glu Gly Cys His Met
        515                 520                 525 gac ttt gaa gag gac aat gat ttt ctg att tac ctc gtc agc ttc ctc       1632
Asp Phe Glu Glu Asp Asn Asp Phe Leu Ile Tyr Leu Val Ser Phe Leu
    530                 535                 540 ggc agc ctc tct gtc ttg cct ggg aac ata att tct gcc ctg ctc atg       1680
Gly Ser Leu Ser Val Leu Pro Gly Asn Ile Ile Ser Ala Leu Leu Met
545                 550                 555                 560 gac aga att gga aga ctc aag atg att ggc ggc tcc atg ctc atc tct       1728
Asp Arg Ile Gly Arg Leu Lys Met Ile Gly Gly Ser Met Leu Ile Ser
                565                 570                 575 gca gtc tgc tgc ttc ttc ctg ttt ttt ggc aac agc gag tct gcg atg       1776
Ala Val Cys Cys Phe Phe Leu Phe Phe Gly Asn Ser Glu Ser Ala Met
            580                 585                 590 atc ggc tgg caa tgc ctg ttc tgt ggg acc agc att gca gcc tgg aat       1824
Ile Gly Trp Gln Cys Leu Phe Cys Gly Thr Ser Ile Ala Ala Trp Asn
        595                 600                 605 gct ctg gat gtg atc aca gtt gag ctg tat ccc acc aac cag agg gcc       1872
Ala Leu Asp Val Ile Thr Val Glu Leu Tyr Pro Thr Asn Gln Arg Ala
    610                 615                 620 acg gcc ttc ggc atc ctc aac gga ctg tgc aag ttt ggg gcc atc ctg       1920
Thr Ala Phe Gly Ile Leu Asn Gly Leu Cys Lys Phe Gly Ala Ile Leu
625                 630                 635                 640 gga aac act atc ttt gct tct ttt gtt ggg ata acc aaa gtg gtc ccc       1968
Gly Asn Thr Ile Phe Ala Ser Phe Val Gly Ile Thr Lys Val Val Pro
                645                 650                 655 atc ctt ctg gct gct gct tct ctg gtt gga ggt ggc ctg att gcc ctt       2016
Ile Leu Leu Ala Ala Ala Ser Leu Val Gly Gly Gly Leu Ile Ala Leu
            660                 665                 670
```

```
cga ttg cca gag act cga gag caa gtc ctg atg tga                        2052
Arg Leu Pro Glu Thr Arg Glu Gln Val Leu Met
        675                 680
```

<210> SEQ ID NO 10
<211> LENGTH: 683
<212> TYPE: PRT
<213> ORGANISM: Mus musculus

<400> SEQUENCE: 10

```
Met Asp Asp Tyr Arg Tyr Arg Asp Asn Tyr Glu Gly Tyr Ala Pro Ser
1               5                   10                  15

Asp Gly Tyr Tyr Arg Ser Asn Glu Gln Asn Gln Glu Glu Asp Ala Gln
            20                  25                  30

Ser Asp Val Thr Glu Gly His Asp Glu Glu Asp Glu Ile Tyr Glu Gly
        35                  40                  45

Glu Tyr Gln Gly Ile Pro His Pro Asp Asp Val Lys Ser Lys Gln Thr
    50                  55                  60

Lys Met Ala Pro Ser Arg Ala Asp Gly Leu Gly Gln Ala Asp Leu
65                  70                  75                  80

Met Ala Glu Arg Met Glu Asp Glu Glu Leu Ala His Gln Tyr Glu
                85                  90                  95

Thr Ile Ile Asp Glu Cys Gly His Gly Arg Phe Gln Trp Thr Leu Phe
            100                 105                 110

Phe Val Leu Gly Leu Ala Leu Met Ala Asp Gly Val Glu Ile Phe Val
        115                 120                 125

Val Ser Phe Ala Leu Pro Ser Ala Glu Lys Asp Met Cys Leu Ser Ser
130                 135                 140

Ser Lys Lys Gly Met Leu Gly Leu Ile Val Tyr Leu Gly Met Met Ala
145                 150                 155                 160

Gly Ala Phe Ile Leu Gly Gly Leu Ala Asp Lys Leu Gly Arg Lys Lys
                165                 170                 175

Val Leu Ser Met Ser Leu Ala Ile Asn Ala Ser Phe Ala Ser Leu Ser
            180                 185                 190

Ser Phe Val Gln Gly Tyr Gly Ala Phe Leu Phe Cys Arg Leu Ile Ser
        195                 200                 205

Gly Ile Gly Ile Gly Gly Ser Leu Pro Ile Val Phe Ala Tyr Phe Ser
    210                 215                 220

Glu Phe Leu Ser Arg Glu Lys Arg Gly Glu His Leu Ser Trp Leu Gly
225                 230                 235                 240

Ile Phe Trp Met Thr Gly Gly Ile Tyr Ala Ser Ala Met Ala Trp Ser
                245                 250                 255

Ile Ile Pro His Tyr Gly Trp Gly Phe Ser Met Gly Thr Asn Tyr His
            260                 265                 270

Phe His Ser Trp Arg Val Phe Val Ile Val Cys Ala Leu Pro Ala Thr
        275                 280                 285

Val Ser Met Val Ala Leu Lys Phe Met Pro Glu Ser Pro Arg Phe Leu
    290                 295                 300

Leu Glu Met Gly Lys His Asp Glu Ala Trp Met Ile Leu Lys Gln Val
305                 310                 315                 320

His Asp Thr Asn Met Arg Ala Lys Gly Thr Pro Glu Lys Val Phe Thr
                325                 330                 335

Val Ser His Ile Lys Thr Pro Lys Gln Met Asp Glu Phe Ile Glu Ile
            340                 345                 350

Gln Ser Ser Thr Gly Thr Trp Tyr Gln Arg Trp Leu Val Arg Phe Met
        355                 360                 365
```

```
Thr Ile Phe Lys Gln Val Trp Asp Asn Ala Leu Tyr Cys Val Met Gly
        370                 375                 380

Pro Tyr Arg Met Asn Thr Leu Ile Leu Ala Val Val Trp Phe Thr Met
385                 390                 395                 400

Ala Leu Ser Tyr Tyr Gly Leu Thr Val Trp Phe Pro Asp Met Ile Arg
                405                 410                 415

Tyr Phe Gln Asp Glu Glu Tyr Lys Ser Lys Met Lys Val Phe Phe Gly
                420                 425                 430

Glu His Val His Gly Ala Thr Ile Asn Phe Thr Met Glu Asn Gln Ile
                435                 440                 445

His Gln His Gly Lys Leu Val Asn Asp Lys Phe Ile Lys Met Tyr Phe
        450                 455                 460

Lys His Val Leu Phe Glu Asp Thr Phe Asp Lys Cys Tyr Phe Glu
465                 470                 475                 480

Asp Val Thr Ser Thr Asp Thr Tyr Phe Lys Asn Cys Thr Ile Glu Ser
                485                 490                 495

Thr Thr Phe Tyr Asn Thr Asp Leu Tyr Lys His Lys Phe Ile Asn Cys
                500                 505                 510

Arg Phe Ile Asn Ser Thr Phe Leu Glu Gln Lys Glu Gly Cys His Met
        515                 520                 525

Asp Phe Glu Glu Asp Asn Asp Phe Leu Ile Tyr Leu Val Ser Phe Leu
                530                 535                 540

Gly Ser Leu Ser Val Leu Pro Gly Asn Ile Ile Ser Ala Leu Leu Met
545                 550                 555                 560

Asp Arg Ile Gly Arg Leu Lys Met Ile Gly Gly Ser Met Leu Ile Ser
                565                 570                 575

Ala Val Cys Cys Phe Phe Leu Phe Phe Gly Asn Ser Glu Ser Ala Met
                580                 585                 590

Ile Gly Trp Gln Cys Leu Phe Cys Gly Thr Ser Ile Ala Ala Trp Asn
        595                 600                 605

Ala Leu Asp Val Ile Thr Val Glu Leu Tyr Pro Thr Asn Gln Arg Ala
610                 615                 620

Thr Ala Phe Gly Ile Leu Asn Gly Leu Cys Lys Phe Gly Ala Ile Leu
625                 630                 635                 640

Gly Asn Thr Ile Phe Ala Ser Phe Val Gly Ile Thr Lys Val Val Pro
                645                 650                 655

Ile Leu Leu Ala Ala Ala Ser Leu Val Gly Gly Leu Ile Ala Leu
                660                 665                 670

Arg Leu Pro Glu Thr Arg Glu Gln Val Leu Met
        675                 680

<210> SEQ ID NO 11
<211> LENGTH: 2184
<212> TYPE: DNA
<213> ORGANISM: Mus musculus
<220> FEATURE:
<221> NAME/KEY: CDS
<222> LOCATION: (1)..(2181)

<400> SEQUENCE: 11 atg gaa gac tcc tac aag gat agg act tca ctg atg aag ggt gcc aag    48
Met Glu Asp Ser Tyr Lys Asp Arg Thr Ser Leu Met Lys Gly Ala Lys
1               5                   10                  15 gac att gcc aaa gag gtg aag aag cag acg gtg aag aag gtg aac cag    96
Asp Ile Ala Lys Glu Val Lys Lys Gln Thr Val Lys Lys Val Asn Gln
            20                  25                  30
```

| | | |
|---|---|---|
| gca gtg gat cgg gcc cag gat gaa tat acc cag cgg tcc tac agt cgg<br>Ala Val Asp Arg Ala Gln Asp Glu Tyr Thr Gln Arg Ser Tyr Ser Arg<br>     35                   40                   45 | | 144 |
| ttc cag gat gaa gag gac gat gat gac tac tac cca cct ggc gaa acc<br>Phe Gln Asp Glu Glu Asp Asp Asp Asp Tyr Tyr Pro Pro Gly Glu Thr<br> 50                      55                     60 | | 192 |
| tac agt ggg gag gtc aat gat gat gaa ggc tca agt gag gcc act gag<br>Tyr Ser Gly Glu Val Asn Asp Asp Glu Gly Ser Ser Glu Ala Thr Glu<br>65                    70                   75                    80 | | 240 |
| ggt cac gac gag gag gat gag atc tat gaa ggg gag tac cag ggc atc<br>Gly His Asp Glu Glu Asp Glu Ile Tyr Glu Gly Glu Tyr Gln Gly Ile<br>                 85                   90                   95 | | 288 |
| ccc agc acg aac cag ggg aaa gac agc atc gtg tct gta gga cag ccc<br>Pro Ser Thr Asn Gln Gly Lys Asp Ser Ile Val Ser Val Gly Gln Pro<br>            100                 105                110 | | 336 |
| aaa ggt gat gag tac aag gac cgc aga gag cta gag tca gag agg agg<br>Lys Gly Asp Glu Tyr Lys Asp Arg Arg Glu Leu Glu Ser Glu Arg Arg<br>         115                  120               125 | | 384 |
| gct gat gag gaa gag ctc gcc cag cag tat gag ctg ata atc caa gag<br>Ala Asp Glu Glu Glu Leu Ala Gln Gln Tyr Glu Leu Ile Ile Gln Glu<br> 130                    135                140 | | 432 |
| tgt ggc cac ggc cgt ttc cag tgg gcc ctt ttc ttc gtc ctg ggc atg<br>Cys Gly His Gly Arg Phe Gln Trp Ala Leu Phe Phe Val Leu Gly Met<br>145                    150                   155                160 | | 480 |
| gct ctc atg gcc gat ggc gtg gag gtg ttt gtg gtg ggc ttc gtg cta<br>Ala Leu Met Ala Asp Gly Val Glu Val Phe Val Val Gly Phe Val Leu<br>                 165                   170                175 | | 528 |
| ccc agt gca gag aca gac cta tgc ata cca aat tcg gga tct gga tgg<br>Pro Ser Ala Glu Thr Asp Leu Cys Ile Pro Asn Ser Gly Ser Gly Trp<br>            180                 185                190 | | 576 |
| cta ggt agc ata gtg tac ctc ggg atg atg gtg ggg gcg ttc ttc tgg<br>Leu Gly Ser Ile Val Tyr Leu Gly Met Met Val Gly Ala Phe Phe Trp<br>         195                  200               205 | | 624 |
| gga gga ctg gca gac aaa gta gga agg aag cag tct ctt ctg att tgc<br>Gly Gly Leu Ala Asp Lys Val Gly Arg Lys Gln Ser Leu Leu Ile Cys<br> 210                    215                220 | | 672 |
| atg tct gtc aac gga ttc ttt gcc ttc ctc tcc tca ttt gtc caa ggt<br>Met Ser Val Asn Gly Phe Phe Ala Phe Leu Ser Ser Phe Val Gln Gly<br>225                    230                   235                240 | | 720 |
| tac ggc ttc ttt ctc gtc tgt cgg ttg ctt tct gga ttc ggg att gga<br>Tyr Gly Phe Phe Leu Val Cys Arg Leu Leu Ser Gly Phe Gly Ile Gly<br>                 245                   250                255 | | 768 |
| ggc gcc att ccc act gtg ttc tcc tac ttc gct gaa gtc ctg gcc cgg<br>Gly Ala Ile Pro Thr Val Phe Ser Tyr Phe Ala Glu Val Leu Ala Arg<br>            260                 265                270 | | 816 |
| gag aag cgg ggt gag cac ctc agt tgg ctc tgc atg ttc tgg atg att<br>Glu Lys Arg Gly Glu His Leu Ser Trp Leu Cys Met Phe Trp Met Ile<br>         275                  280               285 | | 864 |
| ggc ggc atc tac gcc tcc gcc atg gcc tgg gcc atc att ccc cac tac<br>Gly Gly Ile Tyr Ala Ser Ala Met Ala Trp Ala Ile Ile Pro His Tyr<br> 290                    295                300 | | 912 |
| ggg tgg agc ttc agc atg ggt tca gcc tac cag ttc cac agc tgg cgc<br>Gly Trp Ser Phe Ser Met Gly Ser Ala Tyr Gln Phe His Ser Trp Arg<br>305                    310                   315                320 | | 960 |
| gtc ttc gtc atc gtc tgt gcg ctc ccg tgc gtc tcc tct gtg gtg gct<br>Val Phe Val Ile Val Cys Ala Leu Pro Cys Val Ser Ser Val Val Ala<br>                 325                   330                335 | | 1008 |
| ctc acc ttc atg cca gaa agc cct cgg ttc ttg ctg gag gtg gga aaa<br>Leu Thr Phe Met Pro Glu Ser Pro Arg Phe Leu Leu Glu Val Gly Lys<br>            340                 345                350 | | 1056 |

```
cat gat gaa gcc tgg atg att ctg aag tta att cat gac acc aac atg     1104
His Asp Glu Ala Trp Met Ile Leu Lys Leu Ile His Asp Thr Asn Met
        355                 360                 365 aga gcc cgg ggc cag cca gag aag gtc ttc acg gta aat aaa atc aag     1152
Arg Ala Arg Gly Gln Pro Glu Lys Val Phe Thr Val Asn Lys Ile Lys
    370                 375                 380 act ccc aaa caa ata gat gag ctg atc gaa att gag agc gac acg gga     1200
Thr Pro Lys Gln Ile Asp Glu Leu Ile Glu Ile Glu Ser Asp Thr Gly
385                 390                 395                 400 acc tgg tac agg agg tgt ttc gtt cgg atc cgc acc gaa ctg tac gga     1248
Thr Trp Tyr Arg Arg Cys Phe Val Arg Ile Arg Thr Glu Leu Tyr Gly
                405                 410                 415 att tgg ctg aca ttc atg aga tgc ttc aac tac cca gtc agg gaa aac     1296
Ile Trp Leu Thr Phe Met Arg Cys Phe Asn Tyr Pro Val Arg Glu Asn
        420                 425                 430 acc atc aag ctt acg att gtc tgg ttc acc ctg tcc ttc ggg tac tat     1344
Thr Ile Lys Leu Thr Ile Val Trp Phe Thr Leu Ser Phe Gly Tyr Tyr
    435                 440                 445 ggg ttg tcc gtt tgg ttc cct gat gtc att aaa cat ctc cag tct gat     1392
Gly Leu Ser Val Trp Phe Pro Asp Val Ile Lys His Leu Gln Ser Asp
450                 455                 460 gag tat gca ctg cta act agg aat gtg caa aag gat aaa tat gca aac     1440
Glu Tyr Ala Leu Leu Thr Arg Asn Val Gln Lys Asp Lys Tyr Ala Asn
465                 470                 475                 480 ttc agc att aac ttt acc atg gag aac cag atc cac act gga atg gaa     1488
Phe Ser Ile Asn Phe Thr Met Glu Asn Gln Ile His Thr Gly Met Glu
                485                 490                 495 tac gag aac ggc aga ttc ctc gga gtc aag ttc aaa tcg gta acc ttc     1536
Tyr Glu Asn Gly Arg Phe Leu Gly Val Lys Phe Lys Ser Val Thr Phe
        500                 505                 510 aaa gat tca gtg ttt aag tcc tgc acc ttt gac gac gtg acc tca gtc     1584
Lys Asp Ser Val Phe Lys Ser Cys Thr Phe Asp Asp Val Thr Ser Val
    515                 520                 525 aac acc tac ttc aag aac tgc acg ttt att gat acc ctt ttt gat aac     1632
Asn Thr Tyr Phe Lys Asn Cys Thr Phe Ile Asp Thr Leu Phe Asp Asn
530                 535                 540 aca gat ttt gag ccc tat aaa ttc ata gac agt gaa ttt cag aac tgc     1680
Thr Asp Phe Glu Pro Tyr Lys Phe Ile Asp Ser Glu Phe Gln Asn Cys
545                 550                 555                 560 tca ttt ctt cac aat aag acg ggg tgc cag att act ttt gat gac gac     1728
Ser Phe Leu His Asn Lys Thr Gly Cys Gln Ile Thr Phe Asp Asp Asp
                565                 570                 575 tat agt gcc tac tgg att tac ttt gtc aac ttt ctt ggg aca ttg gca     1776
Tyr Ser Ala Tyr Trp Ile Tyr Phe Val Asn Phe Leu Gly Thr Leu Ala
        580                 585                 590 gtg ttg cca gga aat atc gtg tct gct ctc ctg atg gac agg atc ggg     1824
Val Leu Pro Gly Asn Ile Val Ser Ala Leu Leu Met Asp Arg Ile Gly
    595                 600                 605 cgt tta acg atg cta gga ggc tcc atg gtg ctc tcc ggg atc agt tgc     1872
Arg Leu Thr Met Leu Gly Gly Ser Met Val Leu Ser Gly Ile Ser Cys
610                 615                 620 ttc ttc ctg tgg ttt ggc acc agc gaa tcc atg atg ata ggc atg ctg     1920
Phe Phe Leu Trp Phe Gly Thr Ser Glu Ser Met Met Ile Gly Met Leu
625                 630                 635                 640 tgc ttg tat aat ggg ctg acc atc tca gcg tgg aat tct ctc gat gtc     1968
Cys Leu Tyr Asn Gly Leu Thr Ile Ser Ala Trp Asn Ser Leu Asp Val
                645                 650                 655 gtc acg gtg gaa ctg tat ccc aca gac cgg aga gca acg ggc ttc ggc     2016
Val Thr Val Glu Leu Tyr Pro Thr Asp Arg Arg Ala Thr Gly Phe Gly
        660                 665                 670
```

```
ttc ttg aac gcc ctc tgt aaa gcg gcg gcc gtc ctg gga aac tta atc     2064
Phe Leu Asn Ala Leu Cys Lys Ala Ala Ala Val Leu Gly Asn Leu Ile
        675                 680                 685 ttc ggc tcc ttg gtc agc atc acc aaa gcc atc ccc atc ctg ctg gct     2112
Phe Gly Ser Leu Val Ser Ile Thr Lys Ala Ile Pro Ile Leu Leu Ala
690                 695                 700 tcc act gtg ctc gtg tgt gga gga ctc gtg ggg ctg cgc ctg ccc gac     2160
Ser Thr Val Leu Val Cys Gly Gly Leu Val Gly Leu Arg Leu Pro Asp
705                 710                 715                 720 aca cga acc cag gtt ctg atg tga                                     2184
Thr Arg Thr Gln Val Leu Met
                725
```

```
<210> SEQ ID NO 12
<211> LENGTH: 727
<212> TYPE: PRT
<213> ORGANISM: Mus musculus

<400> SEQUENCE: 12

Met Glu Asp Ser Tyr Lys Asp Arg Thr Ser Leu Met Lys Gly Ala Lys
1               5                   10                  15

Asp Ile Ala Lys Glu Val Lys Lys Gln Thr Val Lys Lys Val Asn Gln
            20                  25                  30

Ala Val Asp Arg Ala Gln Asp Glu Tyr Thr Gln Arg Ser Tyr Ser Arg
        35                  40                  45

Phe Gln Asp Glu Glu Asp Asp Asp Tyr Tyr Pro Pro Gly Glu Thr
    50                  55                  60

Tyr Ser Gly Glu Val Asn Asp Asp Glu Gly Ser Ser Glu Ala Thr Glu
65                  70                  75                  80

Gly His Asp Glu Glu Asp Glu Ile Tyr Glu Gly Glu Tyr Gln Gly Ile
                85                  90                  95

Pro Ser Thr Asn Gln Gly Lys Asp Ser Ile Val Ser Val Gly Gln Pro
            100                 105                 110

Lys Gly Asp Glu Tyr Lys Asp Arg Arg Glu Leu Glu Ser Glu Arg Arg
        115                 120                 125

Ala Asp Glu Glu Leu Ala Gln Gln Tyr Glu Leu Ile Ile Gln Glu
    130                 135                 140

Cys Gly His Gly Arg Phe Gln Trp Ala Leu Phe Val Leu Gly Met
145                 150                 155                 160

Ala Leu Met Ala Asp Gly Val Glu Val Phe Val Gly Phe Val Leu
                165                 170                 175

Pro Ser Ala Glu Thr Asp Leu Cys Ile Pro Asn Ser Gly Ser Gly Trp
            180                 185                 190

Leu Gly Ser Ile Val Tyr Leu Gly Met Met Val Gly Ala Phe Phe Trp
        195                 200                 205

Gly Gly Leu Ala Asp Lys Val Gly Arg Lys Gln Ser Leu Leu Ile Cys
    210                 215                 220

Met Ser Val Asn Gly Phe Phe Ala Phe Leu Ser Ser Phe Val Gln Gly
225                 230                 235                 240

Tyr Gly Phe Phe Leu Val Cys Arg Leu Leu Ser Gly Phe Gly Ile Gly
                245                 250                 255

Gly Ala Ile Pro Thr Val Phe Ser Tyr Phe Ala Glu Val Leu Ala Arg
            260                 265                 270

Glu Lys Arg Gly Glu His Leu Ser Trp Leu Cys Met Phe Trp Met Ile
        275                 280                 285

Gly Gly Ile Tyr Ala Ser Ala Met Ala Trp Ala Ile Ile Pro His Tyr
    290                 295                 300
```

```
Gly Trp Ser Phe Ser Met Gly Ser Ala Tyr Gln Phe His Ser Trp Arg
305                 310                 315                 320

Val Phe Val Ile Val Cys Ala Leu Pro Cys Val Ser Ser Val Val Ala
                325                 330                 335

Leu Thr Phe Met Pro Glu Ser Pro Arg Phe Leu Leu Glu Val Gly Lys
            340                 345                 350

His Asp Glu Ala Trp Met Ile Leu Lys Leu Ile His Asp Thr Asn Met
        355                 360                 365

Arg Ala Arg Gly Gln Pro Glu Lys Val Phe Thr Val Asn Lys Ile Lys
    370                 375                 380

Thr Pro Lys Gln Ile Asp Glu Leu Ile Glu Ile Glu Ser Asp Thr Gly
385                 390                 395                 400

Thr Trp Tyr Arg Arg Cys Phe Val Arg Ile Arg Thr Glu Leu Tyr Gly
                405                 410                 415

Ile Trp Leu Thr Phe Met Arg Cys Phe Asn Tyr Pro Val Arg Glu Asn
            420                 425                 430

Thr Ile Lys Leu Thr Ile Val Trp Phe Thr Leu Ser Phe Gly Tyr Tyr
        435                 440                 445

Gly Leu Ser Val Trp Phe Pro Asp Val Ile Lys His Leu Gln Ser Asp
    450                 455                 460

Glu Tyr Ala Leu Leu Thr Arg Asn Val Gln Lys Asp Lys Tyr Ala Asn
465                 470                 475                 480

Phe Ser Ile Asn Phe Thr Met Glu Asn Gln Ile His Thr Gly Met Glu
                485                 490                 495

Tyr Glu Asn Gly Arg Phe Leu Gly Val Lys Phe Lys Ser Val Thr Phe
            500                 505                 510

Lys Asp Ser Val Phe Lys Ser Cys Thr Phe Asp Asp Val Thr Ser Val
        515                 520                 525

Asn Thr Tyr Phe Lys Asn Cys Thr Phe Ile Asp Thr Leu Phe Asp Asn
    530                 535                 540

Thr Asp Phe Glu Pro Tyr Lys Phe Ile Asp Ser Glu Phe Gln Asn Cys
545                 550                 555                 560

Ser Phe Leu His Asn Lys Thr Gly Cys Gln Ile Thr Phe Asp Asp Asp
                565                 570                 575

Tyr Ser Ala Tyr Trp Ile Tyr Phe Val Asn Phe Leu Gly Thr Leu Ala
            580                 585                 590

Val Leu Pro Gly Asn Ile Val Ser Ala Leu Leu Met Asp Arg Ile Gly
        595                 600                 605

Arg Leu Thr Met Leu Gly Gly Ser Met Val Leu Ser Gly Ile Ser Cys
    610                 615                 620

Phe Phe Leu Trp Phe Gly Thr Ser Glu Ser Met Met Ile Gly Met Leu
625                 630                 635                 640

Cys Leu Tyr Asn Gly Leu Thr Ile Ser Ala Trp Asn Ser Leu Asp Val
                645                 650                 655

Val Thr Val Glu Leu Tyr Pro Thr Asp Arg Arg Ala Thr Gly Phe Gly
            660                 665                 670

Phe Leu Asn Ala Leu Cys Lys Ala Ala Ala Val Leu Gly Asn Leu Ile
        675                 680                 685

Phe Gly Ser Leu Val Ser Ile Thr Lys Ala Ile Pro Ile Leu Leu Ala
    690                 695                 700

Ser Thr Val Leu Val Cys Gly Gly Leu Val Gly Leu Arg Leu Pro Asp
705                 710                 715                 720

Thr Arg Thr Gln Val Leu Met
```

<210> SEQ ID NO 13
<211> LENGTH: 2229
<212> TYPE: DNA
<213> ORGANISM: Homo sapiens
<220> FEATURE:
<221> NAME/KEY: CDS
<222> LOCATION: (1)..(2229)

<400> SEQUENCE: 13

| | | | | | | | | | | | | | | | | |
|---|---|---|---|---|---|---|---|---|---|---|---|---|---|---|---|---|
| atg | gaa | gag | ggc | ttc | cga | gac | cgg | gca | gct | ttc | atc | cgt | ggg | gcc | aaa | 48 |
| Met | Glu | Glu | Gly | Phe | Arg | Asp | Arg | Ala | Ala | Phe | Ile | Arg | Gly | Ala | Lys | |
| 1 | | | | 5 | | | | | 10 | | | | | 15 | | |
| gac | att | gct | aag | gaa | gtc | aaa | aag | cat | gcg | gcc | aag | aag | gtg | gtg | aag | 96 |
| Asp | Ile | Ala | Lys | Glu | Val | Lys | Lys | His | Ala | Ala | Lys | Lys | Val | Val | Lys | |
| | | | 20 | | | | | 25 | | | | | 30 | | | |
| ggc | ctg | gac | aga | gtc | cag | gac | gaa | tat | tcc | cga | aga | tcg | tac | tcc | cgc | 144 |
| Gly | Leu | Asp | Arg | Val | Gln | Asp | Glu | Tyr | Ser | Arg | Arg | Ser | Tyr | Ser | Arg | |
| | 35 | | | | | 40 | | | | | 45 | | | | | |
| ttt | gag | gag | gag | gat | gat | gat | gat | gac | ttc | cct | gct | ccc | agt | gat | ggt | 192 |
| Phe | Glu | Glu | Glu | Asp | Asp | Asp | Asp | Asp | Phe | Pro | Ala | Pro | Ser | Asp | Gly | |
| 50 | | | | | 55 | | | | | 60 | | | | | | |
| tat | tac | cga | gga | gaa | ggg | acc | cag | gat | gag | gag | gaa | ggt | ggt | gca | tcc | 240 |
| Tyr | Tyr | Arg | Gly | Glu | Gly | Thr | Gln | Asp | Glu | Glu | Glu | Gly | Gly | Ala | Ser | |
| 65 | | | | | 70 | | | | | 75 | | | | | 80 | |
| agt | gat | gct | act | gag | ggc | cat | gac | gag | gat | gat | gag | atc | tat | gaa | ggg | 288 |
| Ser | Asp | Ala | Thr | Glu | Gly | His | Asp | Glu | Asp | Asp | Glu | Ile | Tyr | Glu | Gly | |
| | | | | 85 | | | | | 90 | | | | | 95 | | |
| gaa | tat | cag | gac | att | ccc | cgg | gca | gag | tct | ggg | ggc | aaa | ggc | gag | cgg | 336 |
| Glu | Tyr | Gln | Asp | Ile | Pro | Arg | Ala | Glu | Ser | Gly | Gly | Lys | Gly | Glu | Arg | |
| | | | 100 | | | | | 105 | | | | | 110 | | | |
| atg | gca | gat | ggg | gcg | ccc | ctg | gct | gga | gta | agg | ggg | ggc | ttg | agt | gat | 384 |
| Met | Ala | Asp | Gly | Ala | Pro | Leu | Ala | Gly | Val | Arg | Gly | Gly | Leu | Ser | Asp | |
| | 115 | | | | | 120 | | | | | 125 | | | | | |
| ggg | gag | ggt | ccc | cct | ggg | ggc | cgg | ggg | gag | gca | caa | cga | cgg | aaa | gaa | 432 |
| Gly | Glu | Gly | Pro | Pro | Gly | Gly | Arg | Gly | Glu | Ala | Gln | Arg | Arg | Lys | Glu | |
| 130 | | | | | 135 | | | | | 140 | | | | | | |
| cga | gaa | gaa | ctg | gcc | caa | cag | tat | gaa | gcc | atc | cta | cgg | gag | tgt | ggc | 480 |
| Arg | Glu | Glu | Leu | Ala | Gln | Gln | Tyr | Glu | Ala | Ile | Leu | Arg | Glu | Cys | Gly | |
| 145 | | | | | 150 | | | | | 155 | | | | | 160 | |
| cac | ggc | cgc | ttc | cag | tgg | aca | ctg | tat | ttt | gtg | ctt | ggt | ctg | gcg | ctg | 528 |
| His | Gly | Arg | Phe | Gln | Trp | Thr | Leu | Tyr | Phe | Val | Leu | Gly | Leu | Ala | Leu | |
| | | | | 165 | | | | | 170 | | | | | 175 | | |
| atg | gct | gac | ggt | gtg | gag | gtc | ttt | gtg | gtg | ggc | ttc | gtg | ctg | ccc | agc | 576 |
| Met | Ala | Asp | Gly | Val | Glu | Val | Phe | Val | Val | Gly | Phe | Val | Leu | Pro | Ser | |
| | | | 180 | | | | | 185 | | | | | 190 | | | |
| gct | gag | aaa | gac | atg | tgc | ctg | tcc | gac | tcc | aac | aaa | ggc | atg | cta | ggc | 624 |
| Ala | Glu | Lys | Asp | Met | Cys | Leu | Ser | Asp | Ser | Asn | Lys | Gly | Met | Leu | Gly | |
| | 195 | | | | | 200 | | | | | 205 | | | | | |
| ctc | atc | gtc | tac | ctg | gga | atg | atg | gtg | gga | gcc | ttc | ctc | tgg | gga | ggt | 672 |
| Leu | Ile | Val | Tyr | Leu | Gly | Met | Met | Val | Gly | Ala | Phe | Leu | Trp | Gly | Gly | |
| 210 | | | | | 215 | | | | | 220 | | | | | | |
| ctg | gct | gac | cgg | ctg | ggt | cgg | agg | cag | tgt | ctg | ctc | atc | tcg | ctc | tca | 720 |
| Leu | Ala | Asp | Arg | Leu | Gly | Arg | Arg | Gln | Cys | Leu | Leu | Ile | Ser | Leu | Ser | |
| 225 | | | | | 230 | | | | | 235 | | | | | 240 | |
| gtc | aac | agc | gtc | ttc | gcc | ttc | ttc | tca | tct | ttt | gtc | cag | ggt | tac | ggc | 768 |
| Val | Asn | Ser | Val | Phe | Ala | Phe | Phe | Ser | Ser | Phe | Val | Gln | Gly | Tyr | Gly | |
| | | | | 245 | | | | | 250 | | | | | 255 | | |
| act | ttc | ctc | ttc | tgc | cgc | cta | ctt | tct | ggg | gtt | ggg | att | gga | ggg | tcc | 816 |
| Thr | Phe | Leu | Phe | Cys | Arg | Leu | Leu | Ser | Gly | Val | Gly | Ile | Gly | Gly | Ser | |
| | | | 260 | | | | | 265 | | | | | 270 | | | |

| | | |
|---|---|---|
| atc ccc att gtc ttc tcc tat ttc tcc gag ttt ctg gcc cag gag aaa<br>Ile Pro Ile Val Phe Ser Tyr Phe Ser Glu Phe Leu Ala Gln Glu Lys<br>275 280 285 | | 864 |
| cga ggg gag cat ttg agc tgg ctc tgc atg ttt tgg atg att ggt ggc<br>Arg Gly Glu His Leu Ser Trp Leu Cys Met Phe Trp Met Ile Gly Gly<br>290 295 300 | | 912 |
| gtg tac gca gct gct atg gcc tgg gcc atc atc ccc cac tat ggg tgg<br>Val Tyr Ala Ala Ala Met Ala Trp Ala Ile Ile Pro His Tyr Gly Trp<br>305 310 315 320 | | 960 |
| agt ttt cag atg ggt tct gcc tac cag ttc cac agc tgg agg gtc ttc<br>Ser Phe Gln Met Gly Ser Ala Tyr Gln Phe His Ser Trp Arg Val Phe<br>325 330 335 | | 1008 |
| gtc ctc gtc tgc gcc ttt cct tct gtg ttt gcc att ggg gct ctg acc<br>Val Leu Val Cys Ala Phe Pro Ser Val Phe Ala Ile Gly Ala Leu Thr<br>340 345 350 | | 1056 |
| acg cag cct gag agc ccc cgt ttc ttc cta gag aat gga aag cat gat<br>Thr Gln Pro Glu Ser Pro Arg Phe Phe Leu Glu Asn Gly Lys His Asp<br>355 360 365 | | 1104 |
| gag gcc tgg atg gtg ctg aag cag gtc cat gat acc aac atg cga gcc<br>Glu Ala Trp Met Val Leu Lys Gln Val His Asp Thr Asn Met Arg Ala<br>370 375 380 | | 1152 |
| aaa gga cat cct gag cga gtg ttc tca gta acc cac att aag acg att<br>Lys Gly His Pro Glu Arg Val Phe Ser Val Thr His Ile Lys Thr Ile<br>385 390 395 400 | | 1200 |
| cat cag gag gat gaa ttg att gag atc cag tcg gac aca ggg acc tgg<br>His Gln Glu Asp Glu Leu Ile Glu Ile Gln Ser Asp Thr Gly Thr Trp<br>405 410 415 | | 1248 |
| tac cag cgc tgg ggg gtc cgg gcc ttg agc cta ggg ggg cag gtt tgg<br>Tyr Gln Arg Trp Gly Val Arg Ala Leu Ser Leu Gly Gly Gln Val Trp<br>420 425 430 | | 1296 |
| ggg aat ttt ctc tcc tgt ttt ggt ccc gaa tat cgg cgc atc act ctg<br>Gly Asn Phe Leu Ser Cys Phe Gly Pro Glu Tyr Arg Arg Ile Thr Leu<br>435 440 445 | | 1344 |
| atg atg atg ggt gtg tgg ttc acc atg tca ttc agc tac tat ggc ctg<br>Met Met Met Gly Val Trp Phe Thr Met Ser Phe Ser Tyr Tyr Gly Leu<br>450 455 460 | | 1392 |
| acc gtc tgg ttt cct gac atg atc cgc cat ctc cag gca gtg gac tat<br>Thr Val Trp Phe Pro Asp Met Ile Arg His Leu Gln Ala Val Asp Tyr<br>465 470 475 480 | | 1440 |
| gca tcc cgc acc aaa gtg ttc ccc ggg gag cgc gta ggg cat gta act<br>Ala Ser Arg Thr Lys Val Phe Pro Gly Glu Arg Val Gly His Val Thr<br>485 490 495 | | 1488 |
| ttt aac ttc acg ttg gag aat cag atc cac cga ggc ggg cag tac ttc<br>Phe Asn Phe Thr Leu Glu Asn Gln Ile His Arg Gly Gly Gln Tyr Phe<br>500 505 510 | | 1536 |
| aat gac aag ttc att ggg ctg cgg ctc aag tca gtg tcc ttt gag gat<br>Asn Asp Lys Phe Ile Gly Leu Arg Leu Lys Ser Val Ser Phe Glu Asp<br>515 520 525 | | 1584 |
| tcc ctg ttt gaa gag tgt tat ttt gag gat gtc aca tcc agc aac acg<br>Ser Leu Phe Glu Glu Cys Tyr Phe Glu Asp Val Thr Ser Ser Asn Thr<br>530 535 540 | | 1632 |
| ttt ttc cgc aac tgc aca ttc atc aac act gtg ttc tat aac act gac<br>Phe Phe Arg Asn Cys Thr Phe Ile Asn Thr Val Phe Tyr Asn Thr Asp<br>545 550 555 560 | | 1680 |
| ctg ttc gag tac aag ttt gtg aac agc cgt ctg ata aac agt aca ttc<br>Leu Phe Glu Tyr Lys Phe Val Asn Ser Arg Leu Ile Asn Ser Thr Phe<br>565 570 575 | | 1728 |
| ctg cac aac aag gag ggc tgc ccg cta gac gtg aca ggg acg ggc gaa<br>Leu His Asn Lys Glu Gly Cys Pro Leu Asp Val Thr Gly Thr Gly Glu<br>580 585 590 | | 1776 |

```
ggt gcc tac atg gta tac ttt gtg agc ttc ctg ggg aca ctg gca gtg    1824
Gly Ala Tyr Met Val Tyr Phe Val Ser Phe Leu Gly Thr Leu Ala Val
        595                 600                 605 ctt cct ggg aat atc gtg tct gcc ctg ctc atg gac aag atc ggc agg    1872
Leu Pro Gly Asn Ile Val Ser Ala Leu Leu Met Asp Lys Ile Gly Arg
610                 615                 620 ctc aga atg ctt gct ggc tcc agc gtg atg tcc tgt gtc tcc tgc ttc    1920
Leu Arg Met Leu Ala Gly Ser Ser Val Met Ser Cys Val Ser Cys Phe
625                 630                 635                 640 ttc ctg tct ttt ggg aac agt gag tcg gcc atg atc gct ctg ctc tgc    1968
Phe Leu Ser Phe Gly Asn Ser Glu Ser Ala Met Ile Ala Leu Leu Cys
                645                 650                 655 ctt ttt ggc ggg gtc agc att gca tcc tgg aat gcg ctg gac gtg ttg    2016
Leu Phe Gly Gly Val Ser Ile Ala Ser Trp Asn Ala Leu Asp Val Leu
            660                 665                 670 act gtt gaa ctc tac ccc tca gac aag agg acc aca gct ttt ggc ttc    2064
Thr Val Glu Leu Tyr Pro Ser Asp Lys Arg Thr Thr Ala Phe Gly Phe
        675                 680                 685 ctg aat gcc ctg tgt aag ctg gca gct gtg ctg ggg atc agc atc ttc    2112
Leu Asn Ala Leu Cys Lys Leu Ala Ala Val Leu Gly Ile Ser Ile Phe
690                 695                 700 aca tcc ttc gtg gga atc acc aag gct gca ccc atc ctc ttt gcc tca    2160
Thr Ser Phe Val Gly Ile Thr Lys Ala Ala Pro Ile Leu Phe Ala Ser
705                 710                 715                 720 gct gcc ctt gcc ctt ggc agc tct ctg gcc ctg aag ctg cct gag acc    2208
Ala Ala Leu Ala Leu Gly Ser Ser Leu Ala Leu Lys Leu Pro Glu Thr
                725                 730                 735 cgg ggg cag gtg ctg cag tga                                        2229
Arg Gly Gln Val Leu Gln
            740
```

<210> SEQ ID NO 14
<211> LENGTH: 742
<212> TYPE: PRT
<213> ORGANISM: Homo sapiens

<400> SEQUENCE: 14

```
Met Glu Glu Gly Phe Arg Asp Arg Ala Ala Phe Ile Arg Gly Ala Lys
1               5                   10                  15

Asp Ile Ala Lys Glu Val Lys Lys His Ala Ala Lys Lys Val Val Lys
            20                  25                  30

Gly Leu Asp Arg Val Gln Asp Glu Tyr Ser Arg Arg Ser Tyr Ser Arg
        35                  40                  45

Phe Glu Glu Glu Asp Asp Asp Asp Phe Pro Ala Pro Ser Asp Gly
    50                  55                  60

Tyr Tyr Arg Gly Glu Gly Thr Gln Asp Glu Glu Gly Gly Ala Ser
65                  70                  75                  80

Ser Asp Ala Thr Glu Gly His Asp Glu Asp Asp Glu Ile Tyr Glu Gly
                85                  90                  95

Glu Tyr Gln Asp Ile Pro Arg Ala Glu Ser Gly Gly Lys Gly Glu Arg
            100                 105                 110

Met Ala Asp Gly Ala Pro Leu Ala Gly Val Arg Gly Gly Leu Ser Asp
        115                 120                 125

Gly Glu Gly Pro Pro Gly Arg Gly Glu Ala Gln Arg Arg Lys Glu
    130                 135                 140

Arg Glu Glu Leu Ala Gln Gln Tyr Glu Ala Ile Leu Arg Glu Cys Gly
145                 150                 155                 160

His Gly Arg Phe Gln Trp Thr Leu Tyr Phe Val Leu Gly Leu Ala Leu
```

```
                    165                 170                 175
Met Ala Asp Gly Val Glu Val Phe Val Gly Phe Val Leu Pro Ser
                180                 185                 190

Ala Glu Lys Asp Met Cys Leu Ser Asp Ser Asn Lys Gly Met Leu Gly
            195                 200                 205

Leu Ile Val Tyr Leu Gly Met Met Val Gly Ala Phe Leu Trp Gly Gly
            210                 215                 220

Leu Ala Asp Arg Leu Gly Arg Arg Gln Cys Leu Leu Ile Ser Leu Ser
225                 230                 235                 240

Val Asn Ser Val Phe Ala Phe Phe Ser Ser Phe Val Gln Gly Tyr Gly
                245                 250                 255

Thr Phe Leu Phe Cys Arg Leu Leu Ser Gly Val Gly Ile Gly Gly Ser
                260                 265                 270

Ile Pro Ile Val Phe Ser Tyr Phe Ser Glu Phe Leu Ala Gln Glu Lys
                275                 280                 285

Arg Gly Glu His Leu Ser Trp Leu Cys Met Phe Trp Met Ile Gly Gly
                290                 295                 300

Val Tyr Ala Ala Ala Met Ala Trp Ala Ile Ile Pro His Tyr Gly Trp
305                 310                 315                 320

Ser Phe Gln Met Gly Ser Ala Tyr Gln Phe His Ser Trp Arg Val Phe
                325                 330                 335

Val Leu Val Cys Ala Phe Pro Ser Val Phe Ala Ile Gly Ala Leu Thr
                340                 345                 350

Thr Gln Pro Glu Ser Pro Arg Phe Phe Leu Glu Asn Gly Lys His Asp
                355                 360                 365

Glu Ala Trp Met Val Leu Lys Gln Val His Asp Thr Asn Met Arg Ala
                370                 375                 380

Lys Gly His Pro Glu Arg Val Phe Ser Val Thr His Ile Lys Thr Ile
385                 390                 395                 400

His Gln Glu Asp Glu Leu Ile Glu Ile Gln Ser Asp Thr Gly Thr Trp
                405                 410                 415

Tyr Gln Arg Trp Gly Val Arg Ala Leu Ser Leu Gly Gly Gln Val Trp
                420                 425                 430

Gly Asn Phe Leu Ser Cys Phe Gly Pro Glu Tyr Arg Arg Ile Thr Leu
                435                 440                 445

Met Met Met Gly Val Trp Phe Thr Met Ser Phe Ser Tyr Tyr Gly Leu
                450                 455                 460

Thr Val Trp Phe Pro Asp Met Ile Arg His Leu Gln Ala Val Asp Tyr
465                 470                 475                 480

Ala Ser Arg Thr Lys Val Phe Pro Gly Glu Arg Val Gly His Val Thr
                485                 490                 495

Phe Asn Phe Thr Leu Glu Asn Gln Ile His Arg Gly Gly Gln Tyr Phe
                500                 505                 510

Asn Asp Lys Phe Ile Gly Leu Arg Leu Lys Ser Val Ser Phe Glu Asp
                515                 520                 525

Ser Leu Phe Glu Glu Cys Tyr Phe Glu Asp Val Thr Ser Ser Asn Thr
530                 535                 540

Phe Phe Arg Asn Cys Thr Phe Ile Asn Thr Val Phe Tyr Asn Thr Asp
545                 550                 555                 560

Leu Phe Glu Tyr Lys Phe Val Asn Ser Arg Leu Ile Asn Ser Thr Phe
                565                 570                 575

Leu His Asn Lys Glu Gly Cys Pro Leu Asp Val Thr Gly Thr Gly Glu
                580                 585                 590
```

```
Gly Ala Tyr Met Val Tyr Phe Val Ser Phe Leu Gly Thr Leu Ala Val
            595                 600                 605

Leu Pro Gly Asn Ile Val Ser Ala Leu Leu Met Asp Lys Ile Gly Arg
        610                 615                 620

Leu Arg Met Leu Ala Gly Ser Ser Val Met Ser Cys Val Ser Cys Phe
625                 630                 635                 640

Phe Leu Ser Phe Gly Asn Ser Glu Ser Ala Met Ile Ala Leu Leu Cys
                645                 650                 655

Leu Phe Gly Gly Val Ser Ile Ala Ser Trp Asn Ala Leu Asp Val Leu
            660                 665                 670

Thr Val Glu Leu Tyr Pro Ser Asp Lys Arg Thr Thr Ala Phe Gly Phe
        675                 680                 685

Leu Asn Ala Leu Cys Lys Leu Ala Ala Val Leu Gly Ile Ser Ile Phe
690                 695                 700

Thr Ser Phe Val Gly Ile Thr Lys Ala Ala Pro Ile Leu Phe Ala Ser
705                 710                 715                 720

Ala Ala Leu Ala Leu Gly Ser Ser Leu Ala Leu Lys Leu Pro Glu Thr
                725                 730                 735

Arg Gly Gln Val Leu Gln
            740

<210> SEQ ID NO 15
<211> LENGTH: 2052
<212> TYPE: DNA
<213> ORGANISM: Homo sapiens
<220> FEATURE:
<221> NAME/KEY: CDS
<222> LOCATION: (1)..(2052)

<400> SEQUENCE: 15 atg gat gac tac aag tat cag gac aat tat ggg ggc tat gct ccc agt        48
Met Asp Asp Tyr Lys Tyr Gln Asp Asn Tyr Gly Gly Tyr Ala Pro Ser
1               5                   10                  15 gat ggc tat tac cgc ggc aat gag tcc aac cca gaa gaa gat gca cag        96
Asp Gly Tyr Tyr Arg Gly Asn Glu Ser Asn Pro Glu Glu Asp Ala Gln
            20                  25                  30 agt gat gtc acc gaa ggc cat gat gag gaa gac gag atc tat gag ggc       144
Ser Asp Val Thr Glu Gly His Asp Glu Glu Asp Glu Ile Tyr Glu Gly
        35                  40                  45 gag tac cag ggt atc cct cac cca gat gat gtc aag gcc aag cag gcc       192
Glu Tyr Gln Gly Ile Pro His Pro Asp Asp Val Lys Ala Lys Gln Ala
50                  55                  60 aag atg gcg ccc tcc aga atg gac agc ctt cgg ggc cag aca gac ctg       240
Lys Met Ala Pro Ser Arg Met Asp Ser Leu Arg Gly Gln Thr Asp Leu
65                  70                  75                  80 atg gct gag agg ctg gaa gat gag gag cag ttg gcc cat cag tac gag       288
Met Ala Glu Arg Leu Glu Asp Glu Glu Gln Leu Ala His Gln Tyr Glu
                85                  90                  95 acc atc atg gat gag tgt ggc cat ggc cgc ttc cag tgg atc ctc ttt       336
Thr Ile Met Asp Glu Cys Gly His Gly Arg Phe Gln Trp Ile Leu Phe
            100                 105                 110 ttc gtc ttg ggt ttg gcc ctg atg gcc gat ggg gtg gaa gtg ttc gtg       384
Phe Val Leu Gly Leu Ala Leu Met Ala Asp Gly Val Glu Val Phe Val
        115                 120                 125 gtg agt ttt gcc ctg ccc agt gca gag aag gac atg tgt ctg tcc agt       432
Val Ser Phe Ala Leu Pro Ser Ala Glu Lys Asp Met Cys Leu Ser Ser
130                 135                 140 tcc aaa aaa gga atg cta ggg atg ata gtc tac ttg gga atg atg gcg       480
Ser Lys Lys Gly Met Leu Gly Met Ile Val Tyr Leu Gly Met Met Ala
145                 150                 155                 160
```

-continued

| | |
|---|---|
| ggc gcc ttc atc ctg gga ggc ctg gct gat aag ctg gga agg aag cga<br>Gly Ala Phe Ile Leu Gly Gly Leu Ala Asp Lys Leu Gly Arg Lys Arg<br>165                       170                    175 | 528 |
| gtc ctc agc atg tct ctg gcc gtc aat gcc tcc ttc gcc tcc ctc tct<br>Val Leu Ser Met Ser Leu Ala Val Asn Ala Ser Phe Ala Ser Leu Ser<br>           180                     185                   190 | 576 |
| tcc ttc gtg cag gga tat gga gcc ttc ctc ttc tgc cga ctc atc tca<br>Ser Phe Val Gln Gly Tyr Gly Ala Phe Leu Phe Cys Arg Leu Ile Ser<br>        195                     200                   205 | 624 |
| ggc atc ggt att ggg ggt gct cta ccg att gtt ttt gcc tat ttt tct<br>Gly Ile Gly Ile Gly Gly Ala Leu Pro Ile Val Phe Ala Tyr Phe Ser<br>210                       215                    220 | 672 |
| gaa ttc ttg tct cgg gag aag cga gga gaa cac ctc agt tgg ctg ggc<br>Glu Phe Leu Ser Arg Glu Lys Arg Gly Glu His Leu Ser Trp Leu Gly<br>225                       230                    235                   240 | 720 |
| atc ttc tgg atg act ggg ggc ctg tac gca tct gcc atg gcc tgg agc<br>Ile Phe Trp Met Thr Gly Gly Leu Tyr Ala Ser Ala Met Ala Trp Ser<br>                 245                   250                   255 | 768 |
| atc atc cca cac tat ggc tgg ggc ttc agc atg ggg acc aat tac cac<br>Ile Ile Pro His Tyr Gly Trp Gly Phe Ser Met Gly Thr Asn Tyr His<br>           260                     265                   270 | 816 |
| ttc cat agc tgg aga gtg ttt gtc atc gtc tgt gct ctg ccc tgc acc<br>Phe His Ser Trp Arg Val Phe Val Ile Val Cys Ala Leu Pro Cys Thr<br>275                       280                    285 | 864 |
| gtg tcc atg gtg gcc ctg aag ttc atg cca gag agc cca agg ttt ctg<br>Val Ser Met Val Ala Leu Lys Phe Met Pro Glu Ser Pro Arg Phe Leu<br>        290                     295                   300 | 912 |
| cta gag atg ggc aaa cat gat gaa gcc tgg atg att ctc aag caa gtc<br>Leu Glu Met Gly Lys His Asp Glu Ala Trp Met Ile Leu Lys Gln Val<br>305                       310                    315                   320 | 960 |
| cat gac acc aac atg aga gct aag ggg acc cca gag aaa gtg ttc acg<br>His Asp Thr Asn Met Arg Ala Lys Gly Thr Pro Glu Lys Val Phe Thr<br>                 325                   330                   335 | 1008 |
| gtt tcc aac atc aaa act ccc aag caa atg gat gaa ttc att gag atc<br>Val Ser Asn Ile Lys Thr Pro Lys Gln Met Asp Glu Phe Ile Glu Ile<br>           340                     345                   350 | 1056 |
| caa agt tca aca gga acc tgg tac cag cgc tgg ctg gtc aga ttc aag<br>Gln Ser Ser Thr Gly Thr Trp Tyr Gln Arg Trp Leu Val Arg Phe Lys<br>355                       360                    365 | 1104 |
| acc att ttc aag cag gtc tgg gat aat gcc ctg tac tgt gtg atg ggg<br>Thr Ile Phe Lys Gln Val Trp Asp Asn Ala Leu Tyr Cys Val Met Gly<br>        370                     375                   380 | 1152 |
| ccc tac aga atg aat aca ctg att ctg gcc gtg gtt tgg ttt gcc atg<br>Pro Tyr Arg Met Asn Thr Leu Ile Leu Ala Val Val Trp Phe Ala Met<br>385                       390                    395                   400 | 1200 |
| gca ttc agt tac tat gga ctg aca gtt tgg ttt cct gat atg atc cgc<br>Ala Phe Ser Tyr Tyr Gly Leu Thr Val Trp Phe Pro Asp Met Ile Arg<br>                 405                   410                   415 | 1248 |
| tat ttt caa gat gaa gaa tac aag tct aaa atg aag gtg ttt ttt ggt<br>Tyr Phe Gln Asp Glu Glu Tyr Lys Ser Lys Met Lys Val Phe Phe Gly<br>           420                     425                   430 | 1296 |
| gag cat gtg tac ggc gcc aca atc aac ttc acg atg gaa aat cag atc<br>Glu His Val Tyr Gly Ala Thr Ile Asn Phe Thr Met Glu Asn Gln Ile<br>435                       440                    445 | 1344 |
| cac caa cat ggg aaa ctt gtg aat gat aag ttc aca aga atg tac ttt<br>His Gln His Gly Lys Leu Val Asn Asp Lys Phe Thr Arg Met Tyr Phe<br>        450                     455                   460 | 1392 |
| aaa cat gta ctc ttt gag gac aca ttc ttt gac gag tgc tat ttt gaa<br>Lys His Val Leu Phe Glu Asp Thr Phe Phe Asp Glu Cys Tyr Phe Glu<br>465                       470                    475                   480 | 1440 |

```
gac gta aca tca aca gat acc tac ttc aaa aat tgt acc att gaa tca      1488
Asp Val Thr Ser Thr Asp Thr Tyr Phe Lys Asn Cys Thr Ile Glu Ser
            485                 490                 495 acc atc ttt tac aac aca gac ctc tac gag cac aag ttc atc aac tgt      1536
Thr Ile Phe Tyr Asn Thr Asp Leu Tyr Glu His Lys Phe Ile Asn Cys
        500                 505                 510 cgg ttt atc aac tcc acc ttc ctg gag cag aag gag ggc tgc cac atg      1584
Arg Phe Ile Asn Ser Thr Phe Leu Glu Gln Lys Glu Gly Cys His Met
    515                 520                 525 gac ttg gag caa gat aat gac ttc ctg att tac ctc gtc agc ttc ctg      1632
Asp Leu Glu Gln Asp Asn Asp Phe Leu Ile Tyr Leu Val Ser Phe Leu
530                 535                 540 ggc agc ctg tct gtc tta ccc ggg aac atc att tct gcc ctg ctc atg      1680
Gly Ser Leu Ser Val Leu Pro Gly Asn Ile Ile Ser Ala Leu Leu Met
545                 550                 555                 560 gat aga att gga agg ctc aag atg att ggt ggc tcc atg cta atc tct      1728
Asp Arg Ile Gly Arg Leu Lys Met Ile Gly Gly Ser Met Leu Ile Ser
                565                 570                 575 gca gtc tgc tgc ttc ttc ctg ttt ttt ggc aac agt gag tct gca atg      1776
Ala Val Cys Cys Phe Phe Leu Phe Phe Gly Asn Ser Glu Ser Ala Met
            580                 585                 590 atc ggc tgg cag tgc ctg ttc tgt ggg aca agc att gca gcc tgg aat      1824
Ile Gly Trp Gln Cys Leu Phe Cys Gly Thr Ser Ile Ala Ala Trp Asn
        595                 600                 605 gct ctg gat gtg atc aca gtg gag ctg tat ccc acc aac cag aga gca      1872
Ala Leu Asp Val Ile Thr Val Glu Leu Tyr Pro Thr Asn Gln Arg Ala
    610                 615                 620 aca gcc ttc ggc att ctc aat gga tta tgc aaa ttt ggc gcc atc ctg      1920
Thr Ala Phe Gly Ile Leu Asn Gly Leu Cys Lys Phe Gly Ala Ile Leu
625                 630                 635                 640 gga aac acc atc ttt gct tct ttt gtt ggg ata acc aaa gtg gtc ccc      1968
Gly Asn Thr Ile Phe Ala Ser Phe Val Gly Ile Thr Lys Val Val Pro
                645                 650                 655 atc ctt ctg gct gct gct tct ctg gtt ggg ggt ggc ctg att gcc ctt      2016
Ile Leu Leu Ala Ala Ala Ser Leu Val Gly Gly Gly Leu Ile Ala Leu
            660                 665                 670 cga ctg cca gag act cga gaa cag gtc ctg atg tga                      2052
Arg Leu Pro Glu Thr Arg Glu Gln Val Leu Met
        675                 680
```

<210> SEQ ID NO 16
<211> LENGTH: 683
<212> TYPE: PRT
<213> ORGANISM: Homo sapiens

<400> SEQUENCE: 16

```
Met Asp Asp Tyr Lys Tyr Gln Asp Asn Tyr Gly Gly Tyr Ala Pro Ser
1               5                   10                  15

Asp Gly Tyr Tyr Arg Gly Asn Glu Ser Asn Pro Glu Glu Asp Ala Gln
            20                  25                  30

Ser Asp Val Thr Glu Gly His Asp Glu Glu Asp Glu Ile Tyr Glu Gly
        35                  40                  45

Glu Tyr Gln Gly Ile Pro His Pro Asp Asp Val Lys Ala Lys Gln Ala
    50                  55                  60

Lys Met Ala Pro Ser Arg Met Asp Ser Leu Arg Gly Gln Thr Asp Leu
65                  70                  75                  80

Met Ala Glu Arg Leu Glu Asp Glu Glu Gln Leu Ala His Gln Tyr Glu
                85                  90                  95

Thr Ile Met Asp Glu Cys Gly His Gly Arg Phe Gln Trp Ile Leu Phe
```

-continued

```
                100             105                 110
Phe Val Leu Gly Leu Ala Leu Met Ala Asp Gly Val Glu Val Phe Val
            115                 120                 125
Val Ser Phe Ala Leu Pro Ser Ala Glu Lys Asp Met Cys Leu Ser Ser
            130                 135             140
Ser Lys Lys Gly Met Leu Gly Met Ile Val Tyr Leu Gly Met Met Ala
145                 150                 155                 160
Gly Ala Phe Ile Leu Gly Gly Leu Ala Asp Lys Leu Gly Arg Lys Arg
                165                 170                 175
Val Leu Ser Met Ser Leu Ala Val Asn Ala Ser Phe Ala Ser Leu Ser
            180                 185                 190
Ser Phe Val Gln Gly Tyr Gly Ala Phe Leu Phe Cys Arg Leu Ile Ser
            195                 200                 205
Gly Ile Gly Ile Gly Gly Ala Leu Pro Ile Val Phe Ala Tyr Phe Ser
            210                 215                 220
Glu Phe Leu Ser Arg Glu Lys Arg Gly Glu His Leu Ser Trp Leu Gly
225                 230                 235                 240
Ile Phe Trp Met Thr Gly Gly Leu Tyr Ala Ser Ala Met Ala Trp Ser
                245                 250                 255
Ile Ile Pro His Tyr Gly Trp Gly Phe Ser Met Gly Thr Asn Tyr His
                260                 265                 270
Phe His Ser Trp Arg Val Phe Val Ile Val Cys Ala Leu Pro Cys Thr
            275                 280                 285
Val Ser Met Val Ala Leu Lys Phe Met Pro Glu Ser Pro Arg Phe Leu
            290                 295                 300
Leu Glu Met Gly Lys His Asp Glu Ala Trp Met Ile Leu Lys Gln Val
305                 310                 315                 320
His Asp Thr Asn Met Arg Ala Lys Gly Thr Pro Glu Lys Val Phe Thr
                325                 330                 335
Val Ser Asn Ile Lys Thr Pro Lys Gln Met Asp Glu Phe Ile Glu Ile
                340                 345                 350
Gln Ser Ser Thr Gly Thr Trp Tyr Gln Arg Trp Leu Val Arg Phe Lys
            355                 360                 365
Thr Ile Phe Lys Gln Val Trp Asp Asn Ala Leu Tyr Cys Val Met Gly
            370                 375                 380
Pro Tyr Arg Met Asn Thr Leu Ile Leu Ala Val Val Trp Phe Ala Met
385                 390                 395                 400
Ala Phe Ser Tyr Tyr Gly Leu Thr Val Trp Phe Pro Asp Met Ile Arg
                405                 410                 415
Tyr Phe Gln Asp Glu Glu Tyr Lys Ser Lys Met Lys Val Phe Phe Gly
            420                 425                 430
Glu His Val Tyr Gly Ala Thr Ile Asn Phe Thr Met Glu Asn Gln Ile
            435                 440                 445
His Gln His Gly Lys Leu Val Asn Asp Lys Phe Thr Arg Met Tyr Phe
            450                 455                 460
Lys His Val Leu Phe Glu Asp Thr Phe Phe Asp Glu Cys Tyr Phe Glu
465                 470                 475                 480
Asp Val Thr Ser Thr Asp Thr Tyr Phe Lys Asn Cys Thr Ile Glu Ser
                485                 490                 495
Thr Ile Phe Tyr Asn Thr Asp Leu Tyr Glu His Lys Phe Ile Asn Cys
            500                 505                 510
Arg Phe Ile Asn Ser Thr Phe Leu Glu Gln Lys Glu Gly Cys His Met
            515                 520                 525
```

```
Asp Leu Glu Gln Asp Asn Asp Phe Leu Ile Tyr Leu Val Ser Phe Leu
        530                 535                 540

Gly Ser Leu Ser Val Leu Pro Gly Asn Ile Ile Ser Ala Leu Leu Met
545                 550                 555                 560

Asp Arg Ile Gly Arg Leu Lys Met Ile Gly Gly Ser Met Leu Ile Ser
                565                 570                 575

Ala Val Cys Cys Phe Leu Phe Phe Gly Asn Ser Glu Ser Ala Met
            580                 585                 590

Ile Gly Trp Gln Cys Leu Phe Cys Gly Thr Ser Ile Ala Ala Trp Asn
                595                 600                 605

Ala Leu Asp Val Ile Thr Val Glu Leu Tyr Pro Thr Asn Gln Arg Ala
            610                 615                 620

Thr Ala Phe Gly Ile Leu Asn Gly Leu Cys Lys Phe Gly Ala Ile Leu
625                 630                 635                 640

Gly Asn Thr Ile Phe Ala Ser Phe Val Gly Ile Thr Lys Val Val Pro
                645                 650                 655

Ile Leu Leu Ala Ala Ala Ser Leu Val Gly Gly Leu Ile Ala Leu
                660                 665                 670

Arg Leu Pro Glu Thr Arg Glu Gln Val Leu Met
            675                 680

<210> SEQ ID NO 17
<211> LENGTH: 2184
<212> TYPE: DNA
<213> ORGANISM: Homo sapiens
<220> FEATURE:
<221> NAME/KEY: CDS
<222> LOCATION: (1)..(2184)

<400> SEQUENCE: 17 atg gaa gac tct tac aag gat agg act tca ctg atg aag ggt gcc aag      48
Met Glu Asp Ser Tyr Lys Asp Arg Thr Ser Leu Met Lys Gly Ala Lys
1               5                   10                  15 gac att gcc aga gag gtg aag aaa caa aca gta aag aag gtg aat caa      96
Asp Ile Ala Arg Glu Val Lys Lys Gln Thr Val Lys Lys Val Asn Gln
            20                  25                  30 gct gtg gac cga gcc cag gat gaa tac acc cag agg tcc tac agt cgg     144
Ala Val Asp Arg Ala Gln Asp Glu Tyr Thr Gln Arg Ser Tyr Ser Arg
        35                  40                  45 ttc caa gat gaa gaa gat gat gat gac tac tac ccg gct gga gaa acc     192
Phe Gln Asp Glu Glu Asp Asp Asp Asp Tyr Tyr Pro Ala Gly Glu Thr
    50                  55                  60 tat aat ggt gag gcc aac gat gac gaa ggc tca agt gaa gcc act gag     240
Tyr Asn Gly Glu Ala Asn Asp Asp Glu Gly Ser Ser Glu Ala Thr Glu
65                  70                  75                  80 ggg cat gat gaa gat gat gag atc tat gag ggg gag tat cag ggc atc     288
Gly His Asp Glu Asp Asp Glu Ile Tyr Glu Gly Glu Tyr Gln Gly Ile
                85                  90                  95 ccc agt atg aac caa gcg aag gac agc atc gtg tca gtg ggg cag ccc     336
Pro Ser Met Asn Gln Ala Lys Asp Ser Ile Val Ser Val Gly Gln Pro
            100                 105                 110 aag ggc gat gag tac aag gac cga cgg gag ctg gaa tca gaa agg aga     384
Lys Gly Asp Glu Tyr Lys Asp Arg Arg Glu Leu Glu Ser Glu Arg Arg
        115                 120                 125 gct gac gag gaa gag tta gcc cag cag tat gag ctg ata atc caa gaa     432
Ala Asp Glu Glu Glu Leu Ala Gln Gln Tyr Glu Leu Ile Ile Gln Glu
    130                 135                 140 tgc ggt cat ggt cgt ttt cag tgg gcc ctt ttc ttc gtc ctg ggc atg     480
Cys Gly His Gly Arg Phe Gln Trp Ala Leu Phe Phe Val Leu Gly Met
145                 150                 155                 160
```

-continued

| | | |
|---|---|---|
| gct ctt atg gca gac ggt gta gag gtg ttt gtc gtt ggc ttc gtg tta<br>Ala Leu Met Ala Asp Gly Val Glu Val Phe Val Val Gly Phe Val Leu<br>                                165                            170                            175 | 528 |
| ccc agt gct gag aca gac ctc tgc atc cca aat tca gga tct gga tgg<br>Pro Ser Ala Glu Thr Asp Leu Cys Ile Pro Asn Ser Gly Ser Gly Trp<br>                180                            185                            190 | 576 |
| cta ggc agc ata gtg tac ctc ggg atg atg gtg ggg gcg ttc ttc tgg<br>Leu Gly Ser Ile Val Tyr Leu Gly Met Met Val Gly Ala Phe Phe Trp<br>                    195                            200                            205 | 624 |
| gga gga ctg gca gac aaa gtg gga agg aaa cag tct ctt ctg att tgc<br>Gly Gly Leu Ala Asp Lys Val Gly Arg Lys Gln Ser Leu Leu Ile Cys<br>        210                            215                            220 | 672 |
| atg tct gtc aac gga ttc ttt gcc ttc ctt tct tca ttt gtc caa ggt<br>Met Ser Val Asn Gly Phe Phe Ala Phe Leu Ser Ser Phe Val Gln Gly<br>225                         230                            235                         240 | 720 |
| tat ggc ttc ttt ctc ttc tgt cgc tta ctt tct gga ttc ggg att gga<br>Tyr Gly Phe Phe Leu Phe Cys Arg Leu Leu Ser Gly Phe Gly Ile Gly<br>                                245                            250                            255 | 768 |
| gga gcc ata ccc act gtg ttc tcg tac ttt gct gaa gtc ctg gcc cgg<br>Gly Ala Ile Pro Thr Val Phe Ser Tyr Phe Ala Glu Val Leu Ala Arg<br>                260                            265                            270 | 816 |
| gaa aag cgg ggc gaa cac ttg agc tgg ctc tgc atg ttc tgg atg atc<br>Glu Lys Arg Gly Glu His Leu Ser Trp Leu Cys Met Phe Trp Met Ile<br>              275                            280                            285 | 864 |
| ggt ggc atc tac gcc tct gcc atg gcc tgg gcc atc atc ccg cac tac<br>Gly Gly Ile Tyr Ala Ser Ala Met Ala Trp Ala Ile Ile Pro His Tyr<br>        290                            295                            300 | 912 |
| ggg tgg agc ttc agc atg gga tcg gcc tac cag ttt cac agt tgg cgt<br>Gly Trp Ser Phe Ser Met Gly Ser Ala Tyr Gln Phe His Ser Trp Arg<br>305                         310                            315                         320 | 960 |
| gtg ttt gtc atc gtc tgt gca ctc ccc tgt gtc tcc tcc gtg gtg gcc<br>Val Phe Val Ile Val Cys Ala Leu Pro Cys Val Ser Ser Val Val Ala<br>                                325                            330                            335 | 1008 |
| ctc aca ttc atg cct gaa agc cca cga ttc ttg ttg gag gtt gga aaa<br>Leu Thr Phe Met Pro Glu Ser Pro Arg Phe Leu Leu Glu Val Gly Lys<br>                340                            345                            350 | 1056 |
| cat gat gaa gct tgg atg att ctg aag tta att cat gac acc aac atg<br>His Asp Glu Ala Trp Met Ile Leu Lys Leu Ile His Asp Thr Asn Met<br>              355                            360                            365 | 1104 |
| aga gcc cgg ggt cag cct gag aag gtc ttc acg gta aac aaa ata aaa<br>Arg Ala Arg Gly Gln Pro Glu Lys Val Phe Thr Val Asn Lys Ile Lys<br>        370                            375                            380 | 1152 |
| act cct aaa caa ata gat gag ctg att gaa att gag agt gac aca gga<br>Thr Pro Lys Gln Ile Asp Glu Leu Ile Glu Ile Glu Ser Asp Thr Gly<br>385                         390                            395                         400 | 1200 |
| aca tgg tat agg agg tgt ttt gtt cgg atc cgc acc gag ctg tac gga<br>Thr Trp Tyr Arg Arg Cys Phe Val Arg Ile Arg Thr Glu Leu Tyr Gly<br>                    405                            410                            415 | 1248 |
| att tgg ttg act ttt atg aga tgt ttc aac tac cca gtc agg gat aat<br>Ile Trp Leu Thr Phe Met Arg Cys Phe Asn Tyr Pro Val Arg Asp Asn<br>                420                            425                            430 | 1296 |
| aca ata aag ctt aca att gtt tgg ttc acc ctg tcc ttt ggg tac tat<br>Thr Ile Lys Leu Thr Ile Val Trp Phe Thr Leu Ser Phe Gly Tyr Tyr<br>                    435                            440                            445 | 1344 |
| gga tta tcc gtt tgg ttc cct gat gtc att aaa cct ctg cag tcc gat<br>Gly Leu Ser Val Trp Phe Pro Asp Val Ile Lys Pro Leu Gln Ser Asp<br>        450                            455                            460 | 1392 |
| gaa tat gca ttg cta acc aga aat gtg gag aga gat aaa tat gca aat<br>Glu Tyr Ala Leu Leu Thr Arg Asn Val Glu Arg Asp Lys Tyr Ala Asn<br>465                         470                            475                         480 | 1440 |

```
ttc act att aac ttt aca atg gaa aat cag att cat act gga atg gaa   1488
Phe Thr Ile Asn Phe Thr Met Glu Asn Gln Ile His Thr Gly Met Glu
                485                 490                 495 tac gac aat ggc aga ttc ata ggg gtc aag ttc aaa tct gta act ttc   1536
Tyr Asp Asn Gly Arg Phe Ile Gly Val Lys Phe Lys Ser Val Thr Phe
            500                 505                 510 aaa gac tct gtt ttt aag tcc tgc acc ttt gag gat gta act tca gtg   1584
Lys Asp Ser Val Phe Lys Ser Cys Thr Phe Glu Asp Val Thr Ser Val
        515                 520                 525 aac acc tac ttc aag aac tgc aca ttt att gac act gtt ttt gac aac   1632
Asn Thr Tyr Phe Lys Asn Cys Thr Phe Ile Asp Thr Val Phe Asp Asn
    530                 535                 540 aca gat ttt gag cca tat aaa ttc att gac agt gaa ttt aaa aac tgc   1680
Thr Asp Phe Glu Pro Tyr Lys Phe Ile Asp Ser Glu Phe Lys Asn Cys
545                 550                 555                 560 tcg ttt ttt cac aac aag acg gga tgt cag att acc ttt gat gat gac   1728
Ser Phe Phe His Asn Lys Thr Gly Cys Gln Ile Thr Phe Asp Asp Asp
                565                 570                 575 tat agt gcc tac tgg att tat ttt gtc aac ttt ctg ggg aca ttg gca   1776
Tyr Ser Ala Tyr Trp Ile Tyr Phe Val Asn Phe Leu Gly Thr Leu Ala
            580                 585                 590 gta ttg cca ggg aac att gtg tct gct ctg ctg atg gac aga att ggg   1824
Val Leu Pro Gly Asn Ile Val Ser Ala Leu Leu Met Asp Arg Ile Gly
        595                 600                 605 cgc tta aca atg cta ggt ggc tct atg gtg ctt tcg ggg atc agc tgt   1872
Arg Leu Thr Met Leu Gly Gly Ser Met Val Leu Ser Gly Ile Ser Cys
    610                 615                 620 ttc ttc ctt tgg ttc ggc acc agt gaa tcc atg atg ata ggc atg ctg   1920
Phe Phe Leu Trp Phe Gly Thr Ser Glu Ser Met Met Ile Gly Met Leu
625                 630                 635                 640 tgt ctg tac aat gga ttg acc atc tca gcc tgg aac tct ctt gac gtg   1968
Cys Leu Tyr Asn Gly Leu Thr Ile Ser Ala Trp Asn Ser Leu Asp Val
                645                 650                 655 gtc act gtg gaa ctg tac ccc aca gac cgg agg gca aca ggc ttt ggc   2016
Val Thr Val Glu Leu Tyr Pro Thr Asp Arg Arg Ala Thr Gly Phe Gly
            660                 665                 670 ttc tta aat gcg cta tgc aag gca gca gcc gtc ctg gga aac tta ata   2064
Phe Leu Asn Ala Leu Cys Lys Ala Ala Ala Val Leu Gly Asn Leu Ile
        675                 680                 685 ttt ggc tct ctg gtc agc atc acc aaa tca atc ccc atc ctg ctg gct   2112
Phe Gly Ser Leu Val Ser Ile Thr Lys Ser Ile Pro Ile Leu Leu Ala
    690                 695                 700 tct act gtg ctc gtg tgt gga gga ctc gtt ggg ctg tgc ctg cct gac   2160
Ser Thr Val Leu Val Cys Gly Gly Leu Val Gly Leu Cys Leu Pro Asp
705                 710                 715                 720 aca cga acc cag gtt ctg atg taa                                   2184
Thr Arg Thr Gln Val Leu Met
                725
```

<210> SEQ ID NO 18
<211> LENGTH: 727
<212> TYPE: PRT
<213> ORGANISM: Homo sapiens

<400> SEQUENCE: 18

Met Glu Asp Ser Tyr Lys Asp Arg Thr Ser Leu Met Lys Gly Ala Lys
1               5                   10                  15

Asp Ile Ala Arg Glu Val Lys Lys Gln Thr Val Lys Lys Val Asn Gln
            20                  25                  30

Ala Val Asp Arg Ala Gln Asp Glu Tyr Thr Gln Arg Ser Tyr Ser Arg

```
                35                  40                  45
Phe Gln Asp Glu Glu Asp Asp Asp Tyr Tyr Pro Ala Gly Glu Thr
 50                  55                  60

Tyr Asn Gly Glu Ala Asn Asp Asp Glu Gly Ser Ser Glu Ala Thr Glu
 65                  70                  75                  80

Gly His Asp Glu Asp Glu Ile Tyr Glu Gly Tyr Gln Gly Ile
                 85                  90                  95

Pro Ser Met Asn Gln Ala Lys Asp Ser Ile Val Ser Val Gly Gln Pro
                100                 105                 110

Lys Gly Asp Glu Tyr Lys Asp Arg Arg Glu Leu Glu Ser Glu Arg Arg
                115                 120                 125

Ala Asp Glu Glu Glu Leu Ala Gln Gln Tyr Glu Leu Ile Ile Gln Glu
                130                 135                 140

Cys Gly His Gly Arg Phe Gln Trp Ala Leu Phe Phe Val Leu Gly Met
145                 150                 155                 160

Ala Leu Met Ala Asp Gly Val Glu Val Phe Val Val Gly Phe Val Leu
                165                 170                 175

Pro Ser Ala Glu Thr Asp Leu Cys Ile Pro Asn Ser Gly Ser Gly Trp
                180                 185                 190

Leu Gly Ser Ile Val Tyr Leu Gly Met Met Val Gly Ala Phe Phe Trp
                195                 200                 205

Gly Gly Leu Ala Asp Lys Val Gly Arg Lys Gln Ser Leu Leu Ile Cys
210                 215                 220

Met Ser Val Asn Gly Phe Phe Ala Phe Leu Ser Ser Phe Val Gln Gly
225                 230                 235                 240

Tyr Gly Phe Phe Leu Phe Cys Arg Leu Leu Ser Gly Phe Gly Ile Gly
                245                 250                 255

Gly Ala Ile Pro Thr Val Phe Ser Tyr Phe Ala Glu Val Leu Ala Arg
                260                 265                 270

Glu Lys Arg Gly Glu His Leu Ser Trp Leu Cys Met Phe Trp Met Ile
                275                 280                 285

Gly Gly Ile Tyr Ala Ser Ala Met Ala Trp Ala Ile Ile Pro His Tyr
                290                 295                 300

Gly Trp Ser Phe Ser Met Gly Ser Ala Tyr Gln Phe His Ser Trp Arg
305                 310                 315                 320

Val Phe Val Ile Val Cys Ala Leu Pro Cys Val Ser Ser Val Val Ala
                325                 330                 335

Leu Thr Phe Met Pro Glu Ser Pro Arg Phe Leu Leu Glu Val Gly Lys
                340                 345                 350

His Asp Glu Ala Trp Met Ile Leu Lys Leu Ile His Asp Thr Asn Met
                355                 360                 365

Arg Ala Arg Gly Gln Pro Glu Lys Val Phe Thr Val Asn Lys Ile Lys
                370                 375                 380

Thr Pro Lys Gln Ile Asp Glu Leu Ile Glu Ile Glu Ser Asp Thr Gly
385                 390                 395                 400

Thr Trp Tyr Arg Arg Cys Phe Val Arg Ile Arg Thr Glu Leu Tyr Gly
                405                 410                 415

Ile Trp Leu Thr Phe Met Arg Cys Phe Asn Tyr Pro Val Arg Asp Asn
                420                 425                 430

Thr Ile Lys Leu Thr Ile Val Trp Phe Thr Leu Ser Phe Gly Tyr Tyr
                435                 440                 445

Gly Leu Ser Val Trp Phe Pro Asp Val Ile Lys Pro Leu Gln Ser Asp
450                 455                 460
```

```
Glu Tyr Ala Leu Leu Thr Arg Asn Val Glu Arg Asp Lys Tyr Ala Asn
465                 470                 475                 480

Phe Thr Ile Asn Phe Thr Met Glu Asn Gln Ile His Thr Gly Met Glu
            485                 490                 495

Tyr Asp Asn Gly Arg Phe Ile Gly Val Lys Phe Lys Ser Val Thr Phe
                500                 505                 510

Lys Asp Ser Val Phe Lys Ser Cys Thr Phe Glu Asp Val Thr Ser Val
        515                 520                 525

Asn Thr Tyr Phe Lys Asn Cys Thr Phe Ile Asp Thr Val Phe Asp Asn
    530                 535                 540

Thr Asp Phe Glu Pro Tyr Lys Phe Ile Asp Ser Glu Phe Lys Asn Cys
545                 550                 555                 560

Ser Phe Phe His Asn Lys Thr Gly Cys Gln Ile Thr Phe Asp Asp
                565                 570                 575

Tyr Ser Ala Tyr Trp Ile Tyr Phe Val Asn Phe Leu Gly Thr Leu Ala
                580                 585                 590

Val Leu Pro Gly Asn Ile Val Ser Ala Leu Leu Met Asp Arg Ile Gly
                595                 600                 605

Arg Leu Thr Met Leu Gly Gly Ser Met Val Leu Ser Gly Ile Ser Cys
610                 615                 620

Phe Phe Leu Trp Phe Gly Thr Ser Glu Ser Met Met Ile Gly Met Leu
625                 630                 635                 640

Cys Leu Tyr Asn Gly Leu Thr Ile Ser Ala Trp Asn Ser Leu Asp Val
                645                 650                 655

Val Thr Val Glu Leu Tyr Pro Thr Asp Arg Arg Ala Thr Gly Phe Gly
                660                 665                 670

Phe Leu Asn Ala Leu Cys Lys Ala Ala Ala Val Leu Gly Asn Leu Ile
                675                 680                 685

Phe Gly Ser Leu Val Ser Ile Thr Lys Ser Ile Pro Ile Leu Leu Ala
                690                 695                 700

Ser Thr Val Leu Val Cys Gly Gly Leu Val Gly Leu Cys Leu Pro Asp
705                 710                 715                 720

Thr Arg Thr Gln Val Leu Met
                725

<210> SEQ ID NO 19
<211> LENGTH: 2229
<212> TYPE: DNA
<213> ORGANISM: Bos taurus
<220> FEATURE:
<221> NAME/KEY: CDS
<222> LOCATION: (1)..(2229)

<400> SEQUENCE: 19 atg gaa gag ggc ttc aga gac cgg gca gct ttc atc cgt ggg gcc aaa     48
Met Glu Glu Gly Phe Arg Asp Arg Ala Ala Phe Ile Arg Gly Ala Lys
1               5                   10                  15 gac att gcc aag gaa gtc aag aag cat gca acc aag aag gtg gtg aag     96
Asp Ile Ala Lys Glu Val Lys Lys His Ala Thr Lys Lys Val Val Lys
            20                  25                  30 ggc ctg gac aga gtc cag gat gaa tat tcc cgg aga tcc tac tcc cgc    144
Gly Leu Asp Arg Val Gln Asp Glu Tyr Ser Arg Arg Ser Tyr Ser Arg
        35                  40                  45 ttt gag gag gag gac gat gat gac ttc ccc gcc cct gct gat ggc        192
Phe Glu Glu Glu Asp Asp Asp Asp Phe Pro Ala Pro Ala Asp Gly
    50                  55                  60 tat tac cgc ggg gaa ggg gcc cag gat gag gag gaa ggc ggc gca tct    240
Tyr Tyr Arg Gly Glu Gly Ala Gln Asp Glu Glu Glu Gly Gly Ala Ser
```

|  |  |  |  |  |  |  |  |  |  |  |  |  |  |  |  |
|---|---|---|---|---|---|---|---|---|---|---|---|---|---|---|---|
| 65 |  |  |  |  | 70 |  |  |  |  | 75 |  |  |  |  | 80 |

```
agt gat gcc acc gag ggc cac gac gag gat gat gag atc tac gag ggg      288
Ser Asp Ala Thr Glu Gly His Asp Glu Asp Asp Glu Ile Tyr Glu Gly
                85                  90                  95 gaa tat cag ggc atc ccc cgg gca gag tct ggg ggc aaa ggc gag cgg      336
Glu Tyr Gln Gly Ile Pro Arg Ala Glu Ser Gly Gly Lys Gly Glu Arg
            100                 105                 110 atg gca gat ggg gca ccc ctg gct gga gtg agg ggg ggc ttg ggt gat      384
Met Ala Asp Gly Ala Pro Leu Ala Gly Val Arg Gly Gly Leu Gly Asp
            115                 120                 125 ggg gag ggt ccc ccg ggg ggg cgg gga gaa gcg cag cgg cgg aaa gaa      432
Gly Glu Gly Pro Pro Gly Gly Arg Gly Glu Ala Gln Arg Arg Lys Glu
        130                 135                 140 cgg gaa gaa cta gcc cag cag tat gaa gcc atc cta cgg gag tgc ggc      480
Arg Glu Glu Leu Ala Gln Gln Tyr Glu Ala Ile Leu Arg Glu Cys Gly
145                 150                 155                 160 cat ggc cgc ttc cag tgg aca ctc tat ttc gtg ctt ggt ctg gca ctg      528
His Gly Arg Phe Gln Trp Thr Leu Tyr Phe Val Leu Gly Leu Ala Leu
                165                 170                 175 atg gcc gat ggt gtt gag gtc ttc gtg gtg ggc ttc gtg ctg ccc agt      576
Met Ala Asp Gly Val Glu Val Phe Val Val Gly Phe Val Leu Pro Ser
            180                 185                 190 gct gag aaa gac atg tgc ctg tct gac tcc aac aaa ggc atg ctg ggc      624
Ala Glu Lys Asp Met Cys Leu Ser Asp Ser Asn Lys Gly Met Leu Gly
            195                 200                 205 ctc att gtc tac ctg ggc atg atg gtg gga gcc ttc ctc tgg gga ggg      672
Leu Ile Val Tyr Leu Gly Met Met Val Gly Ala Phe Leu Trp Gly Gly
        210                 215                 220 ctg gct gat cgg ctg ggt cga aga cag tgt ctg ctc atc tca ctc tca      720
Leu Ala Asp Arg Leu Gly Arg Arg Gln Cys Leu Leu Ile Ser Leu Ser
225                 230                 235                 240 gtc aac agt gtc ttc gcc ttt ttc tca tct ttc gtc cag ggt tat ggc      768
Val Asn Ser Val Phe Ala Phe Phe Ser Ser Phe Val Gln Gly Tyr Gly
                245                 250                 255 act ttc ctt ttc tgc cgt ctc ctt tct ggg gtt ggg atc gga ggg tcc      816
Thr Phe Leu Phe Cys Arg Leu Leu Ser Gly Val Gly Ile Gly Gly Ser
            260                 265                 270 atc ccc atc gtc ttc tcc tat ttc tcg gag ttt ctg gca cag gag aaa      864
Ile Pro Ile Val Phe Ser Tyr Phe Ser Glu Phe Leu Ala Gln Glu Lys
            275                 280                 285 cgt ggg gag cat ttg agc tgg ctc tgc atg ttt tgg atg att ggt gga      912
Arg Gly Glu His Leu Ser Trp Leu Cys Met Phe Trp Met Ile Gly Gly
        290                 295                 300 gtg tat gca gct gct atg gcc tgg gcc atc atc ccc cac tat ggg tgg      960
Val Tyr Ala Ala Ala Met Ala Trp Ala Ile Ile Pro His Tyr Gly Trp
305                 310                 315                 320 agc ttt cag atg ggg tct gct tac cag ttc cac agc tgg agg gtc ttt     1008
Ser Phe Gln Met Gly Ser Ala Tyr Gln Phe His Ser Trp Arg Val Phe
                325                 330                 335 gtc ctc gtc tgc gct ttc cct tct gtg ttt gcc att ggg gct ctg acc     1056
Val Leu Val Cys Ala Phe Pro Ser Val Phe Ala Ile Gly Ala Leu Thr
            340                 345                 350 aca cag cct gaa agc ccc cgt ttc ttc ctg gag aat ggg aag cat gat     1104
Thr Gln Pro Glu Ser Pro Arg Phe Phe Leu Glu Asn Gly Lys His Asp
            355                 360                 365 gag gcc tgg atg gta ctg aag cag gtc cat gac acc aac atg cgg gcc     1152
Glu Ala Trp Met Val Leu Lys Gln Val His Asp Thr Asn Met Arg Ala
        370                 375                 380 aag ggg cat cct gag cga gtc ttc tcg gta acc cac att aag aca att     1200
Lys Gly His Pro Glu Arg Val Phe Ser Val Thr His Ile Lys Thr Ile
```

```
                     385                 390                 395                 400
cat cag gag gat gag ttg att gag atc cag tct gac aca ggg gcc tgg       1248
His Gln Glu Asp Glu Leu Ile Glu Ile Gln Ser Asp Thr Gly Ala Trp
                        405                 410                 415 tac cag cgc tgg ggg gtc cgg gcc ttg agc ctg gga ggg cag gtc tgg       1296
Tyr Gln Arg Trp Gly Val Arg Ala Leu Ser Leu Gly Gly Gln Val Trp
                420                 425                 430 ggg aat ttc ctc tct tgt ttt ggt cca gaa tac cgc cgc atc act ctg       1344
Gly Asn Phe Leu Ser Cys Phe Gly Pro Glu Tyr Arg Arg Ile Thr Leu
                    435                 440                 445 atg atg atg ggt gtg tgg ttc acc atg tca ttc agc tac tat ggc ctg       1392
Met Met Met Gly Val Trp Phe Thr Met Ser Phe Ser Tyr Tyr Gly Leu
                        450                 455                 460 act gtc tgg ttt ccc gac atg atc cgc cat ctc caa gcg gtg gac tat       1440
Thr Val Trp Phe Pro Asp Met Ile Arg His Leu Gln Ala Val Asp Tyr
465                 470                 475                 480 gca gcc cgc acc aaa gtg ttc cct ggg gaa cgt gtg gag cac gtg act       1488
Ala Ala Arg Thr Lys Val Phe Pro Gly Glu Arg Val Glu His Val Thr
                            485                 490                 495 ttt aac ttc acc ttg gag aat cag atc cac cga ggg gga cag tac ttc       1536
Phe Asn Phe Thr Leu Glu Asn Gln Ile His Arg Gly Gly Gln Tyr Phe
                500                 505                 510 aat gac aag ttc att ggg cta cgt ctg aag tca gta tcc ttt gag gac       1584
Asn Asp Lys Phe Ile Gly Leu Arg Leu Lys Ser Val Ser Phe Glu Asp
                    515                 520                 525 tcc ctg ttt gag gag tgt tat ttc gag gat gtc aca tcc agc aac aca       1632
Ser Leu Phe Glu Glu Cys Tyr Phe Glu Asp Val Thr Ser Ser Asn Thr
                        530                 535                 540 ttt ttc cgc aac tgc acg ttc atc aac acc gtg ttc tat aac act gac       1680
Phe Phe Arg Asn Cys Thr Phe Ile Asn Thr Val Phe Tyr Asn Thr Asp
545                 550                 555                 560 ctg ttt gag tac aag ttt gtg aac agc cgt ctg gtg aac agc aca ttc       1728
Leu Phe Glu Tyr Lys Phe Val Asn Ser Arg Leu Val Asn Ser Thr Phe
                            565                 570                 575 ctg cac aac aag gag ggc tgc ccc ctg gac gtg acg ggg acg ggt gaa       1776
Leu His Asn Lys Glu Gly Cys Pro Leu Asp Val Thr Gly Thr Gly Glu
                580                 585                 590 ggc gcc tac atg gtg tat ttt gtc agc ttc ttg ggg acg ctg gct gtg       1824
Gly Ala Tyr Met Val Tyr Phe Val Ser Phe Leu Gly Thr Leu Ala Val
                    595                 600                 605 ctt cct ggg aac att gtg tct gct ctc ctc atg gac aag att ggc agg       1872
Leu Pro Gly Asn Ile Val Ser Ala Leu Leu Met Asp Lys Ile Gly Arg
                        610                 615                 620 ctc cga atg ctt gct ggc tcc agc gtg atg tcc tgt gtc tcc tgc ttc       1920
Leu Arg Met Leu Ala Gly Ser Ser Val Met Ser Cys Val Ser Cys Phe
625                 630                 635                 640 ttc ctg tct ttc ggg aac agt gag tcc gcc atg atc gct ctc ctc tgc       1968
Phe Leu Ser Phe Gly Asn Ser Glu Ser Ala Met Ile Ala Leu Leu Cys
                            645                 650                 655 ctt ttc ggg ggg gtc agc atc gca tcc tgg aac gcg ctg gac gtg ttg       2016
Leu Phe Gly Gly Val Ser Ile Ala Ser Trp Asn Ala Leu Asp Val Leu
                660                 665                 670 act gtt gaa ctc tac ccc tcg gac aag aga acc aca gcc ttc ggc ttc       2064
Thr Val Glu Leu Tyr Pro Ser Asp Lys Arg Thr Thr Ala Phe Gly Phe
                    675                 680                 685 ctg aat gcc ctg tgt aag ctg gca gct gtg ctg ggg atc agc atc ttc       2112
Leu Asn Ala Leu Cys Lys Leu Ala Ala Val Leu Gly Ile Ser Ile Phe
                        690                 695                 700 acg tcc ttt gtg gga atc acc aag gct gcc ccc atc ctc ttt gcc tcc       2160
Thr Ser Phe Val Gly Ile Thr Lys Ala Ala Pro Ile Leu Phe Ala Ser
```

```
                    705                 710                 715                 720
gct gcc ctt gcc ctc ggg agt tct ctg gcc ctg aag ctg ccc gag acc           2208
Ala Ala Leu Ala Leu Gly Ser Ser Leu Ala Leu Lys Leu Pro Glu Thr
                725                 730                 735 cgg ggg cag gtg ctg cag tga                                                2229
Arg Gly Gln Val Leu Gln
                740

<210> SEQ ID NO 20
<211> LENGTH: 742
<212> TYPE: PRT
<213> ORGANISM: Bos taurus

<400> SEQUENCE: 20

Met Glu Glu Gly Phe Arg Asp Arg Ala Ala Phe Ile Arg Gly Ala Lys
1               5                   10                  15

Asp Ile Ala Lys Glu Val Lys Lys His Ala Thr Lys Lys Val Val Lys
            20                  25                  30

Gly Leu Asp Arg Val Gln Asp Glu Tyr Ser Arg Arg Ser Tyr Ser Arg
        35                  40                  45

Phe Glu Glu Glu Asp Asp Asp Asp Phe Pro Ala Pro Ala Asp Gly
    50                  55                  60

Tyr Tyr Arg Gly Glu Gly Ala Gln Asp Glu Glu Gly Gly Ala Ser
65                  70                  75                  80

Ser Asp Ala Thr Glu Gly His Asp Glu Asp Glu Ile Tyr Glu Gly
            85                  90                  95

Glu Tyr Gln Gly Ile Pro Arg Ala Glu Ser Gly Gly Lys Gly Glu Arg
            100                 105                 110

Met Ala Asp Gly Ala Pro Leu Ala Gly Val Arg Gly Gly Leu Gly Asp
        115                 120                 125

Gly Glu Gly Pro Pro Gly Gly Arg Gly Glu Ala Gln Arg Arg Lys Glu
    130                 135                 140

Arg Glu Glu Leu Ala Gln Gln Tyr Glu Ala Ile Leu Arg Glu Cys Gly
145                 150                 155                 160

His Gly Arg Phe Gln Trp Thr Leu Tyr Phe Val Leu Gly Leu Ala Leu
                165                 170                 175

Met Ala Asp Gly Val Glu Val Phe Val Val Gly Phe Val Leu Pro Ser
            180                 185                 190

Ala Glu Lys Asp Met Cys Leu Ser Asp Ser Asn Lys Gly Met Leu Gly
        195                 200                 205

Leu Ile Val Tyr Leu Gly Met Met Val Gly Ala Phe Leu Trp Gly Gly
    210                 215                 220

Leu Ala Asp Arg Leu Gly Arg Arg Gln Cys Leu Leu Ile Ser Leu Ser
225                 230                 235                 240

Val Asn Ser Val Phe Ala Phe Phe Ser Ser Phe Val Gln Gly Tyr Gly
                245                 250                 255

Thr Phe Leu Phe Cys Arg Leu Leu Ser Gly Val Gly Ile Gly Gly Ser
            260                 265                 270

Ile Pro Ile Val Phe Ser Tyr Phe Ser Glu Phe Leu Ala Gln Glu Lys
        275                 280                 285

Arg Gly Glu His Leu Ser Trp Leu Cys Met Phe Trp Met Ile Gly Gly
    290                 295                 300

Val Tyr Ala Ala Ala Met Ala Trp Ala Ile Ile Pro His Tyr Gly Trp
305                 310                 315                 320

Ser Phe Gln Met Gly Ser Ala Tyr Gln Phe His Ser Trp Arg Val Phe
                325                 330                 335
```

```
Val Leu Val Cys Ala Phe Pro Ser Val Phe Ala Ile Gly Ala Leu Thr
            340                 345                 350

Thr Gln Pro Glu Ser Pro Arg Phe Phe Leu Glu Asn Gly Lys His Asp
            355                 360                 365

Glu Ala Trp Met Val Leu Lys Gln Val His Asp Thr Asn Met Arg Ala
            370                 375                 380

Lys Gly His Pro Glu Arg Val Phe Ser Val Thr His Ile Lys Thr Ile
385                 390                 395                 400

His Gln Glu Asp Glu Leu Ile Glu Ile Gln Ser Asp Thr Gly Ala Trp
            405                 410                 415

Tyr Gln Arg Trp Gly Val Arg Ala Leu Ser Leu Gly Gly Gln Val Trp
            420                 425                 430

Gly Asn Phe Leu Ser Cys Phe Gly Pro Glu Tyr Arg Arg Ile Thr Leu
            435                 440                 445

Met Met Met Gly Val Trp Phe Thr Met Ser Phe Ser Tyr Tyr Gly Leu
            450                 455                 460

Thr Val Trp Phe Pro Asp Met Ile Arg His Leu Gln Ala Val Asp Tyr
465                 470                 475                 480

Ala Ala Arg Thr Lys Val Phe Pro Gly Glu Arg Val Glu His Val Thr
            485                 490                 495

Phe Asn Phe Thr Leu Glu Asn Gln Ile His Arg Gly Gly Gln Tyr Phe
            500                 505                 510

Asn Asp Lys Phe Ile Gly Leu Arg Leu Lys Ser Val Ser Phe Glu Asp
            515                 520                 525

Ser Leu Phe Glu Glu Cys Tyr Phe Glu Asp Val Thr Ser Ser Asn Thr
            530                 535                 540

Phe Phe Arg Asn Cys Thr Phe Ile Asn Thr Val Phe Tyr Asn Thr Asp
545                 550                 555                 560

Leu Phe Glu Tyr Lys Phe Val Asn Ser Arg Leu Val Asn Ser Thr Phe
            565                 570                 575

Leu His Asn Lys Glu Gly Cys Pro Leu Asp Val Thr Gly Thr Gly Glu
            580                 585                 590

Gly Ala Tyr Met Val Tyr Phe Val Ser Phe Leu Gly Thr Leu Ala Val
            595                 600                 605

Leu Pro Gly Asn Ile Val Ser Ala Leu Leu Met Asp Lys Ile Gly Arg
            610                 615                 620

Leu Arg Met Leu Ala Gly Ser Ser Val Met Ser Cys Val Ser Cys Phe
625                 630                 635                 640

Phe Leu Ser Phe Gly Asn Ser Glu Ser Ala Met Ile Ala Leu Leu Cys
            645                 650                 655

Leu Phe Gly Gly Val Ser Ile Ala Ser Trp Asn Ala Leu Asp Val Leu
            660                 665                 670

Thr Val Glu Leu Tyr Pro Ser Asp Lys Arg Thr Thr Ala Phe Gly Phe
            675                 680                 685

Leu Asn Ala Leu Cys Lys Leu Ala Ala Val Leu Gly Ile Ser Ile Phe
            690                 695                 700

Thr Ser Phe Val Gly Ile Thr Lys Ala Ala Pro Ile Leu Phe Ala Ser
705                 710                 715                 720

Ala Ala Leu Ala Leu Gly Ser Ser Leu Ala Leu Lys Leu Pro Glu Thr
            725                 730                 735

Arg Gly Gln Val Leu Gln
            740
```

<210> SEQ ID NO 21
<211> LENGTH: 2175
<212> TYPE: DNA
<213> ORGANISM: Discopyge ommata
<220> FEATURE:
<221> NAME/KEY: CDS
<222> LOCATION: (1)..(2175)

<400> SEQUENCE: 21

| | | | | | | | | | | | | | | | | |
|---|---|---|---|---|---|---|---|---|---|---|---|---|---|---|---|---|
| atg | gat | gac | gct | tac | agg | aac | agg | act | acc | ctg | atg | aag | ggt | gcc | aaa | 48 |
| Met | Asp | Asp | Ala | Tyr | Arg | Asn | Arg | Thr | Thr | Leu | Met | Lys | Gly | Ala | Lys | |
| 1 | | | | 5 | | | | | 10 | | | | | 15 | | |
| gac | att | gcc | aaa | gaa | gtt | aag | aag | caa | aca | ata | aag | aaa | ggc | act | gtg | 96 |
| Asp | Ile | Ala | Lys | Glu | Val | Lys | Lys | Gln | Thr | Ile | Lys | Lys | Gly | Thr | Val | |
| | | | 20 | | | | | 25 | | | | | 30 | | | |
| gga | gca | gag | tac | acg | cag | gac | aga | tac | tca | aag | acc | gct | tat | gcc | aat | 144 |
| Gly | Ala | Glu | Tyr | Thr | Gln | Asp | Arg | Tyr | Ser | Lys | Thr | Ala | Tyr | Ala | Asn | |
| | 35 | | | | | 40 | | | | | 45 | | | | | |
| ttt | caa | gat | gat | gac | tgc | tac | aac | tat | agc | aga | ggg | acc | tat | gga | gaa | 192 |
| Phe | Gln | Asp | Asp | Asp | Cys | Tyr | Asn | Tyr | Ser | Arg | Gly | Thr | Tyr | Gly | Glu | |
| | 50 | | | | | 55 | | | | | 60 | | | | | |
| gaa | caa | caa | gag | gat | gag | ggt | tca | agt | gat | gcc | act | gaa | gga | cac | gat | 240 |
| Glu | Gln | Gln | Glu | Asp | Glu | Gly | Ser | Ser | Asp | Ala | Thr | Glu | Gly | His | Asp | |
| 65 | | | | | 70 | | | | | 75 | | | | | 80 | |
| gag | gag | gat | gag | att | tac | gaa | ggg | gag | tat | cag | ggg | atc | cct | gat | atg | 288 |
| Glu | Glu | Asp | Glu | Ile | Tyr | Glu | Gly | Glu | Tyr | Gln | Gly | Ile | Pro | Asp | Met | |
| | | | | 85 | | | | | 90 | | | | | 95 | | |
| agc | caa | aag | aag | gag | agc | cag | gtt | gcc | att | gga | caa | cta | gtc | tca | gat | 336 |
| Ser | Gln | Lys | Lys | Glu | Ser | Gln | Val | Ala | Ile | Gly | Gln | Leu | Val | Ser | Asp | |
| | | | 100 | | | | | 105 | | | | | 110 | | | |
| gag | tac | aag | gac | cgc | gag | gag | ctg | gat | gct | gag | agg | aga | gct | gat | gaa | 384 |
| Glu | Tyr | Lys | Asp | Arg | Glu | Glu | Leu | Asp | Ala | Glu | Arg | Arg | Ala | Asp | Glu | |
| | | 115 | | | | | 120 | | | | | 125 | | | | |
| gag | gag | ctg | gcg | cag | cag | tat | gag | ctg | atc | att | cag | gag | tgc | ggc | cat | 432 |
| Glu | Glu | Leu | Ala | Gln | Gln | Tyr | Glu | Leu | Ile | Ile | Gln | Glu | Cys | Gly | His | |
| | 130 | | | | | 135 | | | | | 140 | | | | | |
| ggg | cgg | ttc | cag | tgg | gca | ttg | ttc | ctt | gtg | cta | gga | ttg | tcc | ctc | atg | 480 |
| Gly | Arg | Phe | Gln | Trp | Ala | Leu | Phe | Leu | Val | Leu | Gly | Leu | Ser | Leu | Met | |
| 145 | | | | 150 | | | | | 155 | | | | | 160 | | |
| gct | gat | gga | gtg | gag | gtg | ttt | gtg | gtg | ggt | ttt | gtc | ctg | cca | agt | gct | 528 |
| Ala | Asp | Gly | Val | Glu | Val | Phe | Val | Val | Gly | Phe | Val | Leu | Pro | Ser | Ala | |
| | | | | 165 | | | | | 170 | | | | | 175 | | |
| gag | acg | gac | atg | tgt | gtt | gaa | aat | tcc | aat | tca | gga | tgg | ctg | ggc | agc | 576 |
| Glu | Thr | Asp | Met | Cys | Val | Glu | Asn | Ser | Asn | Ser | Gly | Trp | Leu | Gly | Ser | |
| | | | 180 | | | | | 185 | | | | | 190 | | | |
| ata | gtc | tac | ctt | ggg | atg | atg | ctc | ggg | gcc | ttt | ttc | tgg | ggt | ggt | tta | 624 |
| Ile | Val | Tyr | Leu | Gly | Met | Met | Leu | Gly | Ala | Phe | Phe | Trp | Gly | Gly | Leu | |
| | | 195 | | | | | 200 | | | | | 205 | | | | |
| gca | gac | aag | atg | ggc | cgt | cgg | caa | acc | ctc | att | att | tgt | atg | tcc | atc | 672 |
| Ala | Asp | Lys | Met | Gly | Arg | Arg | Gln | Thr | Leu | Ile | Ile | Cys | Met | Ser | Ile | |
| | 210 | | | | | 215 | | | | | 220 | | | | | |
| aac | gga | ttc | ttc | gcc | ttt | cta | tca | tct | ttt | gtc | cag | ggt | tac | agc | ctc | 720 |
| Asn | Gly | Phe | Phe | Ala | Phe | Leu | Ser | Ser | Phe | Val | Gln | Gly | Tyr | Ser | Leu | |
| 225 | | | | 230 | | | | | 235 | | | | | 240 | | |
| ttc | ctt | ttc | tgc | cga | ttc | ttt | gct | gga | ttt | ggg | att | gga | gga | gca | gtt | 768 |
| Phe | Leu | Phe | Cys | Arg | Phe | Phe | Ala | Gly | Phe | Gly | Ile | Gly | Gly | Ala | Val | |
| | | | | 245 | | | | | 250 | | | | | 255 | | |
| cca | gtt | gtg | ttt | gcc | tac | ttt | gcg | gaa | gtc | ctg | gcc | cgg | gag | aag | cgg | 816 |
| Pro | Val | Val | Phe | Ala | Tyr | Phe | Ala | Glu | Val | Leu | Ala | Arg | Glu | Lys | Arg | |
| | | | 260 | | | | | 265 | | | | | 270 | | | |
| ggt | gag | cac | ttg | agc | tgg | ctc | tgc | atg | ttc | tgg | atg | atc | gga | ggg | atc | 864 |
| Gly | Glu | His | Leu | Ser | Trp | Leu | Cys | Met | Phe | Trp | Met | Ile | Gly | Gly | Ile | |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     | 275 |     |     |     | 280 |     |     |     |     | 285 |     |     |     |     |      |
| tac | gca | tcg | gcc | atg | gca | tgg | gcc | atc | att | cct | cac | tat | ggt | tgg | agt | 912  |
| Tyr | Ala | Ser | Ala | Met | Ala | Trp | Ala | Ile | Ile | Pro | His | Tyr | Gly | Trp | Ser |      |
|     | 290 |     |     |     |     | 295 |     |     |     |     | 300 |     |     |     |     |      |
| ttc | agt | atg | ggt | tct | gcg | tac | cag | ttc | cac | agc | tgg | cga | gtg | ttt | gtc | 960  |
| Phe | Ser | Met | Gly | Ser | Ala | Tyr | Gln | Phe | His | Ser | Trp | Arg | Val | Phe | Val |      |
| 305 |     |     |     |     | 310 |     |     |     |     | 315 |     |     |     |     | 320 |      |
| gtt | gtc | tgt | gca | ctt | ccc | tgc | atg | tcc | tca | gtt | gtg | gca | ctc | acc | ttc | 1008 |
| Val | Val | Cys | Ala | Leu | Pro | Cys | Met | Ser | Ser | Val | Val | Ala | Leu | Thr | Phe |      |
|     |     |     |     | 325 |     |     |     |     | 330 |     |     |     |     | 335 |     |      |
| atg | cct | gaa | agt | cct | cga | tat | ctg | ctg | gag | gta | gga | aaa | cat | gat | gag | 1056 |
| Met | Pro | Glu | Ser | Pro | Arg | Tyr | Leu | Leu | Glu | Val | Gly | Lys | His | Asp | Glu |      |
|     |     |     | 340 |     |     |     |     | 345 |     |     |     |     | 350 |     |     |      |
| gcc | tgg | atg | att | ctg | aag | caa | atc | cat | gac | aca | aac | atg | aga | gcg | cgg | 1104 |
| Ala | Trp | Met | Ile | Leu | Lys | Gln | Ile | His | Asp | Thr | Asn | Met | Arg | Ala | Arg |      |
|     |     | 355 |     |     |     |     | 360 |     |     |     |     | 365 |     |     |     |      |
| gga | caa | cct | gag | aaa | gtg | ttc | acg | gtc | aat | aga | atc | aag | act | ccc | aag | 1152 |
| Gly | Gln | Pro | Glu | Lys | Val | Phe | Thr | Val | Asn | Arg | Ile | Lys | Thr | Pro | Lys |      |
|     | 370 |     |     |     |     | 375 |     |     |     |     | 380 |     |     |     |     |      |
| ttg | att | gat | gaa | ttg | ata | gag | atc | cag | aca | gac | aca | ggc | acc | tgg | tat | 1200 |
| Leu | Ile | Asp | Glu | Leu | Ile | Glu | Ile | Gln | Thr | Asp | Thr | Gly | Thr | Trp | Tyr |      |
| 385 |     |     |     |     | 390 |     |     |     |     | 395 |     |     |     |     | 400 |      |
| atg | agg | tgg | ttt | gtt | cga | atc | aaa | act | gaa | atg | tat | gga | att | tgg | ttg | 1248 |
| Met | Arg | Trp | Phe | Val | Arg | Ile | Lys | Thr | Glu | Met | Tyr | Gly | Ile | Trp | Leu |      |
|     |     |     |     | 405 |     |     |     |     | 410 |     |     |     |     | 415 |     |      |
| aca | ttc | atg | aga | tgt | tta | gac | tat | cct | gtc | aaa | cga | aac | acc | att | ctt | 1296 |
| Thr | Phe | Met | Arg | Cys | Leu | Asp | Tyr | Pro | Val | Lys | Arg | Asn | Thr | Ile | Leu |      |
|     |     |     | 420 |     |     |     |     | 425 |     |     |     |     | 430 |     |     |      |
| ctg | att | ata | gtt | tgg | aca | acc | tta | tca | ttt | ggt | tac | tat | ggt | ctc | tct | 1344 |
| Leu | Ile | Ile | Val | Trp | Thr | Thr | Leu | Ser | Phe | Gly | Tyr | Tyr | Gly | Leu | Ser |      |
|     |     | 435 |     |     |     |     | 440 |     |     |     |     | 445 |     |     |     |      |
| gtc | tgg | ttc | cct | gat | gtt | atc | aaa | cac | ctt | cag | gct | gat | gag | tat | gca | 1392 |
| Val | Trp | Phe | Pro | Asp | Val | Ile | Lys | His | Leu | Gln | Ala | Asp | Glu | Tyr | Ala |      |
|     | 450 |     |     |     |     | 455 |     |     |     |     | 460 |     |     |     |     |      |
| tcc | cgg | gtg | aaa | agg | ttt | tat | gga | gaa | aaa | gtt | gaa | gat | ttt | gtg | ttc | 1440 |
| Ser | Arg | Val | Lys | Arg | Phe | Tyr | Gly | Glu | Lys | Val | Glu | Asp | Phe | Val | Phe |      |
| 465 |     |     |     |     | 470 |     |     |     |     | 475 |     |     |     |     | 480 |      |
| aac | ttt | acg | ctg | gaa | aac | cag | atc | cac | act | aat | gga | gag | tac | atc | aga | 1488 |
| Asn | Phe | Thr | Leu | Glu | Asn | Gln | Ile | His | Thr | Asn | Gly | Glu | Tyr | Ile | Arg |      |
|     |     |     |     | 485 |     |     |     |     | 490 |     |     |     |     | 495 |     |      |
| gac | agg | ttc | acc | atc | atg | aag | ttt | aaa | gca | gta | aca | ttc | gag | gat | tcc | 1536 |
| Asp | Arg | Phe | Thr | Ile | Met | Lys | Phe | Lys | Ala | Val | Thr | Phe | Glu | Asp | Ser |      |
|     |     |     | 500 |     |     |     |     | 505 |     |     |     |     | 510 |     |     |      |
| ctc | ttt | aag | aac | tgt | tat | ttt | gaa | gat | atc | aca | tcg | ttg | tct | act | tat | 1584 |
| Leu | Phe | Lys | Asn | Cys | Tyr | Phe | Glu | Asp | Ile | Thr | Ser | Leu | Ser | Thr | Tyr |      |
|     |     | 515 |     |     |     |     | 520 |     |     |     |     | 525 |     |     |     |      |
| ttt | aag | aac | tgc | aca | ttt | aca | gaa | acc | ctt | ttc | tat | aat | aca | gat | ctc | 1632 |
| Phe | Lys | Asn | Cys | Thr | Phe | Thr | Glu | Thr | Leu | Phe | Tyr | Asn | Thr | Asp | Leu |      |
|     | 530 |     |     |     |     | 535 |     |     |     |     | 540 |     |     |     |     |      |
| gaa | gag | ttt | aaa | ttc | att | gat | tgt | caa | ttt | atc | aat | tcc | aca | ttt | ctg | 1680 |
| Glu | Glu | Phe | Lys | Phe | Ile | Asp | Cys | Gln | Phe | Ile | Asn | Ser | Thr | Phe | Leu |      |
| 545 |     |     |     |     | 550 |     |     |     |     | 555 |     |     |     |     | 560 |      |
| cac | aat | aag | aaa | ggc | tgt | cag | att | aac | ttt | gac | gaa | gac | tac | agt | gcc | 1728 |
| His | Asn | Lys | Lys | Gly | Cys | Gln | Ile | Asn | Phe | Asp | Glu | Asp | Tyr | Ser | Ala |      |
|     |     |     |     | 565 |     |     |     |     | 570 |     |     |     |     | 575 |     |      |
| tac | tgg | att | tat | ttt | gtc | aac | ttc | cta | gga | aca | ctg | gca | gtg | ttg | cca | 1776 |
| Tyr | Trp | Ile | Tyr | Phe | Val | Asn | Phe | Leu | Gly | Thr | Leu | Ala | Val | Leu | Pro |      |
|     |     |     | 580 |     |     |     |     | 585 |     |     |     |     | 590 |     |     |      |
| ggc | aac | att | gta | tct | gca | ttg | ctc | atg | gac | agg | att | gga | cgc | ctg | aca | 1824 |
| Gly | Asn | Ile | Val | Ser | Ala | Leu | Leu | Met | Asp | Arg | Ile | Gly | Arg | Leu | Thr |      |

```
                  595                 600                 605
atg tta ggt ggc tcc atg gtt ctg tct ggg atc agc tgc ttc ttc ctg      1872
Met Leu Gly Gly Ser Met Val Leu Ser Gly Ile Ser Cys Phe Phe Leu
    610                 615                 620 tgg ttt ggg aca agt gaa gcc atg atg att gga atg ttg tgc ctg tac      1920
Trp Phe Gly Thr Ser Glu Ala Met Met Ile Gly Met Leu Cys Leu Tyr
625                 630                 635                 640 aat gga ctg act att tca gcg tgg aac tcc ctt gac gtg atc act gtg      1968
Asn Gly Leu Thr Ile Ser Ala Trp Asn Ser Leu Asp Val Ile Thr Val
                645                 650                 655 gaa ctt ctg cca act gac aga aga gca act gga ttt gga ttt ttg aat      2016
Glu Leu Leu Pro Thr Asp Arg Arg Ala Thr Gly Phe Gly Phe Leu Asn
            660                 665                 670 gcc ctg tgc aaa gct gcg act gta ctt gga aat ctc att ttt ggt tct      2064
Ala Leu Cys Lys Ala Ala Thr Val Leu Gly Asn Leu Ile Phe Gly Ser
        675                 680                 685 ttg gtc ggt ata acc aaa tcg atc ccg att atg tta gca tcc act gtc      2112
Leu Val Gly Ile Thr Lys Ser Ile Pro Ile Met Leu Ala Ser Thr Val
    690                 695                 700 cta gtc tgc gga ggc ctc gtg gga ctc cga ctt cct gac aca agg aac      2160
Leu Val Cys Gly Gly Leu Val Gly Leu Arg Leu Pro Asp Thr Arg Asn
705                 710                 715                 720 cag gtg ctc atg tga                                                  2175
Gln Val Leu Met <210> SEQ ID NO 22
<211> LENGTH: 724
<212> TYPE: PRT
<213> ORGANISM: Discopyge ommata

<400> SEQUENCE: 22

Met Asp Asp Ala Tyr Arg Asn Arg Thr Thr Leu Met Lys Gly Ala Lys
1               5                   10                  15

Asp Ile Ala Lys Glu Val Lys Lys Gln Thr Ile Lys Lys Gly Thr Val
            20                  25                  30

Gly Ala Glu Tyr Thr Gln Asp Arg Tyr Ser Lys Thr Ala Tyr Ala Asn
        35                  40                  45

Phe Gln Asp Asp Asp Cys Tyr Asn Tyr Ser Arg Gly Thr Tyr Gly Glu
    50                  55                  60

Glu Gln Gln Glu Asp Glu Gly Ser Ser Asp Ala Thr Glu Gly His Asp
65                  70                  75                  80

Glu Glu Asp Glu Ile Tyr Glu Gly Tyr Gln Gly Ile Pro Asp Met
                85                  90                  95

Ser Gln Lys Lys Glu Ser Gln Val Ala Ile Gly Gln Leu Val Ser Asp
            100                 105                 110

Glu Tyr Lys Asp Arg Glu Glu Leu Asp Ala Glu Arg Arg Ala Asp Glu
        115                 120                 125

Glu Glu Leu Ala Gln Gln Tyr Glu Leu Ile Ile Gln Glu Cys Gly His
    130                 135                 140

Gly Arg Phe Gln Trp Ala Leu Phe Leu Val Leu Gly Leu Ser Leu Met
145                 150                 155                 160

Ala Asp Gly Val Glu Val Phe Val Val Gly Phe Val Leu Pro Ser Ala
                165                 170                 175

Glu Thr Asp Met Cys Val Glu Asn Ser Asn Ser Gly Trp Leu Gly Ser
            180                 185                 190

Ile Val Tyr Leu Gly Met Met Leu Gly Ala Phe Phe Trp Gly Gly Leu
        195                 200                 205
```

-continued

```
Ala Asp Lys Met Gly Arg Arg Gln Thr Leu Ile Ile Cys Met Ser Ile
    210                 215                 220

Asn Gly Phe Phe Ala Phe Leu Ser Ser Phe Val Gln Gly Tyr Ser Leu
225                 230                 235                 240

Phe Leu Phe Cys Arg Phe Phe Ala Gly Phe Ile Gly Gly Ala Val
                245                 250                 255

Pro Val Val Phe Ala Tyr Phe Ala Glu Val Leu Ala Arg Glu Lys Arg
                260                 265                 270

Gly Glu His Leu Ser Trp Leu Cys Met Phe Trp Met Ile Gly Gly Ile
            275                 280                 285

Tyr Ala Ser Ala Met Ala Trp Ala Ile Ile Pro His Tyr Gly Trp Ser
    290                 295                 300

Phe Ser Met Gly Ser Ala Tyr Gln Phe His Ser Trp Arg Val Phe Val
305                 310                 315                 320

Val Val Cys Ala Leu Pro Cys Met Ser Ser Val Val Ala Leu Thr Phe
                325                 330                 335

Met Pro Glu Ser Pro Arg Tyr Leu Leu Glu Val Gly Lys His Asp Glu
                340                 345                 350

Ala Trp Met Ile Leu Lys Gln Ile His Asp Thr Asn Met Arg Ala Arg
            355                 360                 365

Gly Gln Pro Glu Lys Val Phe Thr Val Asn Arg Ile Lys Thr Pro Lys
    370                 375                 380

Leu Ile Asp Glu Leu Ile Glu Ile Gln Thr Asp Thr Gly Thr Trp Tyr
385                 390                 395                 400

Met Arg Trp Phe Val Arg Ile Lys Thr Glu Met Tyr Gly Ile Trp Leu
                405                 410                 415

Thr Phe Met Arg Cys Leu Asp Tyr Pro Val Lys Arg Asn Thr Ile Leu
                420                 425                 430

Leu Ile Ile Val Trp Thr Thr Leu Ser Phe Gly Tyr Tyr Gly Leu Ser
            435                 440                 445

Val Trp Phe Pro Asp Val Ile Lys His Leu Gln Ala Asp Glu Tyr Ala
    450                 455                 460

Ser Arg Val Lys Arg Phe Tyr Gly Glu Lys Val Glu Asp Phe Val Phe
465                 470                 475                 480

Asn Phe Thr Leu Glu Asn Gln Ile His Thr Asn Gly Glu Tyr Ile Arg
                485                 490                 495

Asp Arg Phe Thr Ile Met Lys Phe Lys Ala Val Thr Phe Glu Asp Ser
                500                 505                 510

Leu Phe Lys Asn Cys Tyr Phe Glu Asp Ile Thr Ser Leu Ser Thr Tyr
            515                 520                 525

Phe Lys Asn Cys Thr Phe Thr Glu Thr Leu Phe Tyr Asn Thr Asp Leu
    530                 535                 540

Glu Glu Phe Lys Phe Ile Asp Cys Gln Phe Ile Asn Ser Thr Phe Leu
545                 550                 555                 560

His Asn Lys Lys Gly Cys Gln Ile Asn Phe Asp Glu Asp Tyr Ser Ala
                565                 570                 575

Tyr Trp Ile Tyr Phe Val Asn Phe Leu Gly Thr Leu Ala Val Leu Pro
                580                 585                 590

Gly Asn Ile Val Ser Ala Leu Leu Met Asp Arg Ile Gly Arg Leu Thr
            595                 600                 605

Met Leu Gly Gly Ser Met Val Leu Ser Gly Ile Ser Cys Phe Phe Leu
    610                 615                 620

Trp Phe Gly Thr Ser Glu Ala Met Met Ile Gly Met Leu Cys Leu Tyr
625                 630                 635                 640
```

```
Asn Gly Leu Thr Ile Ser Ala Trp Asn Ser Leu Asp Val Ile Thr Val
                645                 650                 655

Glu Leu Leu Pro Thr Asp Arg Arg Ala Thr Gly Phe Gly Phe Leu Asn
            660                 665                 670

Ala Leu Cys Lys Ala Ala Thr Val Leu Gly Asn Leu Ile Phe Gly Ser
        675                 680                 685

Leu Val Gly Ile Thr Lys Ser Ile Pro Ile Met Leu Ala Ser Thr Val
    690                 695                 700

Leu Val Cys Gly Gly Leu Val Gly Leu Arg Leu Pro Asp Thr Arg Asn
705                 710                 715                 720

Gln Val Leu Met

<210> SEQ ID NO 23
<211> LENGTH: 38
<212> TYPE: PRT
<213> ORGANISM: Rattus norvegicus
<220> FEATURE:
<221> NAME/KEY: MISC_FEATURE
<222> LOCATION: (13)..(14)
<223> OTHER INFORMATION: X1 IS L OR V
<220> FEATURE:
<221> NAME/KEY: MISC_FEATURE
<222> LOCATION: (15)..(16)
<223> OTHER INFORMATION: X IS E OR D
<220> FEATURE:
<221> NAME/KEY: MISC_FEATURE
<222> LOCATION: (30)..(31)
<223> OTHER INFORMATION: X IS Q OR K

<400> SEQUENCE: 23

Asn Thr Tyr Phe Lys Asn Cys Thr Phe Ile Asp Thr Xaa Phe Xaa Asn
1               5                   10                  15

Thr Asp Phe Glu Pro Tyr Lys Phe Ile Asp Ser Glu Phe Xaa Asn Cys
            20                  25                  30

Ser Phe Leu His Asn Lys
            35
```